US007754705B2

(12) United States Patent
Savage et al.

(10) Patent No.: US 7,754,705 B2
(45) Date of Patent: Jul. 13, 2010

(54) CATIONIC STEROID ANTIMICROBIAL COMPOSITIONS AND METHODS OF USE

(75) Inventors: Paul B. Savage, Mapleton, UT (US); Donald Y Leung, Englewood, CO (US)

(73) Assignees: Brigham Young University, Provo, UT (US); National Jewish Medical and Research Center, Denver, CO (US)

(*) Notice: Subject to any disclaimer, the term of this patent is extended or adjusted under 35 U.S.C. 154(b) by 83 days.

(21) Appl. No.: 11/669,866

(22) Filed: Jan. 31, 2007

(65) Prior Publication Data
US 2007/0190066 A1 Aug. 16, 2007

Related U.S. Application Data

(60) Provisional application No. 60/764,218, filed on Feb. 1, 2006.

(51) Int. Cl.
*A61K 31/56* (2006.01)

(52) U.S. Cl. .................................. 514/182; 514/169
(58) Field of Classification Search ....................... None
See application file for complete search history.

(56) References Cited

U.S. PATENT DOCUMENTS

| 5,763,430 A | 6/1998 | Zasloff ............ 514/182 |
| 6,143,738 A | 11/2000 | Zasloff ............ 514/181 |
| 6,486,148 B2 | 11/2002 | Savage et al. ...... 514/182 |
| 6,767,904 B2 | 7/2004 | Savage et al. ...... 514/182 |

FOREIGN PATENT DOCUMENTS

WO 96/08270 A2 3/1996

OTHER PUBLICATIONS

Sato, et al. A simple and rapid method for preliminary evaluation of in vivo efficacy of anti-HIV compounds in mice. Antiviral Research 27 (1995) 151-163.*
DiBisceglie, et al. New therapeutic strategies for hepatitis C. Hepatology. Jan. 2002;35(1):224-31.*
Savage, P.B., et al., Antibacterial Properties of Cationic Steroid Antibiotics, FEMS Microbiology Letters 217:1-7 (2002).
Leung, D.Y.M, et al., Cationic Steroid Antibiotics (CSA) Exhibit Cytotoxic Activity Against Vaccinia Virus (VV), http://www.abstractsonline.com, Control/Tracking No. 05-A-1943-AAAAI, Sep. 20, 2004.
Cassimatis, Dimitri C., et al., Smallpox Vaccination and Myopericarditis: A Clinical Review, Journal of the American College of Cardiology (2004), 43(9) 1503-1510.

* cited by examiner

*Primary Examiner*—Mary E Mosher
*Assistant Examiner*—Stuart W Snyder
(74) *Attorney, Agent, or Firm*—Pillsbury Winthrop Shaw Pittman, LLP

(57) ABSTRACT

The invention provides methods for decreasing or inhibiting poxvirus infection or pathogenesis of a cell in vitro, ex vivo or in vivo, a symptom or pathology associated with poxvirus infection or pathogenesis in vitro, ex vivo or in vivo, or an adverse side effect of poxvirus infection or pathogenesis in vitro, ex vivo or in vivo. In one embodiment, a method of the invention includes treating a subject with an invention compound (e.g., cationic steroid antimicrobial or CSA).

19 Claims, 9 Drawing Sheets

CSA-10

140

CSA-31

132

Figure 1:
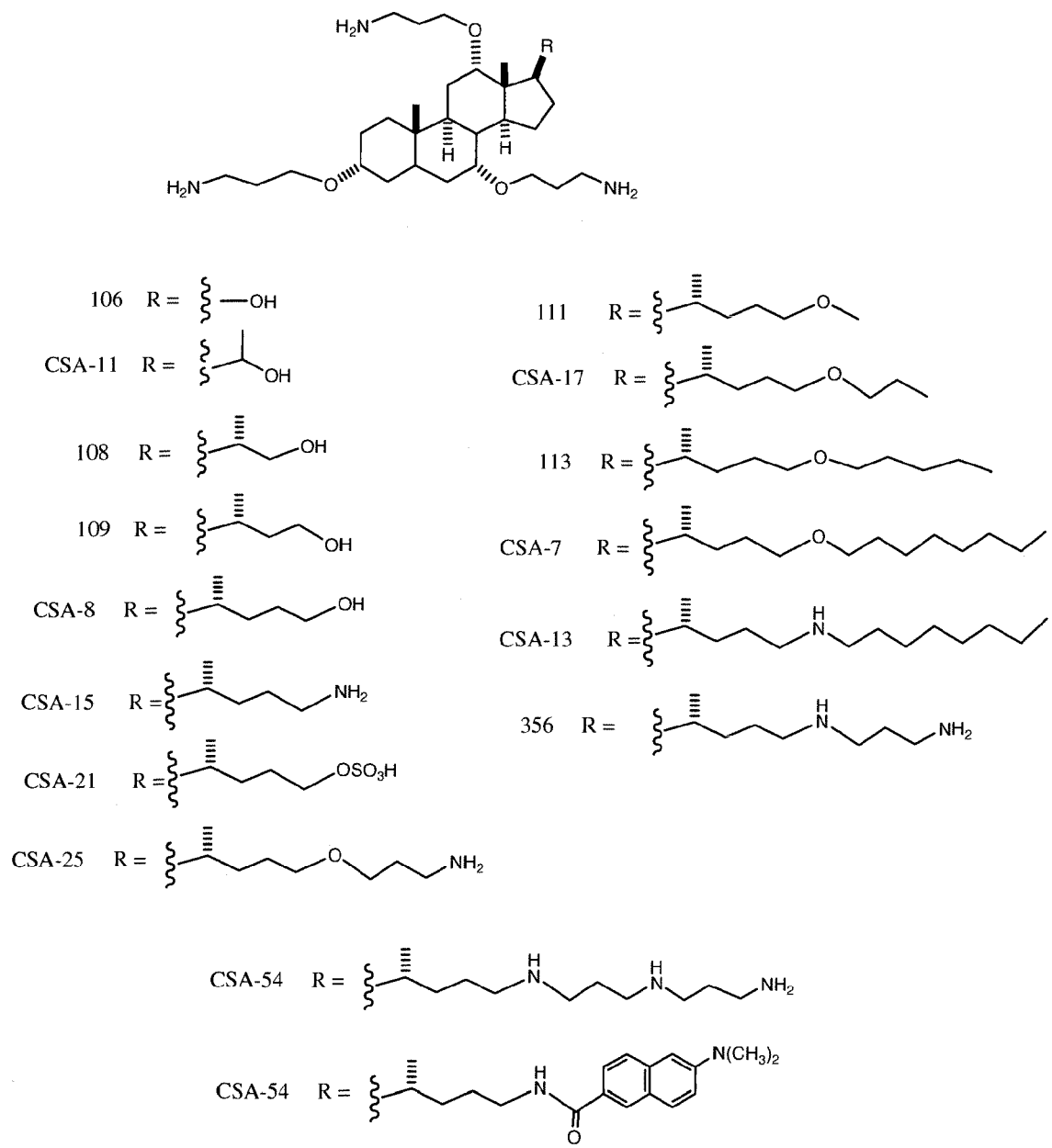
Figure 2:
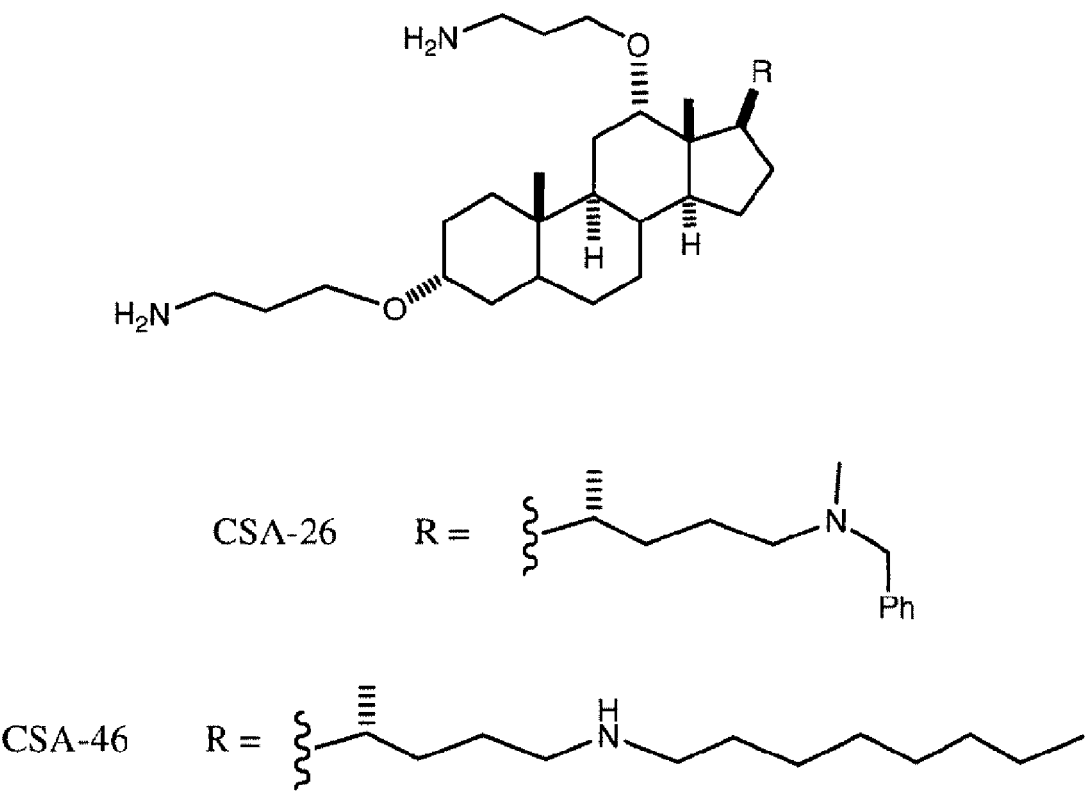
Figure 3:
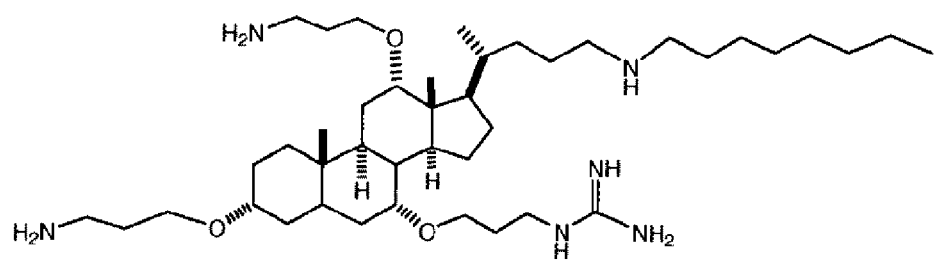
Figure 4:
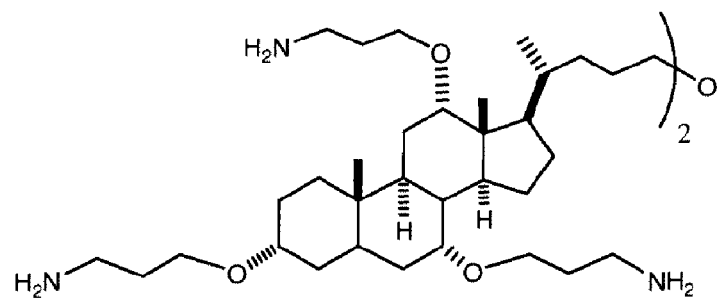
Figure 5:
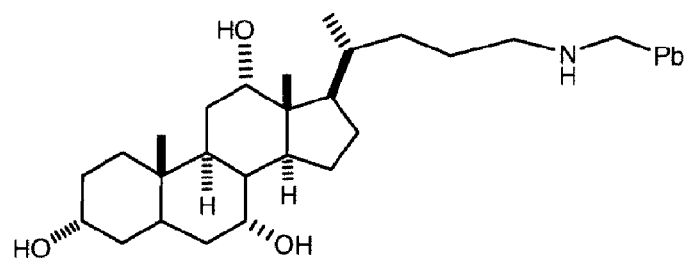
Figure 6:
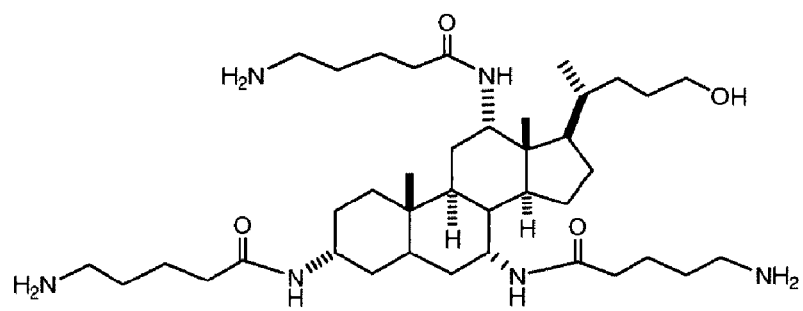
Figure 7:
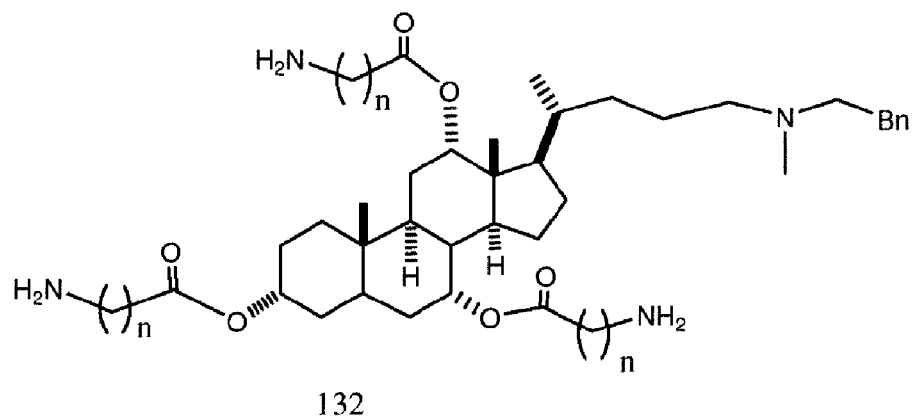
Figure 8:
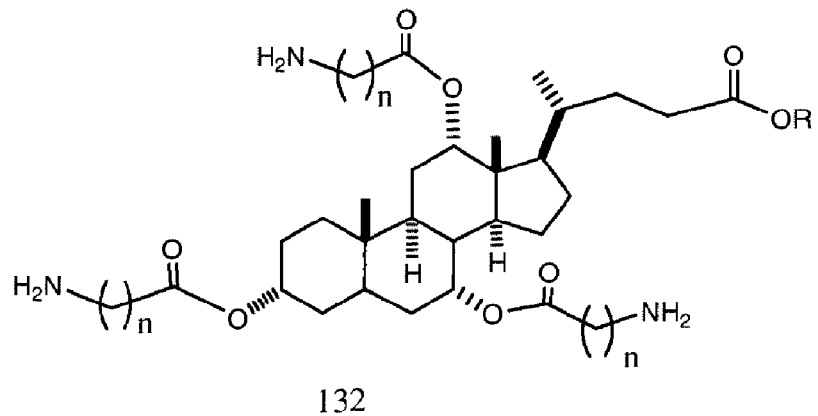

352  n = 1
353  n = 2
354  n = 3

132

341  n = 1,  R = -(CH$_2$)$_7$CH$_3$
342  n = 2,  R = -(CH$_2$)$_7$CH$_3$
343  n = 3   R = -(CH$_2$)$_7$CH$_3$
324  n = 1   R = -CH$_2$CH$_2$N$^+$(CH$_3$)$_3$
325  n = 2   R = -CH$_2$CH$_2$N$^+$(CH$_3$)$_3$
326  n = 3   R = -CH$_2$CH$_2$N$^+$(CH$_3$)$_3$
327  n = 1   R = -H

358

```
                      SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Forward
      primer

<400> SEQUENCE: 1
gccaatgagg gttcgagttc                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Reverse
      primer

<400> SEQUENCE: 2
caacatcccg tcgttcatca                                                  20
```

US 7,754,705 B2

CATIONIC STEROID ANTIMICROBIAL COMPOSITIONS AND METHODS OF USE

RELATED APPLICATIONS

This application claims the benefit of priority of provisional application Ser. No. 60/764,218, filed Feb. 1, 2006, which is expressly incorporated herein by reference.

GOVERNMENT FUNDING

This invention was made with Government support under grant N01-AI-40029, awarded by the National Institutes of Health. The Government has certain rights to this invention.

TECHNICAL FIELD

The invention relates to methods for decreasing or inhibiting poxvirus infection or pathogenesis of a cell in vitro, ex vivo or in vivo, a symptom or pathology associated with poxvirus infection or pathogenesis in vitro, ex vivo or in vivo, or an adverse side effect of poxvirus infection or pathogenesis in vitro, ex vivo or in vivo. In one embodiment, a method of the invention includes treating a subject with an invention compound (e.g., cationic steroid antimicrobial or CSA).

INTRODUCTION

A smallpox vaccine was the first human vaccine, and vaccinia virus (VV) is considered the most successful human vaccine, bringing about the worldwide eradication of smallpox disease. Mechanisms of adaptive immune protection elicited by the smallpox vaccine in humans generally remain unclear.

There is currently greatly renewed interest in smallpox due to the possible threat of bioterrorism (Henderson et al., *Jama* 281:2127 (1999)). Given this concern, there has been much discussion both about the mechanisms of protection afforded by the smallpox vaccine and possible development of alternatives to vaccines such as Dryvax®.

SUMMARY

Cationic steroid antimicrobials (CSAs) were developed as functional mimics of endogenous peptide antibiotics such as LL-37. A series of CSAs have been developed and CSAs are highly active against specific lipid-enveloped viruses including poxvirus (vaccinia). Antiviral activities of multiple CSAs have been measured, and active and inactive forms have been identified. In addition, CSAs preferentially associate with viral envelopes over host cells (keratinocytes).

DESCRIPTION OF THE DRAWINGS

FIG. 1 is a drawing showing compounds of the invention.

FIG. 2 is a drawing showing compounds CSA-26 and CSA-46.

FIG. 3 is a drawing showing compound 134.

FIG. 4 is a drawing showing compound CSA-10.

FIG. 5 is a dr awing showing compound 140.

FIG. 6 is a drawing showing compound CSA-31.

FIG. 7 is a drawing showing compounds 352-354.

FIG. 8 is a drawing showing compounds 341-343 and 324-327.

FIG. 9 is a drawing showing compounds 358.

FIGS. 10A and 10B are drawings showing various compounds of the invention (CSAs).

FIG. 11 shows the ability of CSA-8, -13 and -31 to kill vaccinia virus.

FIG. 12 shows Vaccinia virus killing by CSAs determined by quantification of viral RNA.

FIG. 13 shows fluorescence of CSA-59 (450 nm) in the presence of varied amounts of surface area of vaccinia virus and keratinocytes. The number of PFU of vaccinia and numbers of keratinocytes were varied, and surface areas were plotted to account for the large difference in surface area of the virus and cells. An increase in fluorescence of CSA-59 has been correlated to incorporation of CSA in a lipid bilayer.

DETAILED DESCRIPTION

In accordance with the invention, there are provided methods for decreasing or inhibiting poxvirus infection or pathogenesis of a cell in vitro, ex vivo or in vivo, a symptom or pathology associated with poxvirus infection or pathogenesis in vitro, ex vivo or in vivo, or an adverse side effect of poxvirus infection or pathogenesis in vitro, ex vivo or in vivo. In one embodiment, a method of the invention includes treating a subject with an invention compound (e.g., cationic steroid antimicrobial or CSA), wherein the subject is in need of treatment due to CSA anti-poxvirus activity or function, in order to provide the subject with a beneficial effect or improvement. In another embodiment, a method of the invention includes providing a subject with protection against a poxvirus infection or pathogenesis by administering a composition comprising a sufficient amount of CSA to provide the subject with protection against a poxvirus infection or pathogenesis. In a further embodiment, a method of the invention includes treating a subject for poxvirus infection or pathogenesis by administering a composition comprising a sufficient amount of CSA to treat the subject for the poxvirus infection or pathogenesis. In an additional embodiment, a method of the invention includes decreasing susceptibility of a subject to a poxvirus infection or pathogenesis by administering a composition comprising a sufficient amount of CSA to decrease susceptibility of the subject to a poxvirus infection or pathogenesis. Methods of the invention include administering CSA prior to, concurrently with, or following contact of the subject with or exposure of the subject to a poxvirus; and administering CSA prior to, concurrently with, or following development of a symptom or pathology associated with or caused by poxvirus infection. In various aspects, a compound of the invention (e.g., CSA) is administered prior to (prophylaxis), concurrently with or following infection or exposure of the subject (therapeutic) to a poxvirus.

The invention treatment methods therefore include, among other things, therapeutic and prophylactic methods. Subjects can be contacted with, administered ex vivo or in vivo delivered a compound of the invention (e.g., CSA) prior to, concurrently with or following poxvirus exposure or contact, poxvirus infection, or development of a symptom or pathology associated with or caused by a poxvirus infection or pathogenesis.

The term "therapeutic" and grammatical variations thereof means the subject has a poxvirus infection, for example, the subject exhibits one or more symptoms or pathologies associated with or caused by poxvirus infection or pathogenesis as set forth herein or known in the art. The term "therapeutic" also includes a subject that has been exposed to or contacted with a poxvirus but may not exhibit one or more symptoms or pathologies associated with or caused by poxvirus infection or pathogenesis, as set forth herein or known in the art.

"Prophylaxis" and grammatical variations thereof refer to contact, administration or in vivo delivery to a subject prior to a known contact with or exposure to poxvirus. In situations where it is not known if a subject has been contacted with or exposed to poxvirus, contact with, administration or in vivo delivery of a compound to a subject occurs prior to manifestation or onset of a symptom associated with or caused by poxvirus infection or pathogenesis. In such a method, the effect of contact with, administration or in vivo delivery of a compound of the invention (e.g., CSA) can be to eliminate, prevent, inhibit, decrease or reduce the probability of or susceptibility towards developing a poxvirus infection or pathogenesis, or a symptom or pathology associated with or caused by poxvirus infection or pathogenesis.

As used herein, the term "associated with," when used in reference to the relationship between a symptom, pathology or adverse side effect of vaccination, and a poxvirus, means that the symptom, pathology or side effect is caused by poxvirus infection, pathogenesis or vaccination, or is a secondary effect of the poxvirus infection, pathogenesis or vaccination. A symptom, pathology or side effect that is present in a subject may therefore be the direct result of or caused by the poxvirus infection, pathogenesis or vaccination, or may be due at least in part to the subject reacting or responding to poxvirus infection, pathogenesis or vaccination (e.g., the immunological response). For example, a symptom or pathology that occurs during a poxvirus infection, pathogenesis or vaccination may be due in part to an inflammatory response of the subject.

The invention also provides methods for decreasing or preventing an adverse side effect caused by vaccination of a subject with a poxvirus. In one embodiment, a method includes administering a sufficient amount of CSA to the subject to decrease or prevent an adverse side effect caused by vaccination with a poxvirus. In one aspect, the poxvirus comprises a Vaccinia virus.

Figure 10A:
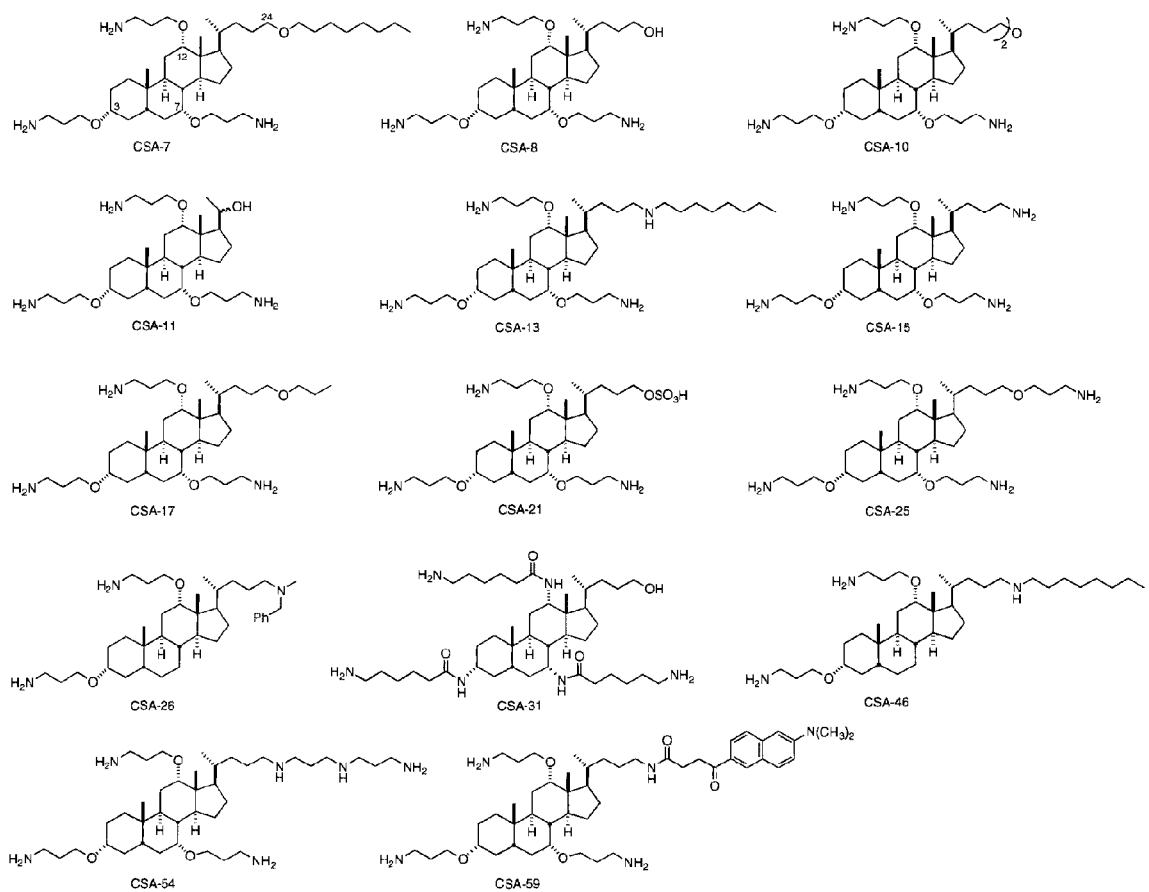
Figure 10B:
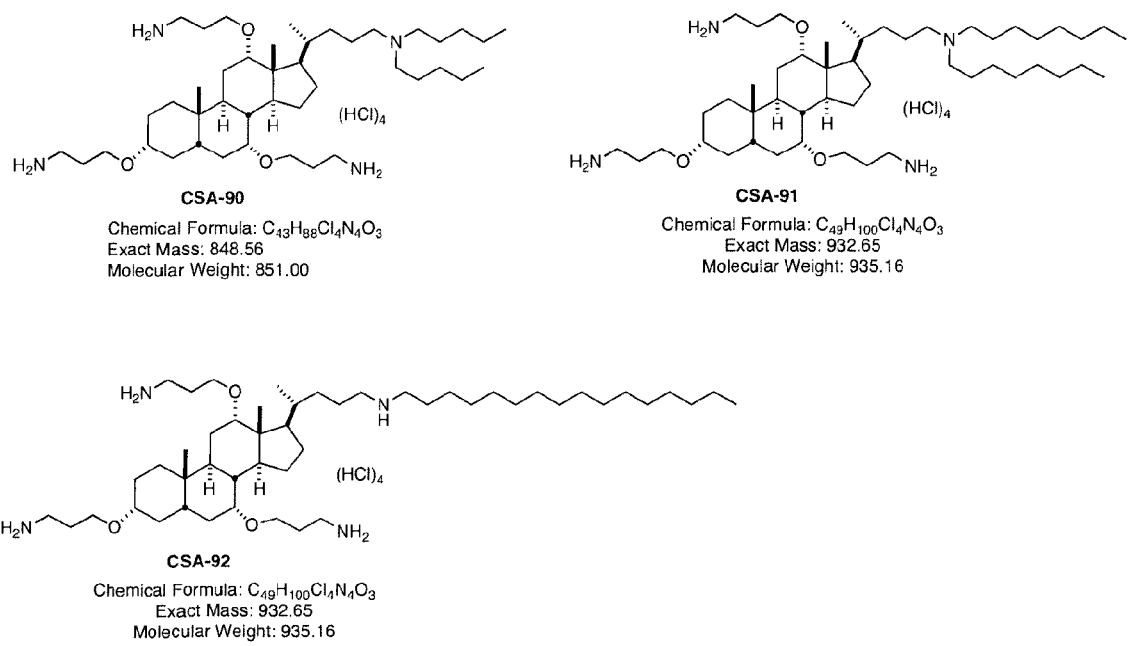

In particular embodiments of the compounds and methods of the invention, a CSA is selected from: CSA-7, CSA-8, CSA-10, CSA-11, CSA-13, CSA-15, CSA-17, CSA-21, CSA-25, CSA-26, CSA-31, CSA-46, CSA-54 and CSA-59, as set forth in FIG. 10. In other embodiments, a CSA does not have a charged group at position C24 or a CSA has a hydrophobic moiety at position C24 (e.g., a lipid). In additional embodiments, a CSA has a charged group at position C7. In further embodiments, a CSA comprises a multimer (e.g., a dimer, trimer, tetramer or higher order polymer). In yet additional embodiments, a CSA has a shorter tether length between the steroid scaffold and any amine group at positions C3, C7 or C12, relative to the tether length between the steroid scaffold and any amine group at positions C3, C7 or C12 of CSA-7, CSA-8, CSA-10, CSA-11, CSA-13, CSA-15, CSA-17, CSA-21, CSA-25, CSA-26, CSA-31, CSA-46, CSA-54 or CSA-59, as set forth in FIG. 10.

Methods of treatment include reducing, decreasing, inhibiting, ameliorating or preventing onset, severity, duration, progression, frequency or probability of one or more adverse side effects associated with poxvirus vaccination. Non-limiting examples of adverse side affects associated with poxvirus vaccination treatable with a compound of the invention include postvaccinial encephalitis, progressive vaccinia-necrosum, eczema vaccinatum, Vaccinia Keratitis, generalized vaccinia, myopericarditis, inoculation of other sites, infection of close contacts, rash and periocular infection and death.

Methods of the invention, including, for example, prophylactic and therapeutic treatment methods, as well as methods for decreasing or preventing an adverse side effect caused by vaccination with or against poxvirus, are applicable to poxvirus generally, more specifically, the members of the family Poxviridae. Poxvirus includes any strain or isolate or subtype or a species of poxvirus, or combination of strains or isolates or subtypes or species of poxviruses. Particular examples are infectious or pathogenic viruses. Specific non-limiting examples of poxvirus the subject of treatment with an invention compound (e.g., CSA) include, for example, live or attenuated pathogenic and non-pathogenic poxvirus. Exemplary pathogenic poxvirus include, variola major and variola minor smallpox virus. Particular non-limiting examples of variola major or variola minor smallpox virus include extracellular enveloped virus (EEV), intracellular mature virus (IMV) and cell-associated virus (CEV) forms. Additional exemplary pathogenic poxvirus include monkeypox, cowpox, Molluscum Contagiosum, camelpox, goatpox, swinepox, sheeppox, buffalopox, sealpox, canarypox, raccoonpox, pigeonpox and rabbitpox. Poxvirus further include live and attenuated pathogenic or non-pathogenic Vaccinia virus. Exemplary Vaccinia virus include vaccinia Ankara (MVA), vaccinia virus Lister strain, vaccinia virus Copenhagen strain, vaccinia virus Connaught strain, vaccinia virus Brighton strain, vaccinia virus LC16m8 strain, vaccinia virus LC16MO, vaccinia virus IHD-J, vaccinia virus Dairen I, vaccinia virus NYCBOH strain, vaccinia virus Wyeth strain, vaccinia virus Tian Tan, vaccinia virus LIVP, vaccinia virus L-IPV, vaccinia virus Dryvax® and ACAM1000.

Methods of the invention include methods of treatment that results in a beneficial effect. Particular non-limiting examples of beneficial effects include providing a subject with partial or complete protection against a poxvirus infection or pathogenesis, or a symptom caused by a poxvirus infection or pathogenesis (e.g., inhibit or reduce probability or susceptibility). Particular non-limiting examples of beneficial effects also include reducing, decreasing, inhibiting, delaying or preventing poxvirus infection or pathogenesis, and reducing, decreasing, inhibiting, ameliorating or preventing onset, severity, duration, progression, frequency or probability of one or more symptoms or pathologies associated with a poxvirus infection or pathogenesis. Additional non-limiting examples of beneficial effects also include reducing, decreasing, amounts of, or inhibiting, delaying or preventing increases in poxvirus titer or load, proliferation or replication. Further non-limiting particular examples of beneficial effects include reducing, decreasing, inhibiting, delaying, ameliorating or preventing onset, progression, severity, duration, frequency, probability or susceptibility of a subject to poxvirus infection or pathogenesis, or accelerating, facilitating or hastening recovery of a subject from poxvirus infection or pathogenesis or one or more associated symptoms or pathologies.

Methods of the invention therefore include providing a beneficial or therapeutic effect to a subject, for example, reducing, decreasing, inhibiting, delaying, ameliorating or preventing onset, progression, severity, duration, frequency or probability of poxvirus infection or pathogenesis or one or more symptoms or pathologies associated with or caused by poxvirus infection or pathogenesis; reducing, decreasing, inhibiting, delaying or preventing increases in poxvirus titer, load, replication, proliferation, or an amount of a viral protein of one or more poxvirus strains or isolates or subtypes. Stabilizing the infection, a symptom or pathology thereof, or preventing, inhibiting or delaying a worsening or progression of the infection or a symptom or pathology associated with or caused by poxvirus infection or pathogenesis, or progression of the underlying poxvirus infection, are also included in various embodiments of the methods of the invention.

Specific examples of symptoms and pathologies associated with or caused by poxvirus infection or pathogenesis, whose onset, progression, severity, frequency, duration or probability can be reduced, decreased inhibited, delayed ameliorated or prevented include, for example, high fever, muscle aches, fatigue, headache, backache, malaise, rash (maculopapular, vesicular or pustular), blisters, pustules or lesions, delirium, vomiting, diarrhea and excess bleeding. Other symptoms and pathologies of poxvirus infection or pathogenesis, are known in the art and treatment thereof in accordance with the invention is provided.

The methods of the invention, including, among other methods, providing a subject with protection against a poxvirus infection or pathogenesis, treatment of a poxvirus infection or pathogenesis, or a symptom or pathology associated with or caused by poxvirus infection or pathogenesis, or decreasing susceptibility of a subject to a poxvirus infection or pathogenesis, can therefore result in an improvement in the subjects' condition. An improvement is therefore any objective or subjective reduction, decrease, inhibition, delay, ameliorating or prevention of onset, progression, severity, duration, frequency or probability of one or more symptoms or pathologies associated with or caused by poxvirus infection or pathogenesis, or virus titer, load, replication, proliferation, or an amount of a viral protein. An improvement would also include reducing, inhibiting or preventing increases in virus titer, load, replication, proliferation, or an amount of a viral protein of one or more poxvirus strains or isolates or subtypes or species. An improvement would further include stabilizing a symptom or pathology associated with or caused by poxvirus infection or pathogenesis, or inhibiting, decreasing, delaying or preventing a worsening or progression of the symptom or pathology associated with or caused by poxvirus infection or pathogenesis, or progression of the underlying poxvirus infection. An improvement can therefore be, for example, in any of high fever, muscle aches, fatigue, headache, backache, malaise, rash, blisters, pustules, lesions, delirium, vomiting, diarrhea, excess bleeding and death to any degree or for any duration of time (hours, days, weeks, months, years, or cure).

An improvement would also include reducing or eliminating a need, dosage amount or frequency of another treatment, such as an antiviral drug or other agent used for treating a subject having or at risk of having a poxvirus infection or pathogenesis, a symptom or pathology associated with or caused by poxvirus infection or pathogenesis, or decreasing or preventing an adverse side effect caused by vaccination with or against a poxvirus. Thus, reducing an amount of another treatment for poxvirus infection or pathogenesis, a symptom or pathology associated with or caused by poxvirus, or an adverse side effect caused by vaccination with or against a poxvirus is considered to provide a benefit and, therefore, is considered within the invention methods. Non-limiting exemplary poxvirus treatments that may be eliminated or used at reduced doses or frequencies of administration include vaccinia immune globulin (VIG), cidofivir, or an antibody that binds to a poxvirus protein (e.g., a vaccinia virus protein). Additional non-limiting exemplary poxvirus treatments include vaccination, such as with an attenuated or live poxvirus, for example, modified vaccinia Ankara (MVA), vaccinia virus Lister strain, vaccinia virus LC16m8 strain, vaccinia virus NYCBOH strain, vaccinia virus Wyeth strain or vaccinia virus Dryvax®, or a, vaccinia virus protein used for immunization of a subject against poxvirus infection or pathogenesis.

A treatment or improvement need not be complete ablation of any particular infection, pathogenesis, symptom, pathology or adverse side effect, or all of the infection, pathology, symptoms, pathologies or adverse side effects associated with or caused by poxvirus infection or pathogenesis, or vaccination against a poxvirus. Rather, treatment may be any objective or subjective measurable or detectable anti-virus effect or improvement in a treated subject. Thus, reducing, inhibiting decreasing, eliminating, delaying, halting or preventing a progression or worsening of the infection or pathogenesis, a symptom or pathology of the infection or pathogenesis, or an adverse side effect caused by vaccination is a satisfactory outcome. For example, a compound of the invention (e.g., CSA) may reduce, delay or stabilize high fever, but not have any effect on fatigue, muscle aches, fatigue, headache, backache, malaise, rash, blisters, pustules, lesions, delirium, vomiting, diarrhea or excess bleeding. Another example is where a compound of the invention reduces fatigue, without a detectable improvement in or more other symptoms or pathologies. Thus, a satisfactory clinical endpoint is achieved when there is an incremental improvement in the subject's condition or a partial reduction or a stabilization of a poxvirus infection, pathogenesis or a symptom, pathology or adverse side effect thereof, or an inhibition or prevention of worsening or progression of the poxvirus infection, pathogenesis, symptom, pathology or adverse side effect thereof (stabilizing one or more symptoms or pathologies), over a short or long duration (hours, days, weeks, months, years, or cure).

In the methods of the invention in which there is a desired outcome, for example, a therapeutic or prophylactic method that provides an objective or subjective improvement in a poxvirus infection or pathogenesis, a symptom or pathology associated with or caused by poxvirus, or an adverse side effect caused by vaccination with or against a poxvirus, a compound of the invention (e.g., CSA) can be administered in a sufficient or effective amount. As used herein, a "sufficient amount" or "effective amount" or an "amount sufficient" or an "amount effective" refers to an amount that provides, in single or multiple doses, alone or in combination with one or more other compounds, treatments, agents (e.g., a drug) or therapeutic regimens, a long term or a short term detectable or measurable improvement or beneficial effect to a given subject of any degree or for any time period or duration (e.g., for minutes, hours, days, months, years, or cured).

A "sufficient amount" or "effective amount" therefore includes decreasing, reducing, inhibiting, preventing, or delaying onset; decreasing, reducing, inhibiting, delaying, or preventing a progression or worsening of; or reducing, relieving, ameliorating, or alleviating, severity, frequency, duration, susceptibility or probability of poxvirus infection or pathogenesis, one or more symptoms associated with or caused by poxvirus infection or pathogenesis, or an adverse side effect of vaccination with or against a poxvirus. In addition, hastening a subject's recovery poxvirus infection or pathogenesis, one or more symptoms associated with or caused by poxvirus infection or pathogenesis, or an adverse side effect of vaccination with or against a poxvirus is considered to be a sufficient or effective amount. Various beneficial effects and indicia of therapeutic and prophylactic benefit are as set forth herein and are known to the skilled artisan.

A sufficient amount or an effective amount can but need not be provided in a single administration and can but need not be administered alone (i.e., without a second drug, agent, treatment or therapeutic regimen), or in combination with another compound, agent, treatment or therapeutic regimen. In addition, a sufficient amount or an effective amount need not be sufficient or effective if given in single or multiple doses without a second compound, treatment, agent, or therapeutic regimen, since additional doses, amounts, frequency or duration of administration above and beyond such doses, or additional compounds, agents, treatments or therapeutic regimens may be included in order to be effective or sufficient in a given subject.

A sufficient amount or an effective amount need not be effective in each and every subject, nor a majority of subjects in a given group or population. Thus, a sufficient amount or an effective amount means sufficiency or effectiveness in a particular subject, not a group or the general population. As is typical for such methods, some subjects will exhibit a greater or less response to a method of the invention than other subjects.

Amounts, frequencies or duration also considered sufficient and effective and are therefore beneficial are those that result in the elimination or a reduction in amount, frequency or duration of another compound, agent, treatment or therapeutic regimen. For example, a compound of the invention is considered as having a beneficial or therapeutic effect if contact, administration or delivery in vivo results in the use of a lesser amount, frequency or duration of another compound, agent, treatment or therapeutic regimen to treat the infection, pathogenesis, symptom or pathology, or adverse side effect of vaccination.

Any compound, agent, treatment or other therapeutic regimen having a beneficial, additive, synergistic or complementary activity or effect can be formulated or used in combination with or in addition to the invention compounds (e.g., CSAs). In various embodiments, the compound, agent, treatment or therapeutic regimen is for providing a subject with protection against a poxvirus infection or pathogenesis; treating a subject for poxvirus infection or pathogenesis; decreasing susceptibility of a subject to a poxvirus infection or pathogenesis; or decreasing or preventing an adverse side effect caused by poxvirus vaccination. Thus, compositions of the invention include CSA combinations with other CSAs, CSA combinations with other agents or treatments (e.g., anti-poxvirus drugs, such as cidofivir, poxvirus vaccines, poxvirus proteins, poxvirus antibodies, VIG, etc.), and methods of the invention include contact with, administration in vitro or in vivo, with another compound (e.g., another CSA), agent, treatment or therapeutic regimen appropriate for the condition to be treated. The compound (e.g., another CSA), agent, treatment or therapeutic regimen appropriate may be used in accordance with the prophylactic and therapeutic treatment methods, as well as methods for decreasing or preventing an adverse side effect caused by poxvirus vaccination, as set forth herein, prior to, concurrently or following contacting or administering a compound of the invention (e.g., CSA) in vitro or in vivo.

Examples of such combination compositions and methods include VIG and cidofivir. Additional non-limiting combination compositions and methods include poxvirus vaccination, such as with an attenuated or live poxvirus, for example, modified vaccinia Ankara (MVA), vaccinia virus Lister strain, vaccinia virus LC16m8 strain, vaccinia virus NYCBOH strain, vaccinia virus Wyeth strain or vaccinia virus Dryvax®, or a vaccinia virus protein used for immunization of a subject against poxvirus infection or pathogenesis. Further combination compositions and methods include poxvirus protein or antibody that binds to a poxvirus proteins (e.g., a vaccinia virus protein). A pool of poxvirus proteins or poxvirus binding antibodies (e.g., monoclonal or polyclonal) can be combined with a compound of the invention or administered separately (prior to, concurrently with or following) administration of a compound in accordance with the invention. In particular embodiments, an additional poxvirus protein is present on one or more of intracellular mature virion (IMV), cell-associated enveloped virion (CEV) or extracellular enveloped virion (EEV) forms of smallpox. In additional particular aspects, an additional poxvirus protein is one or more of vaccinia B5R, L1R, D8L, A33R, A27L, A17L, L5, A21, H2, A28, A14, A56, A34, A36, A2, or a B5R, L1R, D8L, A27L, A17L, L5, A21, H2, A28, A14, A56, A34, A36, or A2 homolog. In further particular embodiments, an additional antibody binds to a poxvirus protein present on one or more of intracellular mature virion (IMV), cell-associated enveloped virion (CEV) or extracellular enveloped virion (EEV) forms of smallpox. In still further particular embodiments, an additional antibody binds to a poxvirus protein, such as vaccinia protein B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog.

Antibodies include proteins that bind to other molecules (antigens) via heavy and light chain variable domains, $V_H$ and $V_L$, respectively. An antibody is any polyclonal or monoclonal immunoglobulin molecule, or mixture thereof, such as IgM, IgG, IgA, IgE, IgD, and any subclass thereof, such as $IgG_1$, $IgG_2$, $IgG_3$, $IgG_4$, etc. A monoclonal antibody, refers to an antibody that is based upon, obtained from or derived from a single clone, including any eukaryotic, prokaryotic, or phage clone. An antibody also includes a functional (e.g., binding) fragment or subsequence, such as, for example, Fab, Fab', F(ab')$_2$, Fv, Fd, scFv and sdFv, unless otherwise expressly stated.

Antibodies include those specific or selective for binding to poxvirus protein or a homolog. That is, binding to proteins other than the poxvirus protein or a homolog is such that the binding does not significantly interfere with detection of the poxvirus protein or homolog, unless such other proteins have a similar or same epitope the poxvirus protein or homolog that is recognized by the poxvirus antibody. Selective binding can be distinguished from non-selective binding using specificity, affinity and other binding assays, competitive and non-competitive, known in the art.

Antibodies include "human" forms, which mean that the amino acid sequence of the antibody is fully human or can or do exist in a human antibody. An antibody that is non-human may be made fully human by substituting non-human amino acid residues with amino acid residues that can or do exist in a human antibody. Amino acid residues present in human antibodies, CDR region maps and human antibody consensus residues are known in the art (see, e.g., Kabat, *Sequences of Proteins of Immunological Interest*, 4$^{th}$ Ed. US Department of Health and Human Services. Public Health Service (1987); Chothia and Lesk *J. Mol. Biol.* 186:651 (1987); Padlan *Mol. Immunol.* 31:169 (1994); and Padlan *Mol. Immunol.* 28:489 (1991)).

Antibodies include "human" forms, which means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Antibodies referred to as "primatized" in the art are within the meaning of "humanized" as used herein, except that the acceptor human immunoglobulin molecule and framework region amino acid residues may be any primate amino acid residue (e.g., ape, gibbon, gorilla, chimpanzees orangutan, macaque), in addition to any human residue.

Antibodies include "chimeric" forms, which means that the amino acid sequence of the antibody contains one or more portions that are derived from, obtained or isolated from, or based upon two or more different species. That is, for example, a portion of the antibody may be human (e.g., a constant region) and another portion of the antibody may be non-human (e.g., a murine heavy or light chain variable region). Thus, a chimeric antibody is a molecule in which different portions of the antibody are of different species origins. Unlike a humanized antibody, a chimeric antibody can have the different species sequences in any region of the antibody.

The term "subject" refers to an animal, typically mammalian animals, such as but not limited to non-human primates (apes, gibbons, gorillas, chimpanzees, orangutans, macaques), domestic animals (dogs and cats), a farm animals (chickens, ducks, horses, cows, goats, sheep, pigs), experimental animal (mouse, rat, rabbit, guinea pig) and humans. Subjects include animal models, for example, a mouse model of poxvirus infection (e.g., vaccinia virus). Subjects include naturally occurring or non-naturally occurring mutated or non-human genetically engineered (e.g., transgenic or knockout) animals. Subjects further include animals having or at risk of having a chronic or acute poxvirus infection or pathogenesis, symptom of poxvirus infection or pathogenesis, or adverse side effect caused by vaccination with or against poxvirus. Subjects can be any age. For example, a subject (e.g., human) can be a newborn, infant, toddler, child, teenager, or adult, e.g., 50 years or older.

Subjects include those in need of a method of the invention, e.g., in need of a therapeutic or prophylactic treatment. A subject is considered to be in need of a method of the invention where a method is likely to provide some benefit to a subject. Various benefits provided to a subject are as set forth herein and known in the art for poxvirus infection, pathogenesis, symptoms or pathologies caused by or associated with poxvirus infection or pathogenesis, and adverse side effects caused by vaccination with or against a poxvirus.

Subjects appropriate for treatment include those having poxvirus infection or pathogenesis or having any symptom or pathology associated with or caused by poxvirus. Target subjects therefore include subjects that have been infected with poxvirus, or that have developed one or more adverse symptoms or pathologies associated with or caused by poxvirus infection or pathogenesis, regardless of the virus type, timing or degree of onset, progression, severity, frequency, duration of any infection, pathogenesis, symptom, pathology or adverse side effect.

Subjects appropriate for treatment also include those at risk of poxvirus infection or pathogenesis or at risk of having or developing a poxvirus infection. Candidate subjects therefore include subjects that have been exposed to or contacted with poxvirus, or that are at risk of exposure to or contact with poxvirus, regardless of the type, timing or extent of exposure or contact. The invention methods are therefore applicable to a subject who is at risk of poxvirus infection or pathogenesis, but has not yet been exposed to or contacted with poxvirus. Prophylactic methods are therefore included. Subjects targeted for prophylaxis can be at increased risk (probability or susceptibility) of poxvirus infection or pathogenesis, as set forth herein and known in the art.

At risk subjects appropriate for treatment include subjects exposed to other subjects having a poxvirus, or where the risk of poxvirus infection is increased due to changes in virus infectivity or cell tropism, immunological susceptibility (e.g., an immunocompromised subject), or environmental risk. At risk subjects appropriate for treatment therefore include human subjects exposed to or at risk of exposure to other humans that have a poxvirus infection, or are at risk of a poxvirus infection in the environment.

Subjects also appropriate for treatment also include those vaccinated against or a candidate for vaccination against poxvirus (e.g., vaccinated with live or attenuated Vaccinia virus). Subjects therefore include vaccinated subjects that have not or have been exposed to or contacted with poxvirus, as well as candidate subjects for vaccination that have not or have been exposed to or contacted with poxvirus, regardless of the type, timing or extent of exposure or contact.

In various embodiments, a subject has or is a candidate for vaccination with a live or attenuated Vaccinia virus. In various aspects, the subject is a candidate for or has been vaccinated with a modified vaccinia Ankara (MVA), vaccinia virus Lister strain, vaccinia virus LC16m8 strain, vaccinia virus NYCBOH strain, vaccinia virus Wyeth strain, vaccinia virus Dryvax® or ACAM1000. In further aspects, a subject is administered a compound of the invention (e.g., CSA) prior to, concurrently with, or following vaccination (e.g., within 0-2, 2-4, 4-12 or 12-24 hours or days of vaccination).

Subjects further include immunocompromised subjects due to an immunological disorder (e.g., autoimmunity) or disease, or an immune-suppressing treatment (e.g., cyclophosphamide). Subjects also include those having been exposed to or diagnosed as HIV+. Subjects further include those receiving or candidates for a tissue or organ transplant.

Compounds of the invention, including CSAs, can be incorporated into pharmaceutical compositions or formulations. Such pharmaceutical compositions/formulations are useful for administration to a subject, in vivo or ex vivo.

Pharmaceutical compositions and formulations include carriers or excipients for administration to a subject. As used herein the terms "pharmaceutically acceptable" and "physiologically acceptable" mean a biologically compatible formulation, gaseous, liquid or solid, or mixture thereof, which is suitable for one or more routes of administration, in vivo delivery or contact. A formulation is compatible in that it does not destroy activity of an active ingredient therein (e.g., a CSA), or induce adverse side effects that far outweigh any prophylactic or therapeutic effect or benefit.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

The formulations may, for convenience, be prepared or provided as a unit dosage form. Preparation techniques include bringing into association the active ingredient (e.g., CSA) and a pharmaceutical carrier(s) or excipient(s). In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., a CSA) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., CSA) moistened with an inert liquid diluent. The tablets may optionally be coated or scored and may be formulated so as to provide a slow or controlled release of the active ingredient therein.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Supplementary active compounds (e.g., preservatives, antioxidants, antimicrobial agents including biocides and biostats such as antibacterial, antiviral and antifungal agents) can also be incorporated into the compositions. Preservatives and other additives include, for example, antimicrobials, antioxidants, chelating agents and inert gases (e.g., nitrogen). Pharmaceutical compositions may therefore include preservatives, antimicrobial agents, anti-oxidants, chelating agents and inert gases.

Preservatives can be used to inhibit microbial growth or increase stability of the active ingredient thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include, antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include those set forth above and, nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, valacyclovir, ganciclovir, 1, -D-ribofuranosyl-1,2,4-triazole-3 carboxamide, 9->2-hydroxy-ethoxy methylguanine, adamantanamine, 5-iodo-2'-deoxyuridine, trifluorothymidine, interferon and adenine arabinoside.

Exemplary antifungals include agents such as benzoic acid, undecylenic alkanolamide, ciclopiroxolamine, polyenes, imidazoles, allylamine, thicarbamates, amphotericin B, butylparaben, clindamycin, econaxole, amrolfine, butenafine, naftifine, terbinafine, ketoconazole, elubiol, econazole, econaxole, itraconazole, isoconazole, miconazole, sulconazole, clotrimazole, enilconazole, oxiconazole, tioconazole, terconazole, butoconazole, thiabendazole, voriconazole, saperconazole, sertaconazole, fenticonazole, posaconazole, bifonazole, fluconazole, flutrimazole, nystatin, pimaricin, amphotericin B, flucytosine, natamycin, tolnaftate, mafenide, dapsone, caspofungin, actofunicone, griseofulvin, potassium iodide, Gentian Violet, ciclopirox, ciclopirox olamine, haloprogin, ketoconazole, undecylenate, silver sulfadiazine, undecylenic acid, undecylenic alkanolamide and Carbol-Fuchsin.

Pharmaceutical compositions can optionally be formulated to be compatible with a particular route of administration. Thus, pharmaceutical compositions include carriers (excipients, diluents, vehicles or filling agents) suitable for administration by various routes and delivery, locally, regionally or systemically.

Exemplary routes of administration for contact or in vivo delivery which a compound of the invention (e.g., CSA) can optionally be formulated include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, intralymphatic.

Formulations suitable for parenteral administration include aqueous and non-aqueous solutions, suspensions or emulsions of the compound, which may include suspending agents and thickening agents, which preparations are typically sterile and can be isotonic with the blood of the intended recipient. Non-limiting illustrative examples of aqueous carriers include water, saline (sodium chloride solution), dextrose (e.g., Ringer's dextrose), lactated Ringer's, fructose, ethanol, animal, vegetable or synthetic oils. Examples of non-aqueous solvents are propylene glycol, polyethylene glycol, vegetable oils such as olive oil, and injectable organic esters such as ethyl oleate. Intravenous vehicles include fluid and nutrient replenishers, electrolyte replenishers (such as those based on Ringer's dextrose). The formulations may be presented in unit-dose or multi-dose kits, for example, ampules and vials, and may be stored in a freeze-dried (lyophilized) condition requiring addition of a sterile liquid carrier, for example, water for injections, prior to use.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, pastes, lotions, oils or creams as generally known in the art.

For topical administration, for example, to skin, pharmaceutical compositions typically include ointments, creams, lotions, pastes, gels, sprays, aerosols or oils. Carriers which may be used include Vaseline, lanolin, polyethylene glycols, alcohols, transdermal enhancers, and combinations thereof. An exemplary topical delivery system is a transdermal patch containing an active ingredient (e.g., CSA).

For oral administration, pharmaceutical compositions include capsules, cachets, lozenges, tablets or troches, as powder or granules. Oral administration formulations also include a solution or a suspension (e.g., aqueous liquid or a non-aqueous liquid; or as an oil-in-water liquid emulsion or a water-in-oil emulsion).

For airway or nasal administration, pharmaceutical compositions can be formulated in a dry powder for delivery, such as a fine or a coarse powder having a particle size, for example, in the range of 20 to 500 microns which is administered in the manner by inhalation through the airways or nasal passage. Depending on delivery device efficiency, effective dry powder dosage levels typically fall in the range of about 10 to about 100 mg. Appropriate formulations, wherein the carrier is a liquid, for administration, as for example, a nasal spray or as nasal drops, include aqueous or oily solutions of the active ingredient.

For airway or nasal administration, aerosol and spray delivery systems and devices, also referred to as "aerosol generators" and "spray generators," such as metered dose inhalers (MDI), nebulizers (ultrasonic, electronic and other nebulizers), nasal sprayers and dry powder inhalers can be used. MDIs typically include an actuator, a metering valve, and a container that holds a suspension or solution, propellant, and surfactant (e.g., oleic acid, sorbitan trioleate, lecithin). Activation of the actuator causes a predetermined amount to be dispensed from the container in the form of an aerosol, which is inhaled by the subject. MDIs typically use liquid propellant and typically, MDIs create droplets that are 15 to 30 microns in diameter, optimized to deliver doses of 1 microgram to 10 mg of a therapeutic. Nebulizers are devices that turn medication into a fine mist inhalable by a subject through a face mask that covers the mouth and nose. Nebulizers provide small droplets and high mass output for delivery to upper and lower respiratory airways. Typically, nebulizers create droplets down to about 1 micron in diameter.

Dry-powder inhalers (DPI) can be used to deliver the compounds of the invention, either alone or in combination with a pharmaceutically acceptable carrier. DPIs deliver active ingredient to airways and lungs while the subject inhales through the device. DPIs typically do not contain propellants or other ingredients, only medication, but may optionally include other components. DPIs are typically breath-activated, but may involve air or gas pressure to assist delivery.

For rectal administration, pharmaceutical compositions can be included as a suppository with a suitable base comprising, for example, cocoa butter or a salicylate. For vaginal administration, pharmaceutical compositions can be included as pessaries, tampons, creams, gels, pastes, foams or spray formulations containing in addition to the active ingredient (e.g., CSA) a carrier, examples of appropriate carriers which are known in the art.

Pharmaceutical formulations and delivery systems appropriate for the compositions and methods of the invention are known in the art (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; *Ansel* and *Stoklosa, Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

Compounds of the invention (e.g., CSAs), including pharmaceutical formulations can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (excipient, diluent, vehicle or filling agent) which, when administered in one or more doses, is calculated to produce a desired effect (e.g., prophylactic or therapeutic effect or benefit). Unit dosage forms can contain a daily dose or unit, daily sub-dose, or an appropriate fraction thereof, of an administered compound (e.g., CSA). Unit dosage forms also include, for example, capsules, troches, cachets, lozenges, tablets, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Compounds of the invention (e.g., CSAs) can be administered in accordance with the methods at any frequency as a single bolus or multiple dose e.g., one, two, three, four, five, or more times hourly, daily, weekly, monthly or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect of poxvirus infection, pathogenesis or vaccination.

Doses may vary depending upon whether the treatment is therapeutic or prophylactic, the onset, progression, severity, frequency, duration, probability of or susceptibility of the symptom, the type of virus infection or pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit.

Typically, for therapeutic treatment, a compound of the invention (e.g., CSA) will be administered as soon as practical, typically within 0-72 hours after a subject is exposed to or contacted with any poxvirus, or within 0-72 hours after development of one or more symptoms or pathologies associated with poxvirus infection or pathogenesis (e.g., onset of fever, rash, lesions, etc.) or a symptom associated with pathogenic poxviruses such as smallpox and monkeypox.

For prophylactic treatment, a compound of the invention can be administered immediately or within 0-72 after suspected contact with, or 0-4 weeks, e.g., 1-3 weeks, prior to anticipated or possible exposure to or contact with poxvirus. For prophylactic treatment in connection with immunization/ vaccination of a subject, a compound can be administered prior to, concurrently with or following immunization/vaccination of the subject.

Doses can be based upon current existing active or passive immunization protocols (e.g., VIG), empirically determined, determined using animal disease models or optionally in human clinical studies. For example, initial study doses can be based upon animal studies, such as a mouse, which weighs about 30 grams, and the amount of compound administered to achieve a prophylactic or therapeutic effect or benefit. The dose can be adjusted according to the mass of a subject, and will generally be in a range from about 0.1-1 ug/kg, 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, or more, of subject body weight, two, three, four, or more times per hour, day, week, month or annually. Of course, doses can be more or less, as appropriate, for example, 0.00001 mg/kg of subject body weight to about 10,000.0 mg/kg of subject body weight, about 0.001 mg/kg, to about 100 mg/kg, about 0.01 mg/kg, to about 10 mg/kg, or about 0.1 mg/kg, to about 1 mg/kg of subject body weight over a given time period, e.g., 1, 2, 3, 4, 5 or more hours, days, weeks, months, years. A subject may be administered in single bolus or in divided/metered doses, which can be adjusted to be more or less according to the various consideration set forth herein and known in the art.

Dose amount, frequency or duration may be increased or reduced, as indicated by the status of the poxvirus infection or pathogenesis, associated symptom or pathology, or any adverse side effect(s) of vaccination, treatment or anti-poxvirus therapy. For example, once control or a particular endpoint is achieved, for example, reducing, decreasing, inhibiting, ameliorating or preventing onset, severity, duration, progression, frequency or probability of one or more symptoms associated with a poxvirus infection or pathogenesis of one or more symptoms or pathologies associated with or caused by poxvirus infection or pathogenesis, dose amount, frequency or duration can be reduced.

The invention provides kits including compounds of the invention (e.g., CSA), combination compositions and pharmaceutical compositions/formulations thereof, packaged into a suitable packaging material. In one embodiment, a kit includes packaging material, a cationic steroid antimicrobial (CSA) and instructions. In various aspects, the instructions are for administering the CSA to: provide a subject with protection against a poxvirus infection or pathogenesis; treat a subject for poxvirus infection or pathogenesis; decrease susceptibility of a subject to a poxvirus infection or pathogenesis; or decrease or prevent an adverse side effect caused by vaccination of a subject with a poxvirus.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more compounds of the invention alone or in combination with an anti-poxvirus agent or treatment (e.g., an antiviral, a poxvirus protein or an antibody that binds to a poxvirus protein) or drug, optionally sterile.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacturer location and date, expiration dates.

Labels or inserts can include information on a condition, disorder or disease (e.g., virus pathogenesis or infection) for which a kit component may be used. Labels or inserts can include instructions for a clinician or subject for using one or more of the kit components in a method, treatment protocol or therapeutic/prophylactic regimen, including the methods of the invention. Instructions can include amounts of compound, frequency or duration of administration, and instructions for practicing any of the methods, treatment protocols or prophylactic or therapeutic regimes described herein. Exemplary instructions include, instructions for treating poxvirus infection or pathogenesis. Kits of the invention therefore can additionally include labels or instructions for practicing any of the methods of the invention described herein including treatment, screening or other methods. Thus, for example, a kit can include a compound of the invention (e.g., CSA) that has one or more anti-poxvirus activities as set forth herein, together with instructions for administering the compound in a prophylactic or therapeutic treatment method of the invention, for example to a subject in need of such treatment. Exemplary instructions include administering the CSA to: provide a subject with protection against a poxvirus infection or pathogenesis; treat a subject for poxvirus infection or pathogenesis; decrease susceptibility of a subject to a poxvirus infection or pathogenesis; or decrease or prevent an adverse side effect caused by vaccination of a subject with a poxvirus.

Labels or inserts can include information on any effect or benefit a kit component may provide, such as a prophylactic or therapeutic effect or benefit. For example, a label or insert could provide a description of one or more symptoms which can be improved, i.e., reducing, decreasing, inhibiting, ameliorating or preventing onset, severity, duration, progression, frequency or probability of one or more symptoms or pathologies associated with a poxvirus infection or pathogenesis, or one or more adverse side effects associated with poxvirus vaccination. Poxvirus symptoms and pathologies are as set forth herein or known in the art (e.g., high fever, muscle aches, fatigue, headache, backache, malaise, rash, blisters, pustules, lesions, delirium, vomiting, diarrhea, excess bleeding, death, etc.). Adverse side effects associated with poxvirus vaccination are as set forth herein or known in the art (e.g., postvaccinial encephalitis, progressive vaccinia-Vaccinia necrosum, eczema vaccinatum, Vaccinia Keratitis, generalized vaccinia, myopericarditis, inoculation of other sites, infection of close contacts, rash and periocular infection, death, etc.)

Labels or inserts can include information on potential adverse side effects of treatment. Labels or inserts can further include warnings to the clinician or subject regarding situations or conditions where a subject should stop or reduce use of a particular kit component. Adverse side effects could also occur when the subject has, will be or is currently taking one or more other medications that may be incompatible with a compound of the invention, or the subject has, will be or is currently undergoing another treatment protocol or therapeutic regimen which would be incompatible with the compound and, therefore, labels or inserts could include information regarding such side effects or incompatibilities.

Invention kits can additionally include a buffering agent, or a preservative or a stabilizing agent in a pharmaceutical formulation containing a compound of the invention. Each component of the kit can be enclosed within an individual container and all of the various containers can be within a single package. Invention kits can be designed for cold storage.

Invention kits can include components, such as devices for practicing a method of the invention or administering a compound of the invention (e.g., CSA) to a subject, ex vivo or in vivo. The device can be a delivery device, such as a syringe, a compressible (e.g., squeezable) tube or dermal patch for mucosal, skin/dermis or corneal delivery, or an aerosol delivery device for administration to lungs or airways.

Compounds useful in accordance with the invention, are described herein, both generically and with particularity, and in U.S. Pat. Nos. 6,350,738; 6,486,148; and 6,767,904, which are incorporated herein by reference. Compounds include steroid derivatives, such as cationic steroid antimicrobials (CSA) that exhibit one or more anti-poxvirus activities or functions. The skilled artisan will recognize the compounds within the generic formula set forth herein. Additional compounds of the invention having one or more anti-poxvirus activities or functions are described and can be characterized using the assays set forth herein and in the art.

Compounds of formula I, also referred to as cationic steroid antimicrobials (CSA), comprise:

I 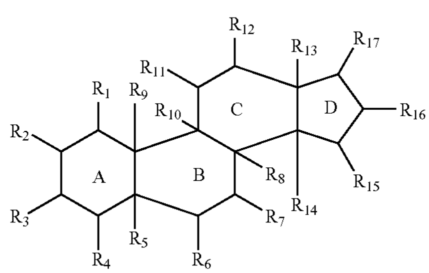 wherein:

fused rings A, B, C, and D are independently saturated or fully or partially unsaturated; and each of $R_1$ through $R_4$, $R_6$, $R_7$, $R_{11}$, $R_{12}$, $R_{15}$, $R_{16}$, and $R_{17}$ is independently selected from the group consisting of hydrogen, hydroxyl, a substituted or unsubstituted (C1-C10) alkyl, (C1-C10) hydroxyalkyl, (C1-C10) alkyloxy-(C1-C10) alkyl, (C1-C10) alkylcarboxy-(C1-C10) alkyl, (C1-C10) alkylamino-(C1-C10) alkyl, (C1-C10) alkylamino-(C1-C10) alkylamino, (C1-C10) alkylamino-(C1-C10) alkylamino-(C1-C10) alkylamino, a substituted or unsubstituted (C1-C10) aminoalkyl, a substituted or unsubstituted aryl, a substituted or unsubstituted arylamino-(C1-C10) alkyl, (C1-C10) haloalkyl, C2-C6 alkenyl, C2-C6 alkynyl, oxo, a linking group attached to a second steroid, a substituted or unsubstituted (C1-C10) aminoalkyloxy, a substituted or unsubstituted (C1-C10) aminoalkyloxy-(C1-C10) alkyl, a substituted or unsubstituted (C1-C10) aminoalkylcarboxy, a substituted or unsubstituted (C1-C10) aminoalkylaminocarbonyl, a substituted or unsubstituted (C1-C10) aminoalkylcarboxamido, $H_2N$—HC(Q5)-C(O)—O—, H2N—HC(Q5)-C(O)—N(H)—, (C1-C10) azidoalkyloxy, (C1-C10) cyanoalkyloxy, P.G.-HN—HC(Q5)-C(O)—O—, (C1-C10) guanidinoalkyl oxy, (C1-C10) quaternaryammoniumalkylcarboxy, and (C1-C10) guanidinoalkyl carboxy, where Q5 is a side chain of any amino acid (including the side chain of glycine, i.e., H), P.G. is an amino protecting group, and $R_5$, $R_8$, $R_9$, $R_{10}$, $R_{13}$, and $R_{14}$ is each independently: deleted when one of fused rings A, B, C, or D is unsaturated so as to complete the valency of the carbon atom at that site, or selected from the group consisting of hydrogen, hydroxyl, a substituted or unsubstituted (C1-C10) alkyl, (C1-C10) hydroxyalkyl, (C1-C10) alkyloxy-(C1-C10) alkyl, a substituted or unsubstituted (C1-C10) aminoalkyl, a substituted or unsubstituted aryl, C1-C10 haloalkyl, C2-C6 alkenyl, C2-C6 alkynyl, oxo, a linking group attached to a second steroid, a substituted or unsubstituted (C1-C10) aminoalkyloxy, a substituted or unsubstituted (C1-C10) aminoalkylcarboxy, a substituted or unsubstituted (C1-C10) aminoalkylaminocarbonyl, H2N—HC(Q5)-C(O)—O—, H2N—HC(Q5)-C(O)—N(H)—, (C1-C10) azidoalkyloxy, (C1-C10) cyanoalkyloxy, P.G.-HN—HC(Q5)-C(O)—O—, (C1-C10) guanidinoalkyloxy, and (C1-C10) guanidinoalkylcarboxy, where Q5 is a side chain of any amino acid, P.G. is an amino protecting group, and provided that at least two of $R_1$ through $R_{14}$ are independently selected from the group consisting of a substituted or unsubstituted (C1-C10) aminoalkyloxy, (C1-C10) alkylcarboxy-(C1-C10) alkyl, (C1-C10) alkylamino-(C1-C10) alkylamino, (C1-C10) alkylamino-(C1-C10) alkylamino-(C1-C10) alkylamino, a substituted or unsubstituted (C1-C10) aminoalkylcarboxy, a substituted or unsubstituted arylamino-(C1-C10) alkyl, a substituted or unsubstituted (C1-C10) aminoalkyloxy-(C1-C10) alkyl, a substituted or unsubstituted (C1-C10) aminoalkylaminocarbonyl, (C1-C10) quaternaryammonium alkylcarboxy, H2N—HC(Q5)-C(O)—O—, H2N—HC(Q5)-C(O)—N(H)—, (C1-C10) azidoalkyloxy, (C1-C10) cyanoalkyloxy, P.G.-HN—HC(Q5)-C(O)—O—, (C1-C10) guanidinoalkyloxy, and (C1-C10) guanidinoalkylcarboxy; or a pharmaceutically acceptable salt thereof.

A "ring" as used herein can be heterocyclic or carbocyclic. The term "saturated" used herein refers to the fused ring of formula I having each atom in the fused ring either hydrogenated or substituted such that the valency of each atom is filled. The term "unsaturated" used herein refers to the fused ring of formula I where the valency of each atom of the fused ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$; $R_8$ and $R_{10}$; and $R_{13}$ and $R_{14}$.

The term "unsubstituted" used herein refers to a moiety having each atom hydrogenated such that the valency of each atom is filled.

The term "halo" used herein refers to a halogen atom such as fluorine, chlorine, bromine, or iodine.

Examples of amino acid side chains include but are not limited to H (glycine), methyl (alanine), $—CH_2—(C{=}O)—NH_2$ (asparagine), $—CH_2—SH$ (cysteine), and $—CH(OH)CH_3$ (threonine).

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. Substituted alkyl groups may have one, two, three or more substituents, which may be the same or different, each replacing a hydrogen atom. Substituents are halogen (e.g., F, Cl, Br, and I), hydroxyl, protected hydroxyl, amino, protected amino, carboxy, protected carboxy, cyano, methylsulfonylamino, alkoxy, acyloxy, nitro, and lower haloalkyl.

The term "substituted" used herein refers to moieties having one, two, three or more substituents, which may be the same or different, each replacing a hydrogen atom. Examples of substituents include but are not limited to halogen (e.g., F, Cl, Br, and I), hydroxyl, protected hydroxyl, amino, protected amino, carboxy, protected carboxy, cyano, methylsulfonylamino, alkoxy, alkyl, aryl, aralkyl, acyloxy, nitro, and lower haloalkyl.

An aryl group is a C6-20 aromatic ring, wherein the ring is made of carbon atoms (e.g., C6-C14, C6-10 aryl groups). Examples of haloalkyl include fluoromethyl, dichloromethyl, trifluoromethyl, 1,1-difluoroethyl, and 2,2-dibromoethyl.

An aralkyl group is a group containing 6-20 carbon atoms that has at least one aryl ring and at least one alkyl or alkylene chain connected to that ring. An example of an aralkyl group is a benzyl group.

A linking group is any divalent moiety used to link a compound of formula to another steroid, e.g., a second compound of formula I. An example of a linking group is (C1-C10) alkyloxy-(C1-C10) alkyl.

Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the invention. Further examples and conditions are found in T. W. Greene, Protective Groups in Organic Chemistry, (1st ed., 1981, 2nd ed., 1991).

The invention also includes compounds comprising a ring system of at least 4 fused rings, where each of the rings has from 5-7 atoms. The ring system has two faces, and contains 3 chains attached to the same face. Each of the chains contains a nitrogen-containing group that is separated from the ring system by at least one atom; the nitrogen-containing group is an amino group, e.g., a primary amino group, or a guanidino group. The compound can also contain a hydrophobic group, such as a substituted (C3-10) aminoalkyl group, a (C1-10) alkyloxy (C3-10) alkyl group, or a (C1-10) alkylamino (C3-10)alkyl group, attached to the steroid backbone.

For example, the compound may have the formula V, where each of the three chains 10 containing nitrogen-containing groups is independently selected from $R_1$ through $R_4$, $R_6$, $R_7$, $R_{11}$, $R_{12}$, $R_{15}$, $R_{16}$, $R_{17}$, and $R_{18}$, defined below.

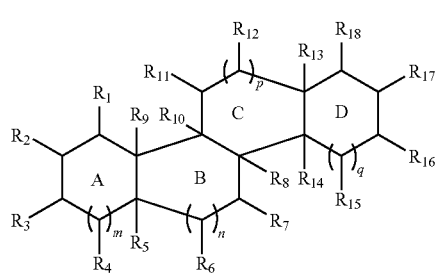

V where:

each of fused rings A, B, C, and D is independently saturated, or is fully or partially unsaturated, provided that at least two of A, B, C, and D are saturated, wherein rings A, B, C, and D form a ring system;

each of m, n, p, and q is independently 0 or 1;

each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted (C1-C10) alkyl, (C1-C10) hydroxyalkyl, (C1-C10) alkyloxy-(C1-C10) alkyl, (C1-C10)alkylcarboxy-(C1-C10 alkyl, (C1-C10) alkylamino-(C1-C10) alkyl, (C1-C10) alkylamino-(C1-C10) alkylamino, (C1-C10 alkylamino-(C1-C10) alkylamino-(C1-C10) alkylamino, a substituted or unsubstituted (C1-C10) aminoalkyl, a substituted or unsubstituted aryl, a substituted or unsubstituted arylamino-(C1-C10) alkyl, (C1-C10) haloalkyl, C2-C6 alkenyl, C2-C6 alkynyl, oxo, a linking group attached to a second steroid, a substituted or unsubstituted (C1-C10) aminoalkyloxy, a substituted or unsubstituted (C1-C10) aminoalkyloxy-(C1-C10) alkyl, a substituted or unsubstituted (C1-C10) aminoalkylcarboxy, a substituted or unsubstituted (C1-C10) aminoalkylaminocarbonyl, a substituted or unsubstituted (C1-C10) aminoalkylcarboxamido, $H_2N$—HC(Q5)-C(O)—O—, $H_2N$—HC(Q5)-C(O)—N(H)—, (C1-C10) azidoalkyloxy, (C1-C10) cyanoalkyloxy, P.G.-HN—HC(Q5)-C(O)—O—, (C1-C10) guanidinoalkyloxy, (C1-C10) quaternaryammoniumalkylcarboxy, and (C1-C10) guanidinoalkyl carboxy, where Q5 is a side chain of any amino acid (including a side chain of glycine, i.e., H). P.G. is an amino protecting group: and each of $R_5$, $R_8$, $R_9$, $R_{10}$, $R_{13}$, and $R_{14}$ is independently: deleted when one of fused rings A, B, C, or D is unsaturated so as to complete the valency of the carbon atom at that site, or selected from the group consisting of hydrogen, hydroxyl, a substituted or unsubstituted (C1-C10) alkyl, (C1-C10) hydroxyalkyl, (C1-C10) alkyloxy-(C1-C10) alkyl, a substituted or unsubstituted (C1-C10) aminoalkyl, a substituted or unsubstituted aryl, C1-C10 haloalkyl, C2-C6 alkenyl, C2-C6 alkynyl, oxo, a linking group attached to a second steroid, a substituted or unsubstituted (C1-C10) aminoalkyloxy, a substituted or unsubstituted (C1-C10) aminoalkylcarboxy, a substituted or unsubstituted (C1-C10) aminoalkylaminocarbonyl, $H_2N$—HC(Q5)-C(O)—O—, $H_2N$—HC(Q5)-C(O)—N(H)—, (C1-C10) azidoalkyloxy, (C1-C10) cyanoalkyloxy, P.G.-HN—HC(Q5)-C(O)—O—, (C1-C10) guanidinoalkyloxy, and (C1-C10) guanidinoalkylcarboxy, where Q5 is a side chain of any amino acid, P.G. is an amino protecting group, provided that at least three of $R_1$ through $R_4$, $R_6$, $R_7$, $R_{11}$, $R_{12}$, $R_{15}$, $R_{16}$, $R_{17}$, and $R_{18}$ are disposed on the same face of the ring system and are independently selected from the group consisting of a substituted or unsubstituted (C1-C10) aminoalkyl, a substituted or unsubstituted (C1-C10) aminoalkyloxy, (C1-C10) alkylcarboxy-(C1-C10) alkyl, (C1-C10) alkylamino-(C1-C10) alkylamino, (C1-C10) alkylamino-(C1-C10) alkylamino-(C1-C10) alkylamino, a substituted or unsubstituted (C1-C10) aminoalkylcarboxy, a substituted or unsubstituted arylamino-(C1-C10) alkyl, a substituted or unsubstituted (C1-C10) aminoalkyloxy-(C1-C10) aminoalkylaminocarbonyl, a substituted or unsubstituted (C1-C10) aminoalkylaminocarbonyl, a substituted or unsubstituted (C1-C5) aminoalkylcarboxamido, a (C1-C10) quaternaryammoniumalkylcarboxy, $H_2N$—HC(Q5)-C(O)—O—, $H_2N$—HC(Q5)-C(O)—N(H)—, (C1-C10) azidoalkyloxy, (C1-C10) cyanoalkylox, P.G.-HN—HC(Q5)-C(O)—O—, (C1-C10) guanidinoalkyloxy, and a (C1-C10)

guanidinoalkylcarboxy; or a pharmaceutically acceptable salt thereof. In various aspects, at least two, or at least, three, of m, n, p, and q are 1.

Compounds set forth herein preserve certain stereochemical and electronic characteristics found in steroids. The term "same configuration" as used herein refers to substituents on the fused steroid having the same stereochemical orientation. For example substituents $R_3$, $R_7$ and $R_{12}$ are all β-substituted or α-substituted.

Compounds of the invention include but are not limited to compounds having amine or guanidine groups covalently attached to a steroid backbone or scaffold at any carbon position, e.g., cholic acid. In various embodiments, a group is covalently attached at any one, or more, of positions C3, C7 and C12 of the steroid backbone or scaffold. In additional embodiments, a group is absent from any one, or more, of positions C3, C7 and C12 of the steroid backbone or scaffold.

Compounds of the invention that include such groups can include a tether, the tether having variable chain length or size. As used herein, the terms "tether" or "tethered," when used in reference to a compound of the invention, refers to the chain of atoms between the steroid backbone or scaffold and a terminal amino or guanidine group. In various embodiments, a tether is covalently attached at any one, or more, of positions C3, C7 and C12. In additional embodiments, a tether is lacking at any one, or more, of positions C3, C7 and C12. A tether length may include the heteroatom (O or N) covalently attached to the steroid backbone.

Other ring systems can also be used, e.g., 5-member fused rings. Compounds with backbones having a combination of 5- and 6-membered rings are also included in the invention. Amine or guanidine groups can be separated from the backbone by at least one, two, three, four or more atoms. The backbone can be used to orient the amine or guanidine groups on one face, or plane, of the steroid. For example, a scheme showing a compound having primary amino groups on one face, or plane, of a backbone is shown below:

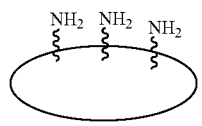

Methods of synthesizing compounds of formula I are provided, wherein for example, at least two of $R_1$ through $R_{14}$ are independently selected from the group consisting of a substituted or unsubstituted (C1-C10) aminoalkyloxy. In one embodiment, a method includes the step of contacting a compound of formula IV,

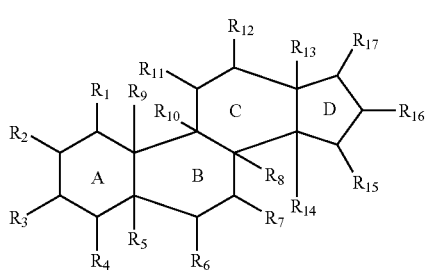

where at least two of $R_1$ through $R_{14}$ are hydroxyl, and the remaining moieties on the fused rings A, B, C, and D are defined for formula I, with an electrophile to produce an alkyl ether compound of formula IV, wherein at least two of $R_1$ through $R_{14}$ are (C1-C10)alkyloxy. The alkyl ether compounds are converted into an amino precursor compound wherein at least two of $R_1$ through $R_{14}$ are independently selected from the group consisting of (C1-C10) azidoalkyloxy and (C1-C10) cyanoalkyloxy and the amino precursor compound is reduced to form a compound of formula I.

The electrophiles used in a method include but are not limited to 2-(2-bromoethyl)-1,3-dioxolane, 2-iodoacetamide, 2-chloroacetamide, N-(2-bromoethyl)phthalimide, N-(3-bromopropyl)phthalimide, and allylbromide. An exemplary electrophile is allylbromide.

The invention also includes methods of producing a compound of formula I where at least two of $R_1$ through $R_{14}$ are (C1-C10) guanidoalkyloxy. In one embodiment, a method includes contacting a compound of formula IV, where at least two of $R_1$ through $R_{14}$ are hydroxyl, with an electrophile to produce an alkyl ether compound of formula IV, where at least two of $R_1$ through $R_{14}$ are (C1-C10)alkyloxy. The allyl ether compound is converted into an amino precursor compound where at least two of $R_1$ through $R_{14}$ are independently selected from the group consisting of (C1-C10) azidoalkyloxy and (C1-C10) cyanoalkyloxy. The amino precursor compound is reduced to produce an aminoalkyl ether compound wherein at least two of $R_1$ through $R_{14}$ are (C1-C10) aminoalkyloxy. The aminoalkyl ether compound is contacted with a guanidino producing electrophile to form a compound of formula I.

The term "guanidino producing electrophile" used herein refers to an electrophile used to produce a guanidino compound of formula I. An example of an guanidino producing electrophile is $HSO_3$—C(NH)—$NH_2$.

The invention also includes methods of producing a compound of formula I where at least two of $R_1$ through $R_{14}$ are H2N—HC(Q5)-C(O)—O— and Q5 is the side chain of any amino acid. In one embodiment, a method includes the step of contacting a compound of formula IV, where at least two of $R_1$ through $R_{14}$ are hydroxyl, with a protected amino acid to produce a protected amino acid compound of formula IV where at least two of at least two of $R_1$ through $R_{14}$ are P.G.-HN—HC(Q5)-C(O)—O— and Q5 is the side chain of any amino acid and P.G. is an amino protecting group. The protecting group of the protected amino acid compound is removed to form a compound of formula I.

Exemplary non-limiting synthesis schemes for preparing compounds of the invention include the following:

Scheme 1 Illustrates Preparation of Compounds 1, 2, 4 and 5

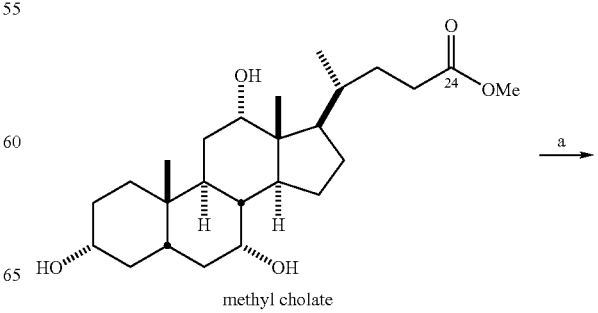

methyl cholate

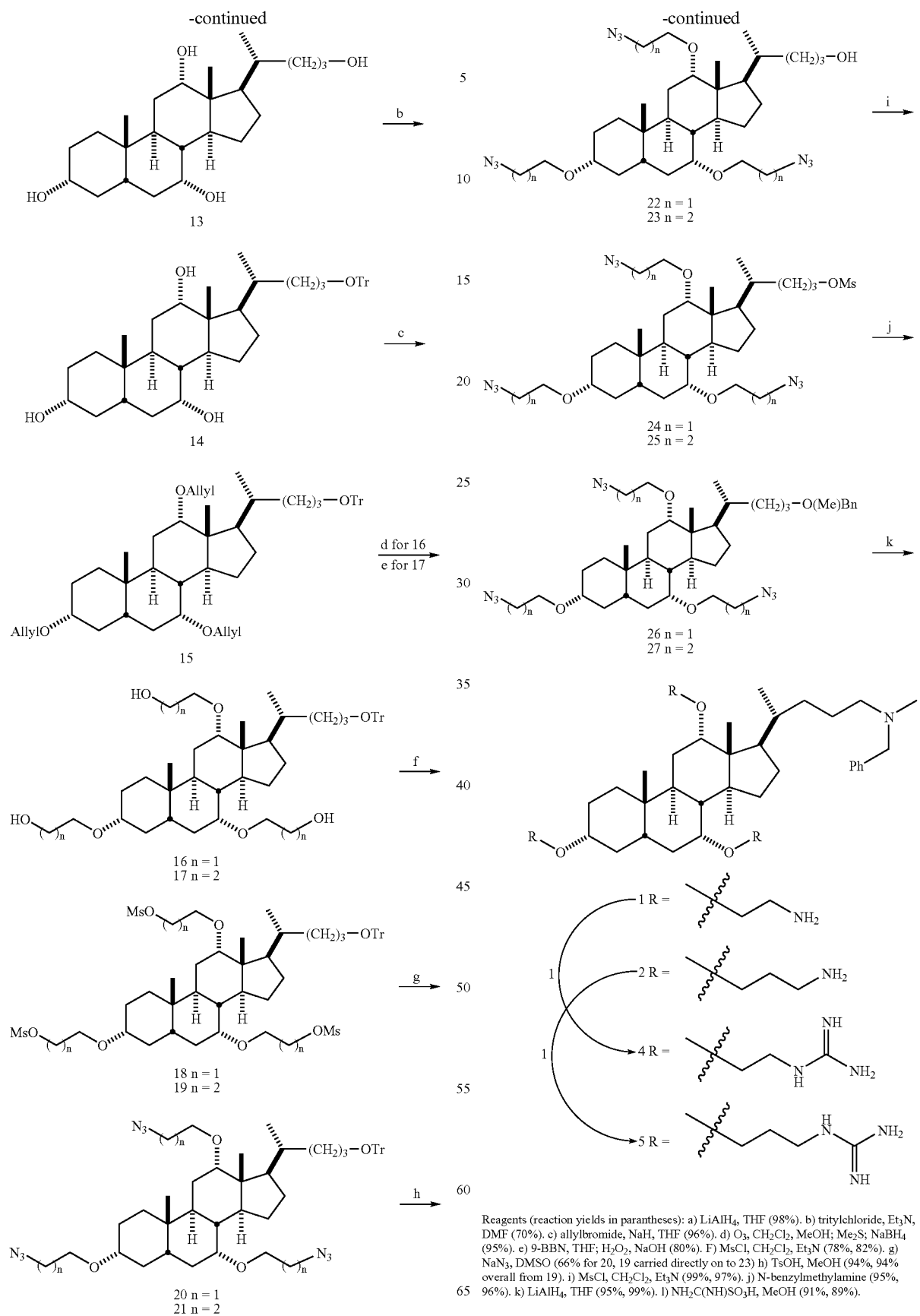

Scheme 2 Illustrates Preparation of Compound 3
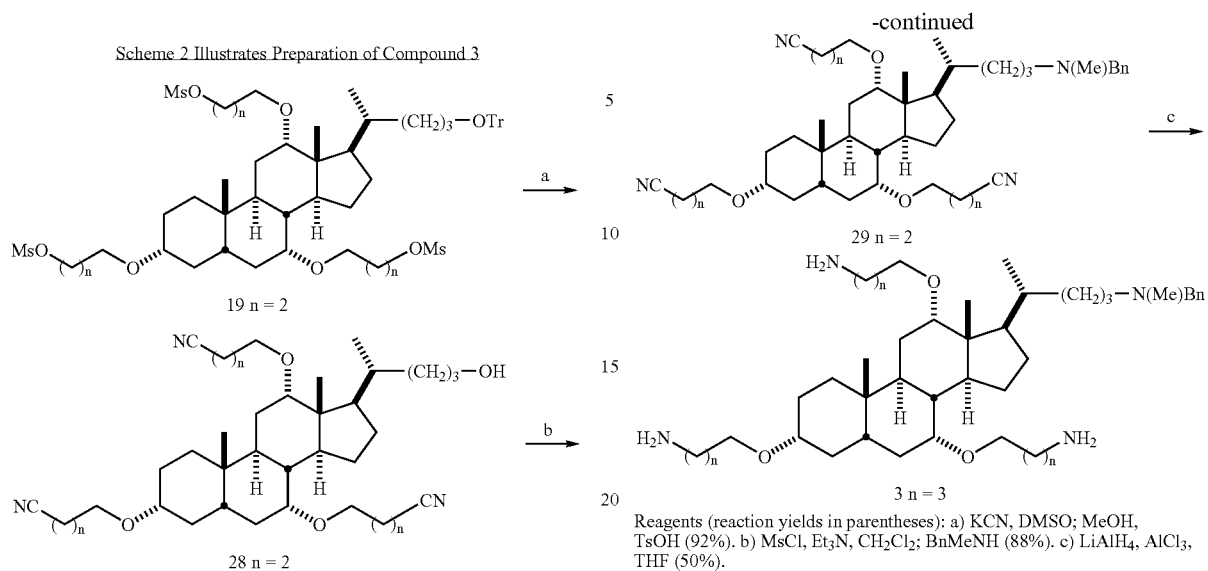
Reagents (reaction yields in parentheses): a) KCN, DMSO; MeOH, TsOH (92%). b) MsCl, Et$_3$N, CH$_2$Cl$_2$; BnMeNH (88%). c) LiAlH$_4$, AlCl$_3$, THF (50%).
Scheme 3 Illustrates Preparation of Compounds 6 and 7
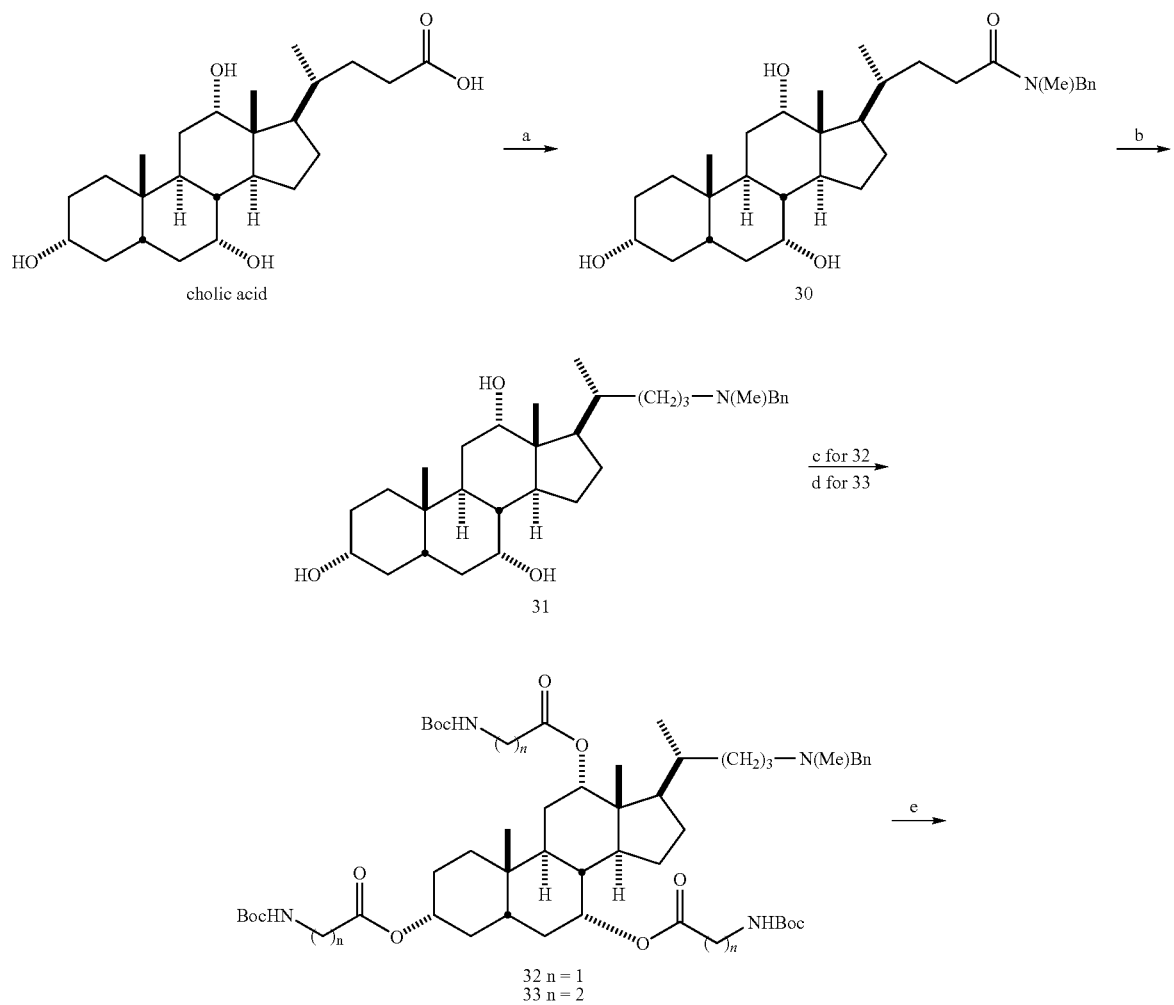

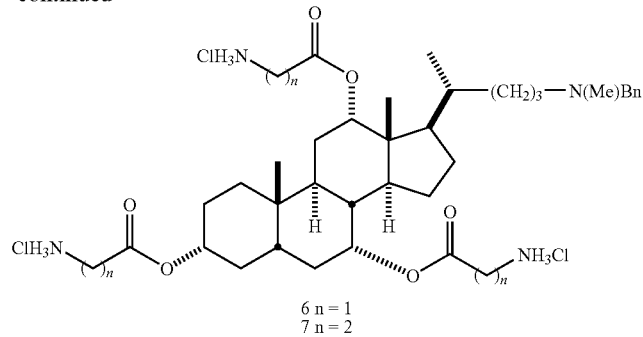
6 n = 1
7 n = 2
Reagents (reaction yields in parantheses): a) dicyclohexylcarbodiimide, N-hydroxysuccinimide, methylphenylamine, CH$_2$Cl$_2$, MeOH (85%). b) LiAlH$_4$, THF (82%). c) dicyclohexylcarbodiimide, dimethylaminopyridine, Boc-glycine, CH$_2$Cl$_2$ (68%). d) dicyclohexylcarbodiimide, dimethylaminopyridien, Boc-b-alanine, CH$_2$Cl$_2$ (72%). e) dioxane (ca 100%, ca. 100%)
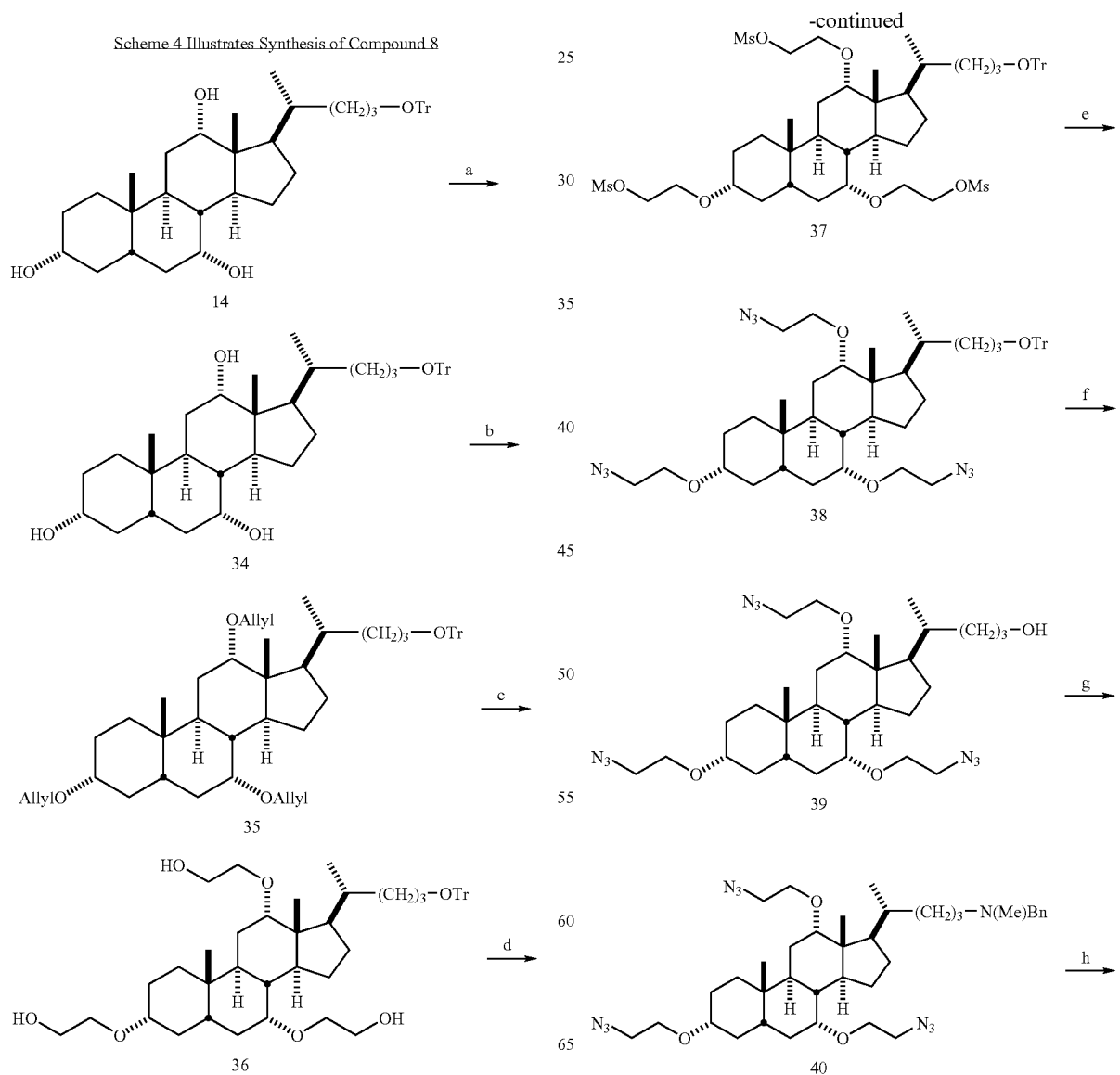

-continued

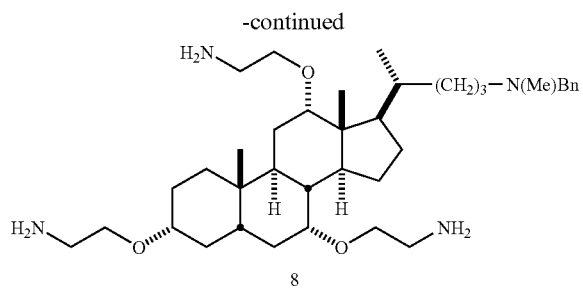

8

Reagents (reaction yields in parantheses): a) DIAD, Ph₃P, p-nitrobenzoic acid, THF (85%); NaOH, MeOH (85%). B) allylbromide, NaH, THF (79%). C) O₃, CH₂Cl₂, MeOH; Me₂S; NaBH₄, (65%). d) MsCl, CH₂Cl₂, Et₃N (86%). e) NaN₃, DMSO (80%). f) TsOH, MeOH (94%). g) MsCl, CH₂Cl₂, Et₃N; N-benzylmethylamine (93%). g) LiAlH₄, THF (94%).

Scheme 5 Illustrates Synthesis of Compounds CSA-7 and CSA-8

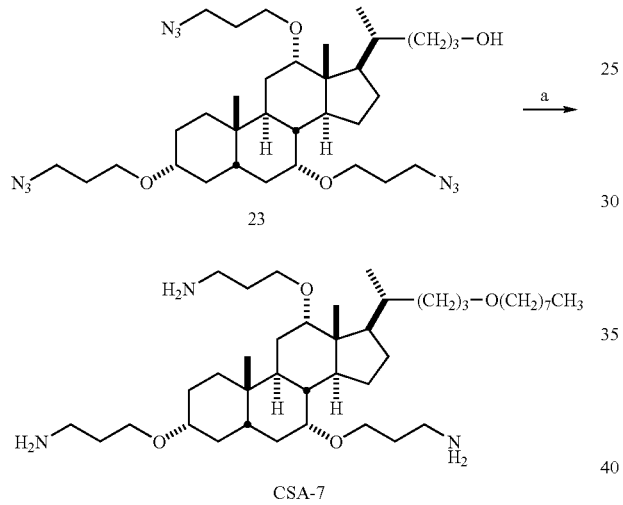

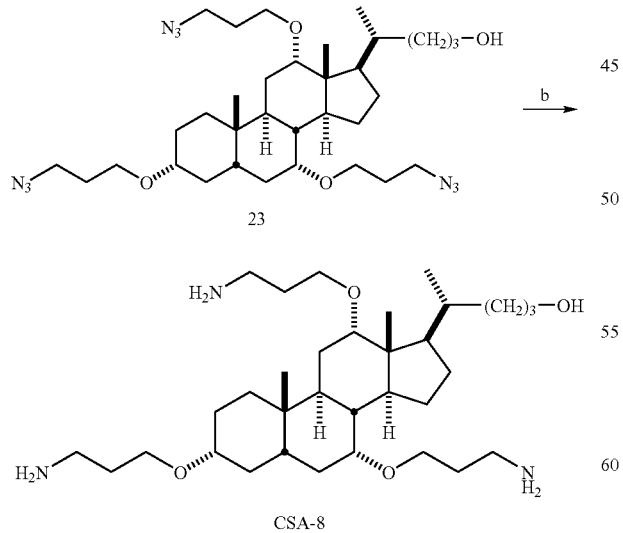

Reagents (reaction yields in parantheses): a) NaH, octylbromide, DMF (80%); LiAlH₄, THF (60%). b) LiAlH₄, THF (60%).

Scheme 6 Illustrates Synthesis of Compound CSA-11

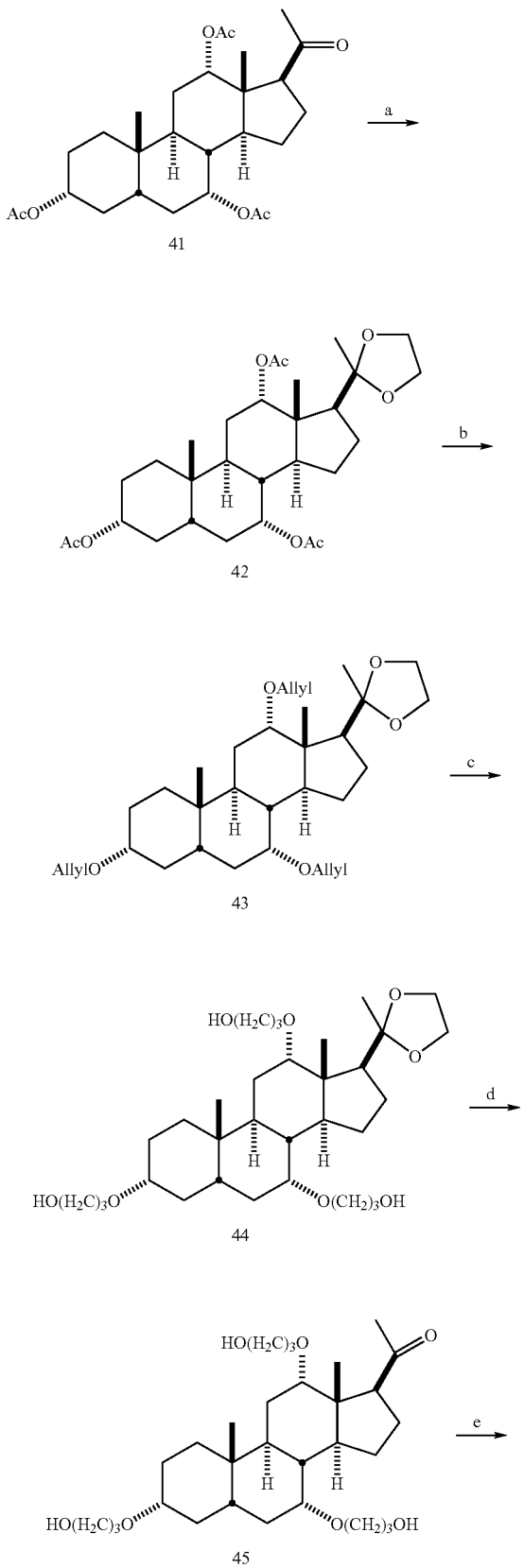

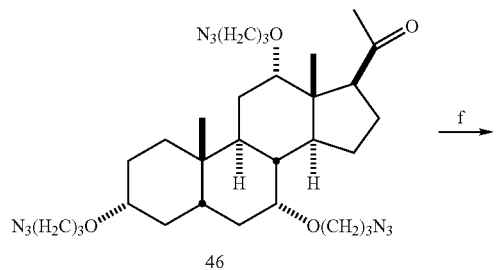

46

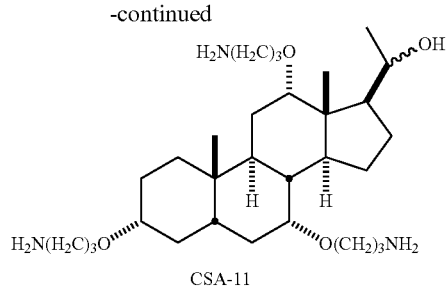

CSA-11

Reagents (reaction yields in parantheses): a) ethylene glycol, p-toluenesolfonic acid, benzene; NaOH, MeOH (96%). b) allylbromide, NaH, THF (90%). c) 9-BBN, THF; NaOH, H$_2$O$_2$, H$_2$O (54%). d) pyridinium p-toluenesulfonate, MeOH (98%). e) methanesulfonyl chloride, Et$_3$N, CH$_2$Cl$_2$; NaN$_3$, DMSO (88%). f) LiAlH$_4$, THF (69%).

Scheme 7 Illustrates Synthesis of Compound CSA-10

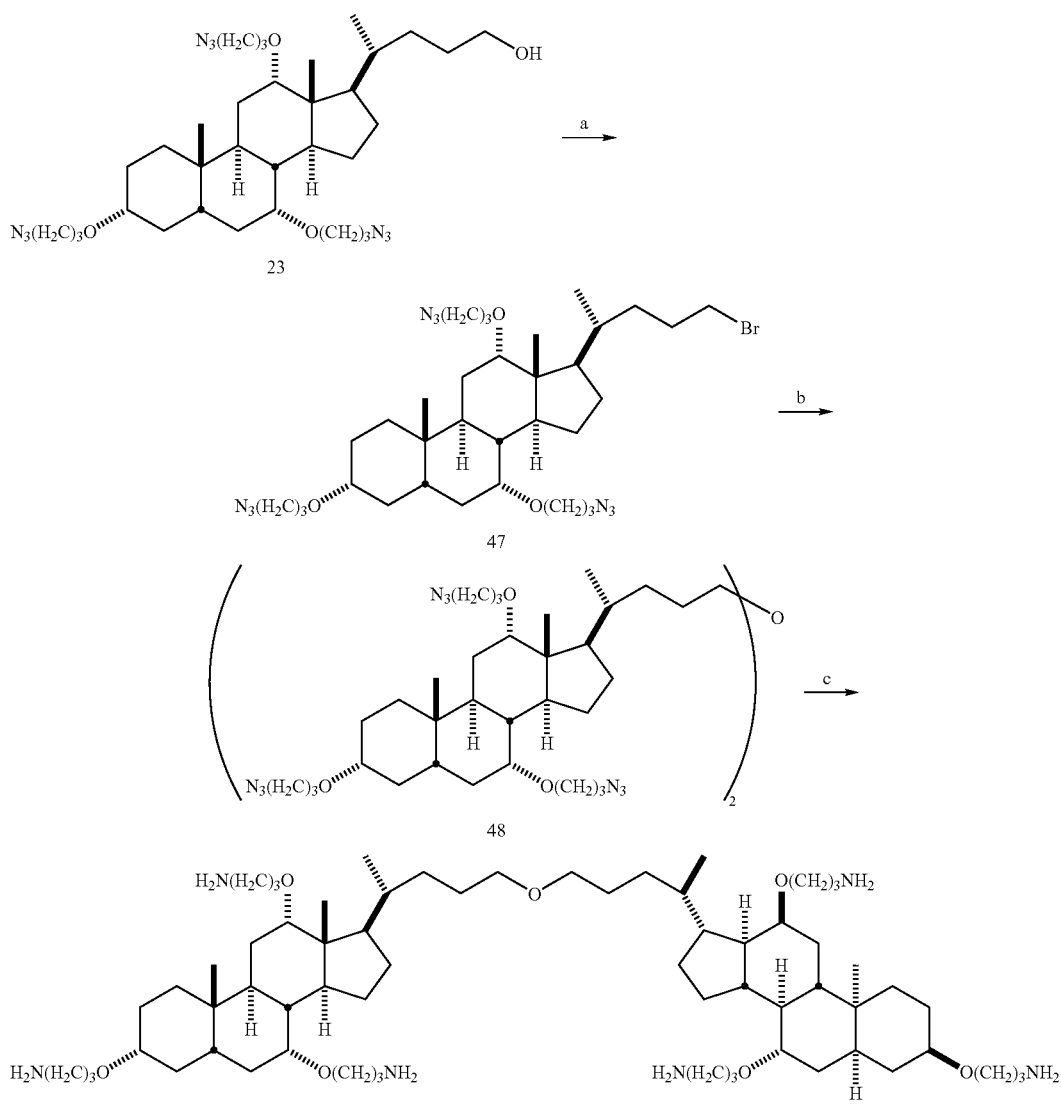

CSA-10

Reagents (reaction yields in parantheses): a) methanesulfonylchloride, Et$_3$N, CH$_2$Cl$_2$; NaBr, DMF (97%). B) 23, NaH, DMF (52%). C) LiAlH$_4$, THF (76%).

Scheme 8 Illustrates Preparation of Compounds 111, CSA-17, 113 and CSA-7

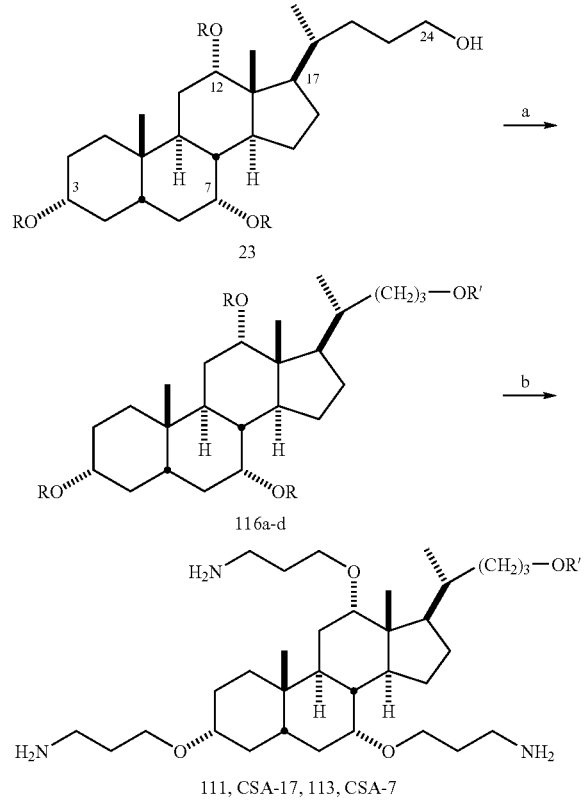

for 23, 116a-d. R = ––(CH$_2$)$_3$N$_3$   for 116a, 111, R' = ––CH$_3$
for 116b, CSA-17, R' = ––(CH$_2$)$_2$CH$_3$   for 116c and 113, R' = ––(CH$_2$)$_4$CH$_3$
for 116d and CSA-7, R' = ––(CH$_2$)$_7$CH$_3$ Reagents (reaction yields in parantheses): a) NaH, DMF, CH$_3$I, CH$_3$(CH$_2$)$_2$Br, CH$_3$(CH$_2$)$_4$Br, or CH$_3$(CH$_2$)$_7$Br (85-90%). B) LiAlH$_4$, THF (55-70%).

Scheme 9 Illustrates Preparation of Compound 106

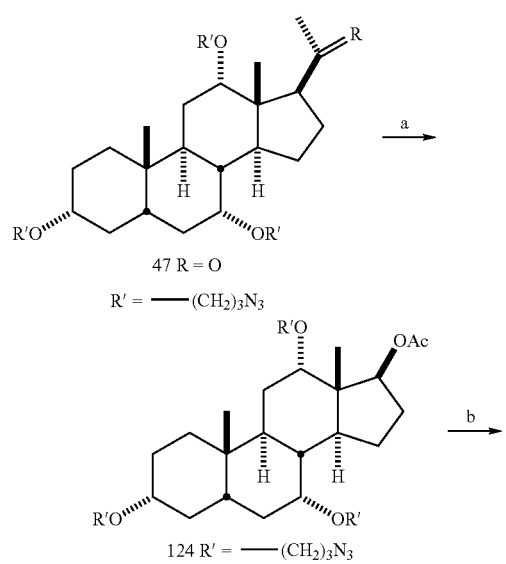

Reagents (reaction yields in parantheses): a) Urea-hydrogen peroxide complex, trifluoroacetic anhydride, CH$_2$Cl$_2$ (55%). B) NaOH, MeOH; LiAl$_4$, THF (43%).

Scheme 10 Illustrates Preparation of Compounds 108 and 109

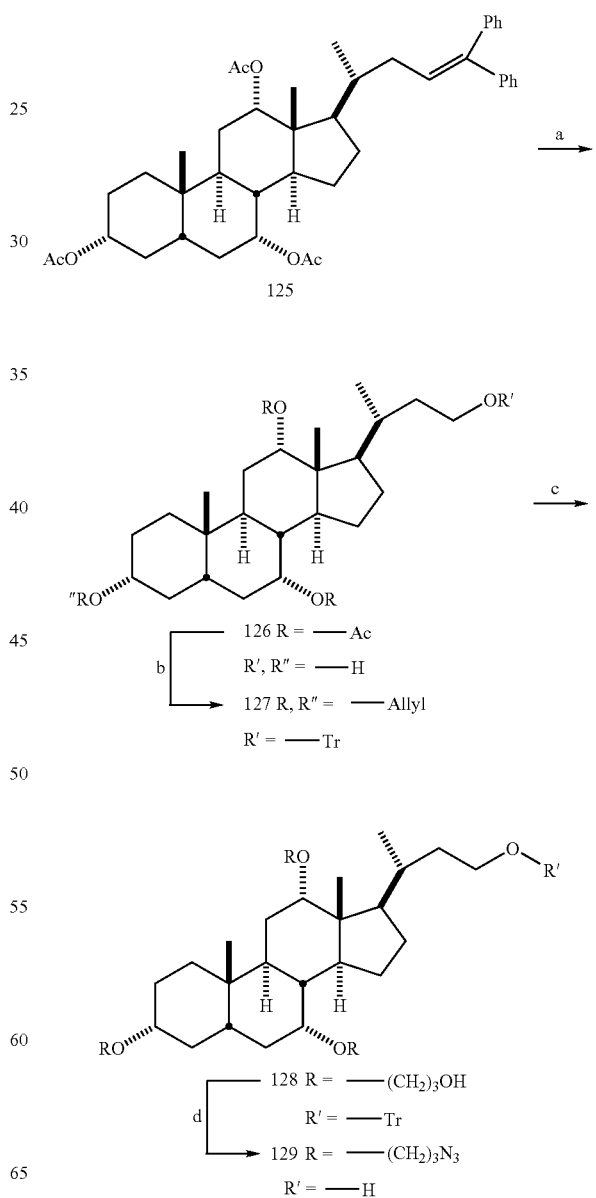

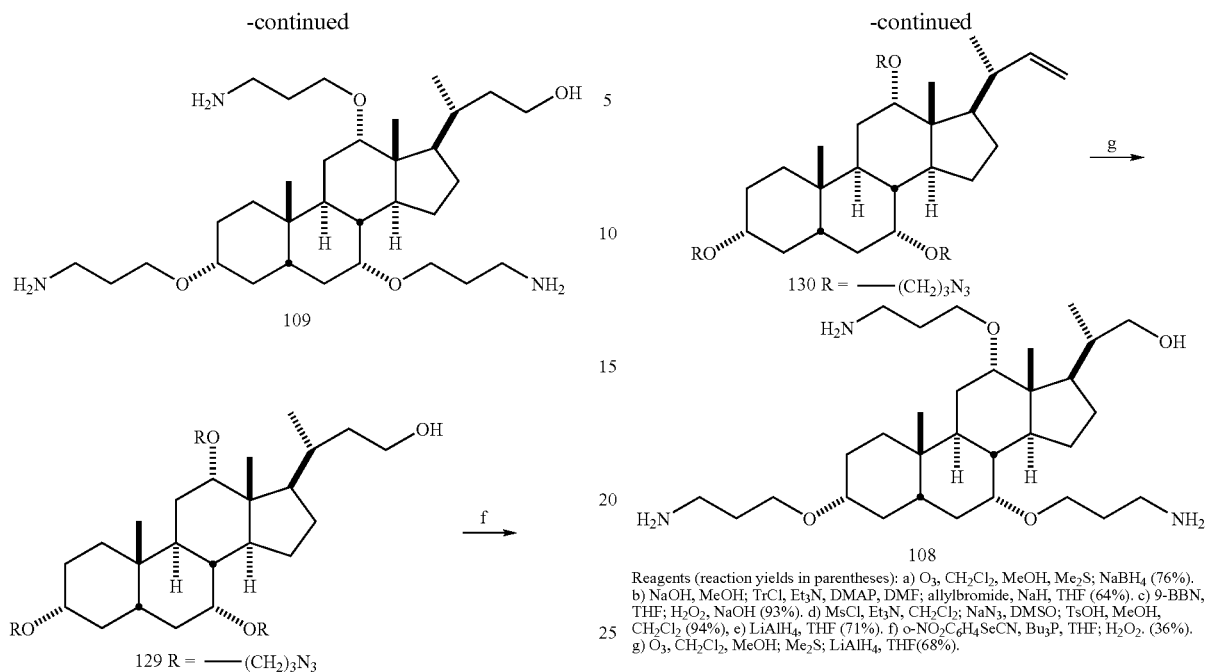
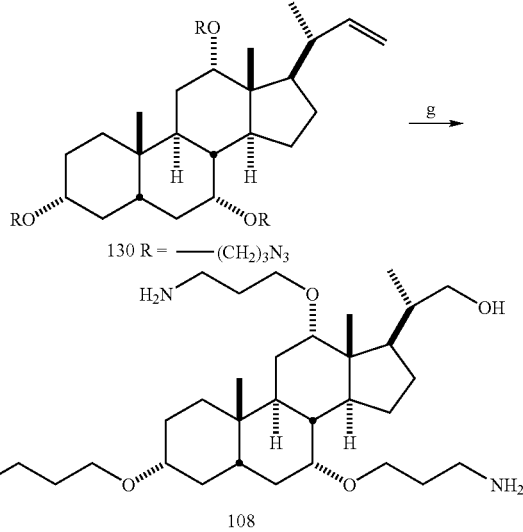

Reagents (reaction yields in parentheses): a) O$_3$, CH$_2$Cl$_2$, MeOH, Me$_2$S; NaBH$_4$ (76%). b) NaOH, MeOH; TrCl, Et$_3$N, DMAP, DMF; allylbromide, NaH, THF (64%). c) 9-BBN, THF; H$_2$O$_2$, NaOH (93%). d) MsCl, Et$_3$N, CH$_2$Cl$_2$; NaN$_3$, DMSO; TsOH, MeOH, CH$_2$Cl$_2$ (94%). e) LiAlH$_4$, THF (71%). f) o-NO$_2$C$_6$H$_4$SeCN, Bu$_3$P, THF; H$_2$O$_2$. (36%). g) O$_3$, CH$_2$Cl$_2$, MeOH; Me$_2$S; LiAlH$_4$, THF (68%).

Scheme 11 Illustrates Preparation of Compounds 202 and 203

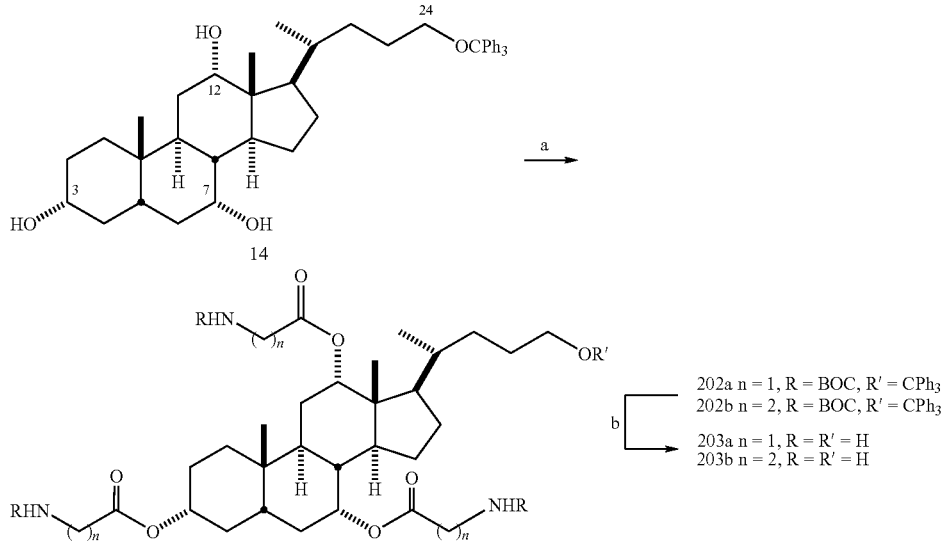

Reagents (reaction yields in parentheses): a) BOC-glycine or BOC-alanine, DCC, DMAP, CH$_2$Cl$_2$ (60%, 94%). b) 4 M HCl in dioxane (74%, 71%).

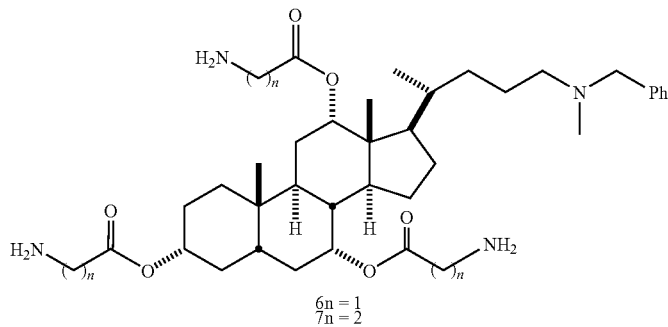

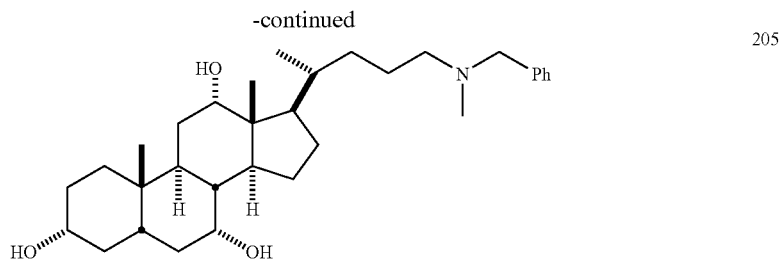
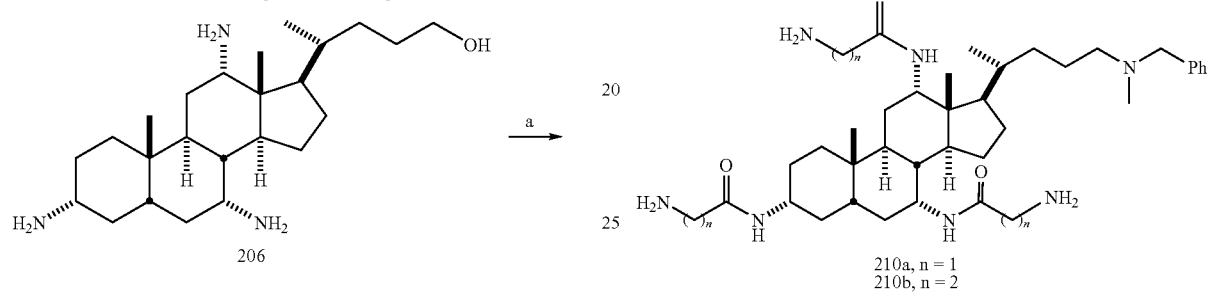
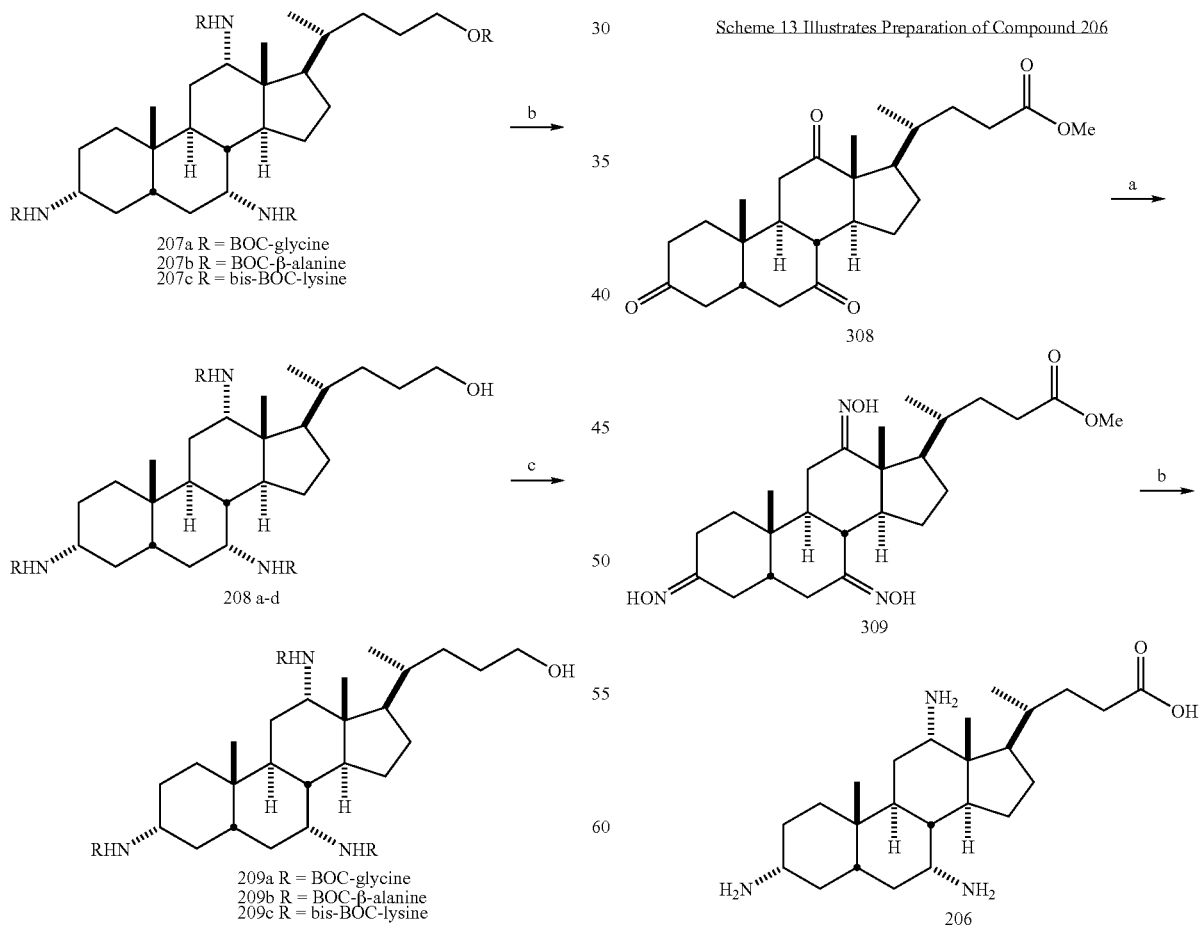
Reagents (reaction yields in parentheses): a) BOC-glycine, BOC-alanine or bis-BOC-lysine, DCC, DMAP, $CH_2Cl_2$. b) LiOH, THF, MeOH (71-85% for two steps). c) 4 M HCl in dioxane (ca. 100%)
Reagents (reaction yields in parentheses): a) $NH_2OH \cdot HCl$, AcONa., EtOH (97%). b) $NaBH_4$, $TiCl_4$, glyme (33%).

Scheme 14 Illustrates Syntheses of Compounds 324-326
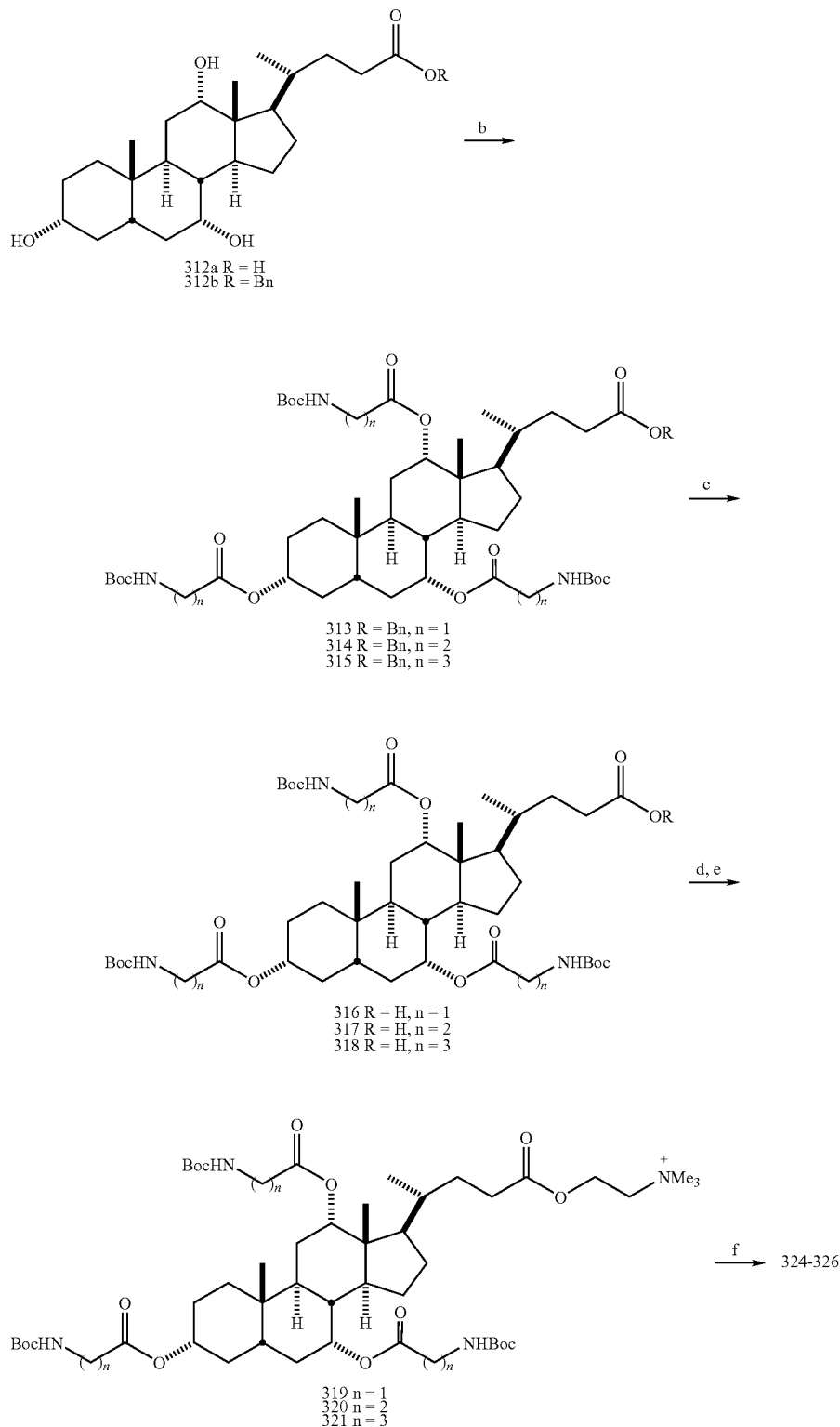
Reagents (reaction yields in parentheses): a) benzyl alcohol. b) BOC-glycine, BOC-β-alanine or -BOC-γ-aminobutyric acid, DCC, DMAP, CH$_2$Cl$_2$ (68-78%). c) H$_2$, Pd/C (97-99%). d) (CH$_3$)$_2$N(CH$_2$)$_2$OH, DCC, DMAP, CH$_2$Cl$_2$ or THF (62-82%). E) MeI, CH$_2$Cl$_2$. f) HCl, dioxane (83-90% for two steps).

Scheme 15 Illustrates Syntheses of Compounds 341-343
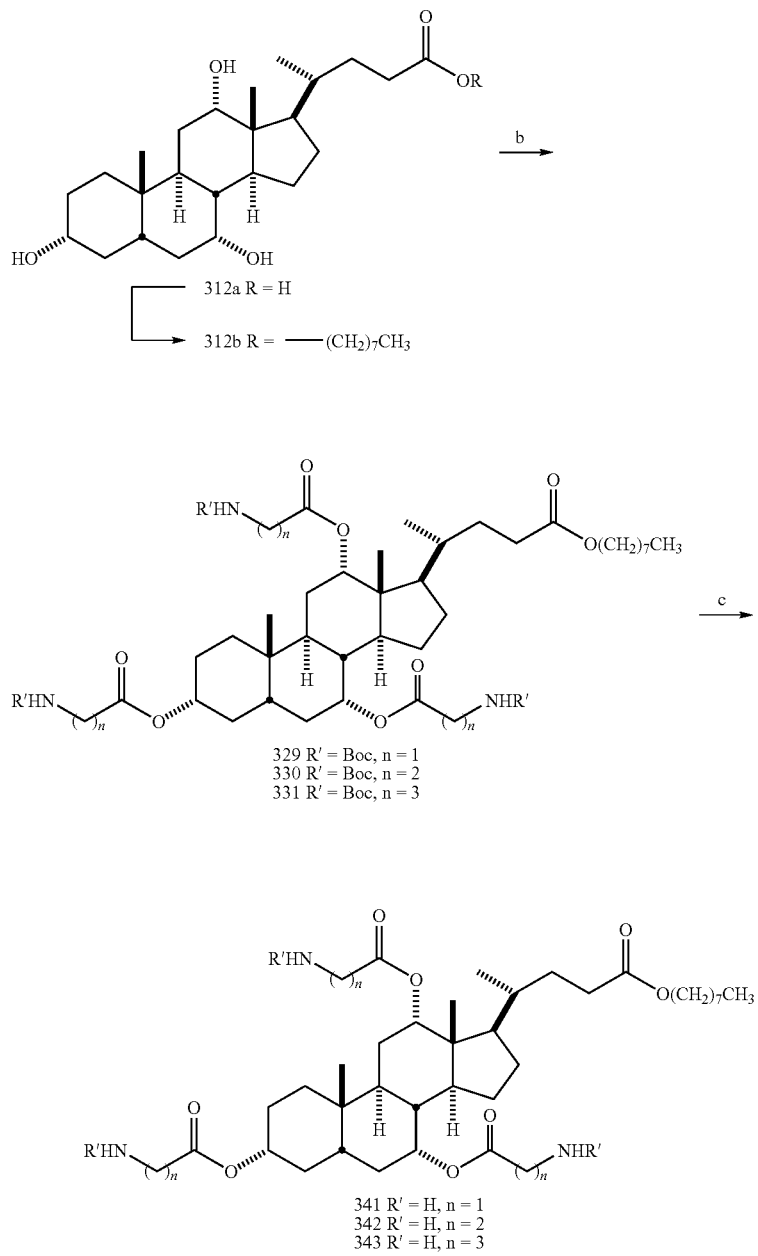
Reagents (reaction yields in parentheses): a) octanol, TsOH (73%). b) Boc-glycine, Boc-β-alanine or -Boc-γ-aminobutyric acid, DCC, DMAP, CH$_2$Cl$_2$ (91-95%). c) HCl, dioxane (84-99%).
Scheme 16 Illustrates Synthesis of Compound 356
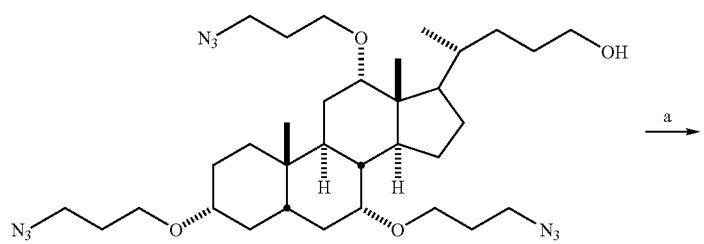

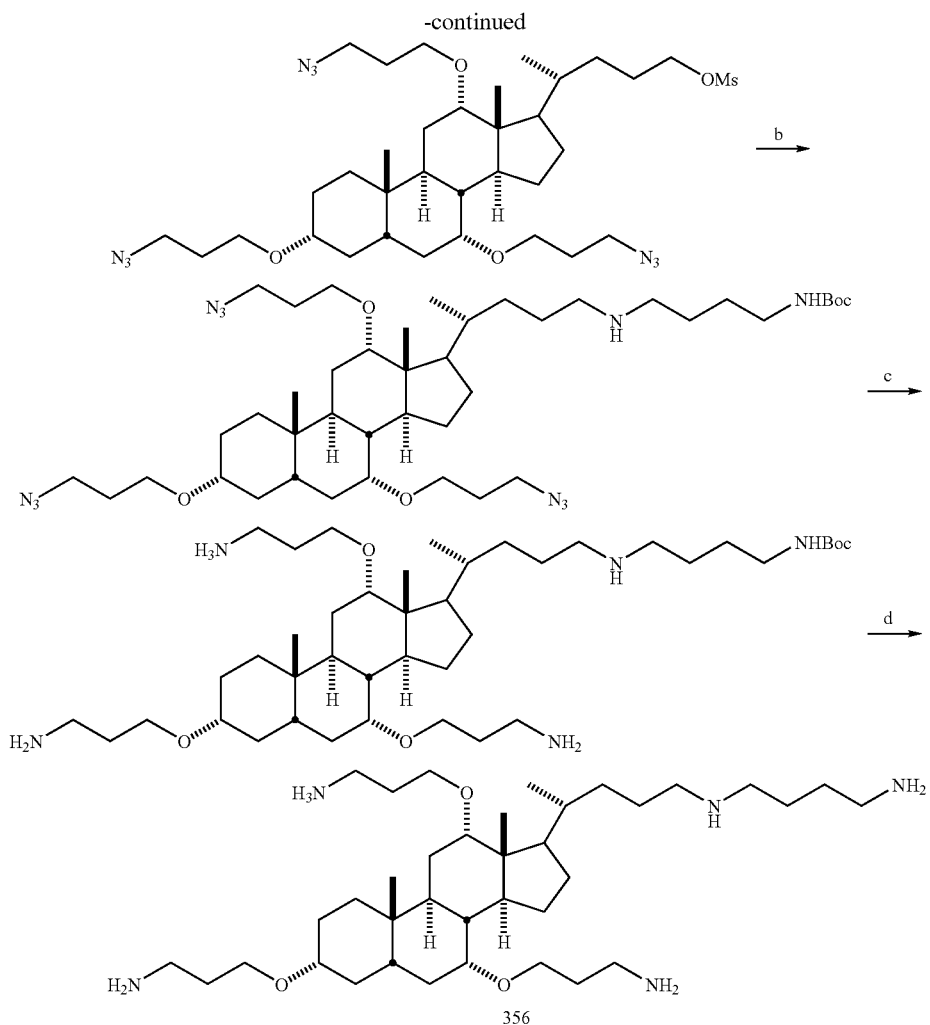
Reagents (reaction yields in parentheses): a) MsCl, NEt₃, CH₂Cl₂ (86%). b) NH₂(CH₂)₃NHBoc, THF (97%). c) PPh₃, THF/H₂O, (86%). d) HCl, 2M in ethyl ether, (89%).
Scheme 17 Illustrates Synthesis of Compound CSA-54
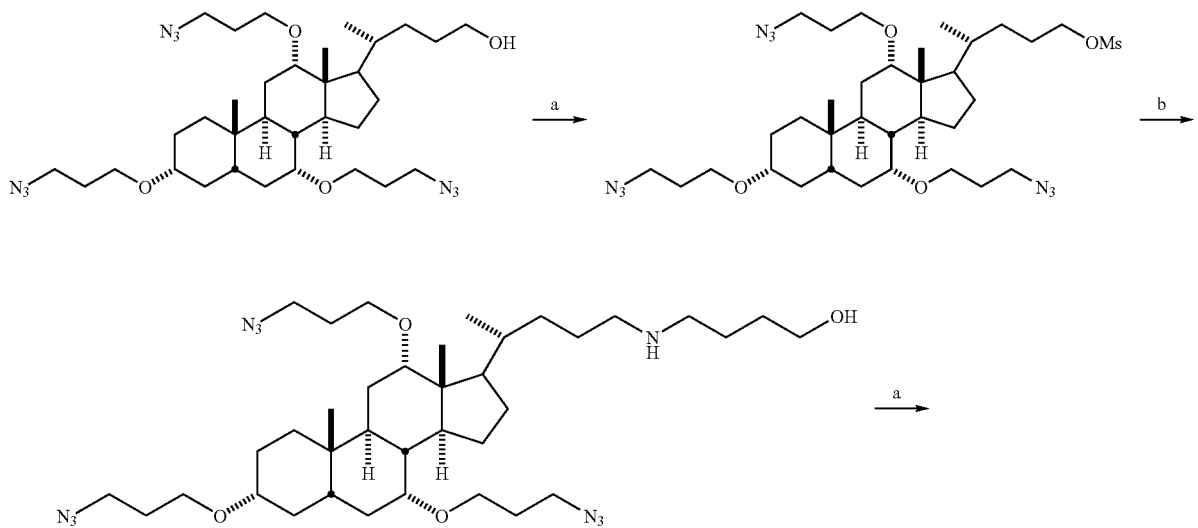

-continued

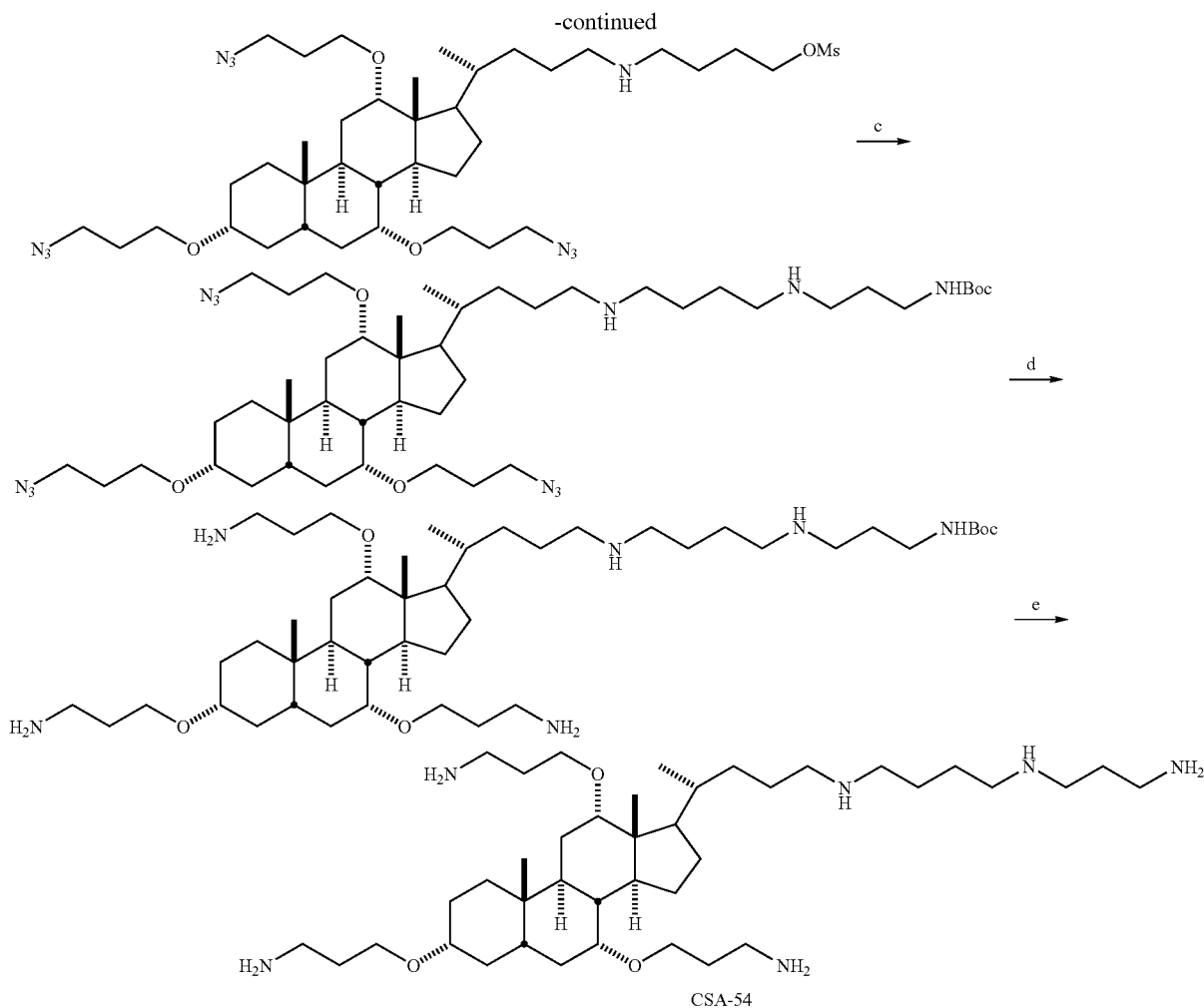

CSA-54

Reagents (reaction yields in parentheses): a) MsCl, NEt₃, CH₂Cl₂ (86%). b) NH₂(CH₂)₃OH, THF, then step a. (63%). c) NH₂(CH₂)₃NHBoc, THF, (83%). d) PPh₃, THF/H₂O (90%). e) HCl, 2M in ethyl ether, (94%).

Compounds of the invention and precursors to the compounds according to the invention are available commercially, e.g., from Sigm-Aldrich Co., St. Louis; Mo.; and Research Plus, Inc., Manasquan, N.J. Other compounds according to the invention can be synthesized according to methods disclosed herein, in U.S. Pat. Nos. 6,350,738; 6,486, 148;and 6,767,904, and in the art.

Methods for identifying a candidate agent for treating a subject for a poxvirus infection or pathogenesis, for decreasing susceptibility of a subject to a poxvirus infection or pathogenesis, and decreasing or preventing an adverse side effect caused by vaccination of a subject with or against a poxvirus, are provided. In one embodiment, a method includes providing a test agent, such as a cationic steroid antimicrobial (CSA); contacting the test agent with poxvirus and ascertaining whether the test agent inhibits poxvirus infection or pathogenesis. A test agent identified as inhibiting poxvirus infection or pathogenesis is a candidate agent for treating a subject for poxvirus infection or pathogenesis. A test agent identified as inhibiting poxvirus infection or pathogenesis is also a candidate agent for decreasing susceptibility of a subject to a poxvirus infection or pathogenesis. A test agent identified as inhibiting poxvirus infection or pathogenesis is further a candidate agent for decreasing or preventing an adverse side effect caused by vaccination of a subject with a poxvirus. In various aspects, the subject is a mammal. For example, a mammal can comprises an animal model for poxvirus infection or pathogenesis.

Unless otherwise defined, all technical and scientific terms used herein have the same meaning as commonly understood by one of ordinary skill in the art to which this invention belongs. Although methods and materials similar or equivalent to those described herein can be used in the practice or study of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., compound structures) are an example of a genus of equivalent or similar features.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a compound"

includes a plurality of compounds and reference to "an antipoxvirus effect, activity or function" can include reference to one or more effects, activities or functions, and so forth.

As used herein, all numerical values or numerical ranges include integers within such ranges and fractions of the values or the integers within ranges unless the context clearly indicates otherwise. Thus, to illustrate, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of doses, such as 0.1-1 ug/kg, 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, includes 0.11-0.9 ug/kg, 2-9 ug/kg, 11.5-24.5 ug/kg, 26-49 ug/kg, 55-90 ug/kg, 125-400 ug/kg, 750-800 ug/kg, 1.1-4.9 mg/kg, 6-9 mg/kg, 11.5-19.5 mg/kg, 21-49 mg/kg, 55-90 mg/kg, 125-200 mg/kg, 275.5-450.1 mg/kg, etc.

The invention is generally disclosed herein using affirmative language to describe the numerous embodiments. The invention also includes embodiments in which subject matter is excluded, in full or in part, such as substances or materials, method steps and conditions, protocols, or procedures. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. For example, salts, esters, ethers and amides of invention compounds disclosed herein are within the scope of this invention. Accordingly, the following examples are intended to illustrate but not limit the scope of invention described in the claims.

EXAMPLES

CSA compounds and intermediates were characterized using the following instruments: $^1$H and $^{13}$C NMR spectra were recorded on a Varian Gemini 2000 (200 MHz), Varian Unity 300 (300 MHz), or Varian VXR 500 (500 MHz) spectrometer and are referenced to TMS, residual CHCl$_3$ ($^1$H) or CDCl$_3$ ($^{13}$C), or residual CHD$_2$OD ($^1$H), or CD$_3$OD ($^{13}$C). IR spectra were recorded on a Perkin Elmer 1600 FTIR instrument. Mass spectrometric data were obtained on a JOEL SX 102A spectrometer. THF solvent was dried over Na/benzophenone and CH$_2$Cl$_2$ was dried over CaH$_2$ prior to use. Other reagents and solvents were obtained commercially and were used as received.

Example 1

This example includes a description of one or more exemplary synthetic procedures for obtaining Compounds 1-5, 13-20 and 22-27.

Compound 13: To a 1 L round-bottom flask were added methyl cholate (30.67 g, 72.7 mmol) in dry THF (600 mL) and LiAlH$_4$ (4.13 g, 109 mmol). After reflux for 48 hours, saturated aqueous Na$_2$SO$_4$ (100 mL) was introduced slowly, and the resulted precipitate was filtered out and washed with hot THF and MeOH. Recrystallization from MeOH gave colorless crystals of 13 (28.0 g, 98% yield). m.p. 236.5-238° C.; IR (KBr) 3375, 2934, 1373, 1081 cm$^{-1}$; $^1$H NMR (CDCl$_3$/MeOH-d$_4$, 200 MHz) δ 3.98 (bs, 1 H), 3.83 (bs, 1 H), 3.60-3.46 (m, 2 H), 3.38 (bs, 5 H), 2.30-2.10 (m, 2 H), 2.05-1.05 (series of multiplets, 22 H), 1.03 (bs, 3 H), 0.92 (s, 3 H), 0.71 (s, 3 H); $^{13}$C NMR (CDCl$_3$/MeOH-d$_4$, 50 MHz) δ 73.89, 72.44, 68.99, 63.51, 48.05, 47.12, 42.49, 40.37, 39.99, 36.62, 36.12, 35.58, 35.40, 32.77, 30.69, 30.04, 29.02, 28.43, 27.27, 23.96, 23.08, 18.00, 13.02; HRFAB-MS (thioglycerol+Na$^+$ matrix) m/e: ([M+Na]$^+$) 417.2992 (55.3%); calcd. 417.2981.

Compound 14: To a round-bottom flask were added 13 (28.2 g, 71.7 mmol) in DMF (300 ml), Et$_3$N (20 mL, 143.4 mmol), trityl chloride (25.98 g, 93.2 mmol) and DMAP (0.13 g, 1.07 mmol). The mixture was stirred at 50° C. under N$_2$ for 30 hours followed by the introduction of water (1000 mL) and extraction with EtOAc (5×200 mL). The combined extracts were washed with water and brine and then dried over MgSO$_4$. After removal of solvent in vacuo, the residue was purified using SiO$_2$ chromatography (CH$_2$Cl$_2$, Et$_2$O and MeOH as eluents) to give 14 as a pale yellow solid (31.9 g, 70% yield). m.p. 187° C. (decomposition); IR (KBr) 3405, 2935, 1448, 1075 cm$^{-1}$; $^1$H NMR (CDCl$_3$, 200 MHz) δ 7.46-7.42 (m, 6 H), 7.32-7.17 (m, 9 H), 3.97 (bs, 1 H), 3.83 (bs, 1 H), 3.50-3.38 (m, 1 H), 3.01 (bs, 1 H), 2.94 (dd, J=14.2, 12.2 Hz, 2 H), 2.64 (bs, 1 H), 2.51 (bs, 1 H), 2.36-2.10 (m, 2 H), 2.00-1.05 (series of multiplets, 22 H), 0.96 (d, J=5.8 Hz, 3 H), 0.87 (s, 3 H), 0.64 (s, 3 H); $^{13}$C NMR (CDCl$_3$, 50 MHz) δ 144.77, 128.93, 127.91, 127.01, 86.43, 73.35, 72.06, 68.66, 64.28, 47.47, 46.53, 41.74, 41.62, 39.64, 35.57, 35.46, 34.91, 34.82, 32.40, 30.55, 28.21, 27.69, 26.80, 26.45, 23.36, 22.59, 17.83, 12.61; HRFAB-MS (thioglycerol+Na$^+$ matrix) m/e: ([M+Na]$^+$) 659.4069 (100%); calcd. 659.4076.

Compound 15: To a round-bottom flask were added 14 (20.0 g, 31.4 mmol) in dry THF (600 mL) and NaH (60% in mineral oil, 6.3 g, 157.2 mmol). The mixture was refluxed for 30 min under N$_2$ followed by addition of allyl bromide (27 mL, 314 mmol). After 60 hours of reflux, additional NaH (3 eq.) and allyl bromide (4 eq.) were added. Following another 50 hours of reflux, water (20 mL) was introduced slowly followed by addition of 1% HCl until the aqueous layer became neutral. The mixture was then extracted with ether (3×100 mL) and the combined extracts were washed with water (100 mL) and brine (2×100 mL). The ether solution was dried over anhydrous Na$_2$SO$_4$, and after removal of solvent, the residue was purified using SiO$_2$ chromatography (hexanes and EtOAc/hexanes 1:8 as eluents) to give 15 (22.76 g, 96% yield) as a pale yellow glass. IR (neat) 2930, 1448, 1087 cm$^{-1}$; $^1$H NMR (CDCl$_3$, 200 MHz) δ 7.48-7.30 (m, 6 H), 7.32-7.14 (m, 9 H), 6.04-5.80 (m, 3 H), 5.36-5.04 (series of multiplets, 6 H), 4.14-3.94 (m, 4 H), 3.74 (td, J=13.8, 5.8 Hz, 2 H), 3.53 (bs, 1 H), 3.20-2.94 (m, 3 H), 3.31 (bs, 1 H), 2.38-1.90 (m, 4 H), 1.90-0.96 (series of multiplets, 20 H), 0.90 (d, J=5.4 Hz, 3 H), 0.89 (s, 3 H), 0.64 (s, 3 H); $^{13}$C NMR (CDCl$_3$, 50 MHz) δ 144.83, 136.27, 136.08, 128.94, 127.90, 126.98, 116.46, 115.70, 86.42, 80.94, 79.29, 74.98, 69.52, 69.39, 68.86, 64.39, 46.51, 46.42, 42.67, 42.14, 39.92, 35.63, 35.51, 35.13, 32.45, 28.98, 28.09, 27.66, 27.57, 26.72, 23.32, 23.11, 17.92, 12.69; HRFAB-MS (thioglycerol+Na$^+$ matrix) m/e: ([M+Na]$^+$) 779.5013 (86.1%); calcd. 779.5015.

Compound 16: To a three-necked round bottom flask was added 15 (3.34 g, 4.4 mmol) in CH$_2$Cl$_2$ (200 mL) and methanol (100 mL). Through the cold solution (−78° C.) ozone was bubbled through until a blue color persisted. Excess ozone was removed with oxygen flow. The mixture was left in a dry ice-acetone bath for an hour. Methyl sulfide (2.4 mL) was added and 15 minutes later, the mixture was treated with NaBH$_4$ (1.21 g, 32 mmol) in 5% aqueous NaOH solution (10 mL)/methanol (10 mL) and allowed to warm to room temperature. The mixture was washed with brine (3×50 mL), and the combined brine wash was extracted with CH$_2$Cl$_2$ (2×50 mL). The organic solution was dried over MgSO$_4$. After SiO$_2$ chromatography (MeOH (5%) in CH$_2$Cl$_2$), 3.30 g (95% yield) of 16 was isolated as an oil. IR (neat) 3358, 2934, 1448, 1070 cm$^{-1}$; $^1$H NMR (CDCl$_3$, 200 MHz) δ 7.50-7.42 (m, 6 H), 7.32-7.17 (m, 9 H), 3.80-2.96 (series of multiplets, 20 H), 2.25-0.96 (series of multiplets, 24 H), 0.89 (bs, 6 H), 0.65 (s, 3 H); $^{13}$C NMR (CDCl$_3$, 50 MHz) δ 144.73, 128.88, 127.87, 126.96, 86.38, 81.05, 79.75, 76.59, 70.33, 69.66, 69.30, 64.20, 62.25, 62.16, 62.03, 46.77, 46.36, 42.63, 41.77, 39.60, 35.43, 35.23, 35.05, 34.89, 32.42, 28.91, 27.93, 27.56, 27.15, 26.68, 23.35, 22.98, 22.85, 18.15, 12.60; HRFAB-MS (thioglycerol+Na$^+$ matrix) m/e: ([M+Na]$^+$) 791.4860 (100%), calcd. 791.4863.

Compound 17: To a round-bottom flask was added 16 (1.17 g, 1.55 mmol) in dry THF (30 mL) under N$_2$ in ice-bath followed by 9-BBN/THF solution (0.5 M, 10.2 mL, 5.51 mmol). The mixture was stirred at room temperature for 12 hours. Aqueous NaOH (20%) (2 mL) and hydrogen peroxide (30%) (2 mL) were added in sequence. The mixture was refluxed for 1 hour followed by the addition of brine (60 mL) and extraction with EtOAc (4×30 mL). The combined extracts were dried over anhydrous Na$_2$SO$_4$. The product (1.01 g, 80% yield) was obtained as a colorless oil after SiO$_2$ chromatography (5% MeOH in CH$_2$Cl$_2$). IR (neat) 3396, 2936, 1448, 1365, 1089 cm$^{-1}$; $^1$H NMR(CDCl$_3$, 200 MHz) δ 7.50-7.42 (m, 6 H), 7.34-7.16 (m, 9 H), 3.90-3.56 (m, 13 H), 3.50 (bs, 1 H), 3.40-2.96 (series of multiplets, 6 H), 2.30-0.94 (series of multiplets, 30 H), 0.90 (s, 3 H), 0.88 (d, J=5.4 Hz, 3 H), 0.64 (s, 3 H); $^{13}$C NMR(CDCl$_3$, 50 MHz) δ 144.73, 128.88, 127.85, 126.94, 86.36, 80.52, 78.90, 76.36, 66.82, 66.18, 65.77, 64.22, 61.53, 61.41, 61.34, 46.89, 46.04, 42.60, 41.59, 39.60, 35.37, 35.27, 34.88, 32.75, 32.44, 32.31, 28.82, 27.65, 27.48, 27.13, 26.77, 23.35, 22.74, 22.38, 18.08, 12.48; HRFAB-MS (thioglycerol+Na$^+$ matrix) m/e: ([M+Na]$^+$) 833.5331 (100%), calcd. 833.5332.

Compound 18: To a round-bottom flask were added 16 (3.30 g, 4.29 mmol) in CH$_2$Cl$_2$ (150 mL) and NEt$_3$ (2.09 mL, 15.01 mmol). The mixture was put in ice-bath under N$_2$ followed by addition of mesyl chloride (1.10 mL, 14.16 mmol). After 30 minutes, water (30 mL) and brine (200 mL) were added. The CH$_2$Cl$_2$ layer was washed with brine (2×50 mL) and dried over anhydrous Na$_2$SO$_4$. The combined aqueous mixture was extracted with EtOAc (3×100 mL). The combined extracts were washed with brine and dried over anhydrous Na$_2$SO$_4$. The desired product (3.35 g, 78% yield) was isolated as a pale yellow oil after SiO$_2$ chromatography (EtOAc/hexanes 1:1). IR (neat) 2937, 1448, 1352, 1174, 1120, 924 cm$^{-1}$; $^1$H NMR (CDCl$_3$, 200 MHz) δ 7.52-7.40 (m, 6 H), 7.34-7.20, (m, 9 H), 4.42-4.24 (m, 6 H), 3.90-3.64 (m, 4 H), 3.60-3.30 (m, 4 H), 3.24-3.00 (m, 3 H), 3.10 (s, 6 H), 3.05 (s, 3 H), 2.20-1.96 (m, 3 H)1.96-1.60 (m, 8 H), 1.60-0.94 (series of multiplets, 13 H), 0.91 (bs, 6 H), 0.65 (s, 3 H); $^{13}$C NMR(CDCl$_3$, 50 MHz) δ 114.68, 128.85, 127.85, 126.96, 86.37, 81.37, 79.58, 76.58, 69.95, 69.43, 69.34, 66.52, 66.31, 65.59, 64.11, 46.80, 46.20, 42.65, 41.48, 39.35, 37.82, 37.48, 35.36, 34.92, 34.73, 32.37, 28.66, 28.01, 27.44, 27.03, 26.72, 23.17, 22.91, 22.72, 18.13, 12.50; HRFAB-MS (thioglycerol+Na$^+$ matrix) m/e: ([M+Na]$^+$) 1205.4176 (81.5%), calcd. 1205.4189.

Compound 19: To a round-bottom flask were added 17 (1.01 g, 1.25 mmol) in CH$_2$Cl$_2$ (50 mL) and NEt$_3$ (0.608 mL, 4.36 mmol). The mixture was put in ice-bath under N$_2$ followed by addition of mesyl chloride (0.318 mL, 4.11 mmol). After 30 minutes, water (10 mL) and then brine (80 mL) were added. The CH$_2$Cl$_2$ layer was washed with brine (2×20 mL) and dried over anhydrous Na$_2$SO$_4$. The combined aqueous mixture was extracted with EtOAc (3×40 mL). The combined extracts were washed with brine and dried over anhydrous Na$_2$SO$_4$. The desired product (1.07 g, 82%) was isolated as a pale yellowish oil after SiO$_2$ chromatography (EtOAc/hexanes 1:1). IR (neat) 2938, 1356, 1176, 1112 cm$^{-1}$; $^1$H NMR (CDCl$_3$, 300 MHz) δ 7.46-7.43, (m, 6 H), 7.32-7.22 (m, 9 H), 4.40-4.31 (m, 6 H), 3.72-3.64 (m, 2 H), 3.55 (dd, J=6.3, 5.8 Hz, 2 H), 3.51 (bs, 1 H), 3.32-3.14 (m, 3 H), 3.14-2.92 (m, 3 H), 3.01 (s, 3 H), 3.01 (s, 3 H), 3.00 (s, 3 H), 2.10-1.92 (m, 10 H), 1.92-1.58 (m, 8 H), 1.56-0.92 (series of multiplets, 12 H), 0.90 (s, 3 H), 0.89 (d, J=5.4 Hz, 3 H), 0.64 (s, 3 H); $^{13}$C NMR(CDCl$_3$, 75 MHz) δ 144.67, 128.85, 127.85, 126.96, 86.42, 81.06, 79.83, 76.81, 68.12, 68.06, 68.02, 64.26, 64.06, 63.42, 46.76, 46.38, 42.73, 41.87, 39.73, 37.44, 37.32, 37.29, 35.52, 35.48, 35.32, 35.06, 32.53, 30.55, 30.28, 30.02, 29.15, 27.96, 27.69, 27.61, 26.75, 23.52, 23.02, 18.17, 12.64; HRFAB-MS (thioglycerol+Na$^+$ matrix) m/e: ([M+Na]$^+$) 1067.4672 (100%), calcd. 1067.4659.

Compound 20: To a round-bottom flask were added 18 (1.50 g, 1.50 mmol) in dry DMSO (20 mL) and NaN$_3$ (0.976 g, 15 mmol). The mixture was heated to 80° C. and stirred under N$_2$ overnight then diluted with water (100 mL). The resulted aqueous mixture was extracted with EtOAc (3×50 mL), and the combined extracts washed with brine and dried over anhydrous Na$_2$SO$_4$. The desired product (0.83 g, 66% yield) was isolated as a clear glass after SiO$_2$ chromatography (EtOAc/hexanes 1:5). IR (neat) 2935, 2106, 1448, 1302, 1114 cm$^{-1}$; $^1$H NMR (CDCl$_3$, 200 MHz) δ 7.50-7.42 (m, 6 H), 7.36-7.20 (m, 9 H), 3.84-3.70 (m, 2 H), 3.65 (t, J=4.9 Hz, 2 H), 3.55 (bs, 1 H), 3.44-3.08 (m, 10 H), 3.02 (t, J=6.4 Hz, 2 H), 2.38-0.96 (series of multiplets, 24 H), 0.92 (d, J=5.6 Hz, 3 H), 0.91 (s, 3 H), 0.65 (s, 3 H); $^{13}$C NMR (CDCl$_3$, 50 MHz) δ 114.84, 128.97, 127.92, 126.99, 86.42, 81.24, 80.12, 76.59, 67.84, 67.29, 66.66, 64.36, 51.67, 51.44, 51.18, 46.53, 46.23, 42.21, 41.93, 39.73, 35.66, 35.36, 35.06, 34.78, 32.40, 28.95, 27.76, 27.39, 26.87, 23.45, 22.98, 22.92, 17.98, 12.53; HRFAB-MS (thioglycerol$^+$Na$^+$ matrix) m/e: ([M+Na]$^+$) 866.5040 (100%), calcd. 866.5057.

Compound 22: To a round-bottom flask were added 20 (830 mg, 0.984 mmol) in MeOH (30 mL) and CH$_2$Cl$_2$ (30 mL) and p-toluenesulfonic acid (9.35 mg, 0.0492 mmol). The solution was stirred at room temperature for 2.5 hours then saturated aqueous NaHCO$_3$ (10 mL) was introduced. Brine (30 mL) was added, and the mixture was extracted with EtOAc (4×20 mL). The combined extracts were dried over anhydrous Na$_2$SO$_4$. The desired product (0.564 g, 95% yield) was isolated as a pale yellowish oil after SiO$_2$ chromatography (EtOAc/hexanes 1:2). IR (neat) 3410, 2934, 2106, 1301, 1112 cm$^{-1}$; $^1$H NMR (CDCl$_3$, 200 MHz) δ 3.80-3.54 (m, 7 H), 3.44-3.20 (m, 10 H), 2.35-0.96 (series of multiplets, 24 H), 0.95 (d, J=6.4 Hz, 3H), 0.92 (s, 3 H), 0.68 (s, 3 H); $^{13}$C NMR (CDCl$_3$, 50 MHz) δ 81.10, 80.01, 76.60, 67.75, 67.16, 66.56, 63.63, 51.57, 51.34, 51.06, 46.29, 46.12, 42.12, 41.81, 39.60, 35.55, 35.23, 34.94, 34.66, 31.75, 29.48, 28.81, 27.72, 27.66, 27.29, 23.32, 22.86, 22.80, 17.85, 12.39; HRFAB-MS (thioglycerol+Na$^+$ matrix) m/e: ([M+Na]$^+$) 624.3965 (100%), calcd. 624.3962.

Compound 23: To a round-bottom flask were added 19 (1.07 g, 1.025 mmol) and NaN$_3$ (0.666 g, 10.25 mmol) followed the introduction of dry DMSO (15 mL). The mixture was heated up to 80° C. under N$_2$ overnight. After the addition of H$_2$O (100 mL), the mixture was extracted with EtOAc (4×40 mL) and the combined extracts were washed with brine (2×50 mL) and dried over anhydrous Na$_2$SO$_4$. After removal of solvent, the residue was dissolved in MeOH (15 mL) and CH$_2$Cl$_2$ (15 mL) followed by the addition of catalytic amount of p-toluenesulfonic acid (9.75 mg, 0.051 mmol). The solution was stirred at room temperature for 2.5 hours before the addition of saturated NaHCO$_3$ solution (15 mL). After the addition of brine (60 mL), the mixture was extracted with EtOAc (5×30 mL). The combined extracts were washed with brine (50 mL) and dried over anhydrous Na$_2$SO$_4$. The desired product (0.617 g, 94% yield for two steps) was obtained as a yellowish oil after SiO$_2$ chromatography (EtOAc/hexanes 1:2). IR (neat) 3426, 2928, 2094, 1456, 1263, 1107 cm$^{-1}$; $^1$H NMR (CDCl$_3$, 300 MHz) δ 3.68-3.56 (m, 3 H), 3.56-3.34 (series of multiplets, 10 H), 3.28-3.00 (series of multiplets, 4 H), 2.20-2.00 (m, 3 H), 1.98-1.55 (series of multiplets, 15 H), 1.55-0.96 (series of multiplets, 13 H), 0.92 (d, J=6.6 Hz, 3 H), 0.89 (s, 3 H), 0.66 (s, 3 H); $^{13}$C NMR (CDCl$_3$, 75 MHz) δ 80.63, 79.79, 76.04, 64.99, 64.45, 64.30, 63.72, 49.01, 48.94, 48.74, 46.49, 46.39, 42.70, 41.98, 39.80, 35.65, 35.42, 35.28, 35.08, 31.99, 29.78, 29.75, 29.70, 29.49, 29.06, 27.87, 27.79, 27.65, 23.53, 23.04, 22.85, 18.05, 12.59; HRFAB-MS (thioglycerol+Na matrix) m/e: ([M+Na]$^+$) 666.4415 (100%), calcd. 666.4431.

Compound 24: To a round-bottom flask were added 22 (0.564 g, 0.938 mmol) in CH$_2$Cl$_2$ (30 mL) and NEt$_3$ (0.20 mL, 1.40 mmol). The mixture was put in ice-bath under N$_2$ followed by addition of mesyl chloride (0.087 mL, 1.13 mmol). After 30 minutes, water (20 mL) and brine (100 mL) were added. The CH$_2$Cl$_2$ layer was washed with brine (2×20 mL) and dried over anhydrous Na$_2$SO$_4$. The combined aqueous mixture was extracted with EtOAc (3×30 mL). The combined extracts were washed with brine and dried over anhydrous Na$_2$SO$_4$. The desired product (0.634 g, 99% yield) was isolated as a pale yellowish oil after SiO$_2$ chromatography (EtOAc/hexanes 1:2). IR (neat) 2935, 2106, 1356, 1175, 1113 cm$^{-1}$; $^1$H NMR (CDCl$_3$, 300 MHz) δ 4.20 (t, J=6.8 Hz, 2 H), 3.80-3.75 (m, 1 H), 3.70-3.64 (m, 3 H), 3.55 (bs, 1 H), 3.44-3.01 (m, 10 H), 3.00 (s, 3 H), 2.32-2.17 (m, 3 H), 2.06-2.03 (m, 1 H), 1.90-0.88 (series of multiplets, 20 H), 0.95 (d, J=6.6 Hz, 3 H), 0.91 (s, 3 H), 0.68 (s, 3 H); $^{13}$C NMR (CDCl$_3$, 75 MHz) δ 80.90, 79.86, 76.43, 70.78, 67.64, 66.99, 66.48, 51.50, 51.26, 50.97, 46.05, 45.96, 42.08, 41.71, 39.51, 37.33, 35.15, 34.86, 34.60, 31.34, 28.73, 27.62, 27.59, 27.51, 25.68, 23.22, 22.80, 22.70, 17.62, 12.33; HRFAB-MS (thioglycerol+Na$^+$ matrix) m/e: ([M+Na]$^+$) 702.3741 (100%), calcd. 702.3737.

Compound 25: To a round-bottom flask were added 23 (0.617 g, 0.96 mmol) in CH$_2$Cl$_2$ (30 mL) and NEt$_3$ (0.20 mL, 1.44 mmol). The mixture was put in ice-bath under N$_2$ followed by addition of mesyl chloride (0.089 mL, 1.15 mmol). After 30 minutes, water (20 mL) and brine (120 mL) were added. The CH$_2$Cl$_2$ layer was washed with brine (2×20 mL) and dried over anhydrous Na$_2$SO$_4$. The combined aqueous mixture was extracted with EtOAc (3×30 mL). The combined extracts were washed with brine and dried over anhydrous Na$_2$SO$_4$. The desired product (0.676 g, 97% yield) was isolated as a pale yellowish oil after removal of solvent. IR (neat) 2934, 2094, 1454, 1360, 1174, 1112 cm$^{-1}$; $^1$H NMR (CDCl$_3$, 300 MHz) δ 4.17 (t, J=6.6 Hz, 2 H), 3.65-3.28 (series of multiplets, 11 H), 3.64-3.00 (series of multiplets, 4 H), 2.97 (s, 3 H), 2.18-1.96 (series of multiplets, 16 H), 1.54-0.94 (series of multiplets, 11 H), 0.89 (d, J=6.6 Hz, 3 H), 0.86 (s, 3 H), 0.63 (s, 3 H); $^{13}$C NMR (CDCl$_3$, 75 MHz) δ 80.47, 79.67, 75.92, 70.84, 64.90, 64.37, 64.17, 48.90, 48.86, 48.66, 46.32, 46.26, 42.63, 41.87, 39.70, 37.39, 35.34, 35.28, 35.20, 34.99, 31.61, 29.68, 29.60, 28.96, 27.78, 27.68, 27.57, 25.79, 23.41, 22.95, 22.74, 17.82, 12.50; HRFAB-MS (thioglycerol matrix) m/e: ([M+H]$^+$) 722.4385 (22.1%), calcd. 722.4387.

Compound 26: To a 50 mL round-bottom flask was added 24 (0.634 g, 0.936 mmol) and N-benzylmethylamine (2 mL). The mixture was heated under N$_2$ at 80° C. overnight. Excess N-benzylmethylamine was removed under vacuum, and the residue was subjected to SiO$_2$ chromatography (EtOAc/hexanes 1:2). The desired product (0.6236 g, 95% yield) was isolated as a pale yellow oil. IR (neat) 2935, 2106, 1452, 1302, 1116 cm$^{-1}$; $^1$H NMR (CDCl$_3$, 200 MHz) δ 7.32-7.24 (m, 5 H), 3.80-3.76 (m, 1 H), 3.70-3.60 (m, 3 H), 3.54 (bs, 1 H), 3.47 (s, 2 H), 3.42-3.10 (m, 10 H), 2.38-2.05 (m, 5 H), 2.17 (s, 3 H), 2.02-0.88 (series of multiplet, 21 H), 0.93 (d, J=7.0 Hz, 3 H), 0.91 (s, 3 H), 0.66 (s, 3 H); $^{13}$C NMR (CDCl$_3$, 50 MHz) δ 139.60, 129.34, 128.38, 127.02, 81.22, 80.10, 76.71, 67.85, 67.29, 66.65, 62.45, 58.38, 51.65, 51.44, 51.16, 46.50, 46.21, 42.40, 42.20, 41.93, 39.72, 35.80, 35.34, 35.05, 34.76, 33.65, 28.93, 27082, 27.75, 27.38, 24.10, 23.45, 22.98, 22.91, 18.05, 12.50; HRFAB-MS (thioglycerol+Na$^+$ matrix) m/e: ([M−H]$^+$) 703.4748 (90.2%), calcd. 703.4772;([M+H]$^+$) 705.4911 (100%), calcd. 705.4928;([M+Na]$^+$) 727.4767 (1.5%), calcd. 727.4748.

Compound 27: To a 50 mL round-bottom flask was added 25 (0.676 g, 0.937 mmol) and N-benzylmethylamine (2 mL). The mixture was heated under N$_2$ at 80° C. overnight. Excess N-benzylmethylamine was removed under vacuum, and the residue was subjected to SiO$_2$ chromatography (EtOAc/hexanes 1:2). The desired product (0.672 g, 96% yield) was isolated as a pale yellow oil. IR (neat) 2934, 2096, 1452, 1283, 1107 cm$^{-1}$; $^1$H NMR (CDCl$_3$, 300 MHz) δ 7.34-7.20 (m, 5 H), 3.68-3.37 (series of multiplets, 13 H), 3.28-3.04 (m, 4 H), 2.33 (t, J=7.0 Hz, 2 H), 2.18 (s, 3 H), 2.20-2.00 (m, 3 H), 1.96-1.56 (series of multiplets, 14 H), 1.54-1.12 (m, 10 H), 1.10-0.96 (m, 3 H), 0.91 (d, J=8.7 Hz, 3 H), 0.89 (s, 3 H), 0.65 (s, 3 H); $^{13}$C NMR (CDCl$_3$, 75 MHz) δ 139.48, 129.23, 128.30, 126.96, 80.66, 79.81, 76.08, 65.00, 64.46, 64.34, 62.50, 58.37, 49.02, 48.95, 48.75, 46.65, 46.40, 42.69, 42.43, 42.00, 39.83, 35.86, 35.45, 35.30, 35.10, 33.83, 29.81, 29.78, 29.72, 29.09, 27.88, 27.81, 27.66, 24.19, 23.57, 23.06, 22.87, 18.15, 12.62; HRFAB-MS (thioglycerol matrix) m/e: ([M+H]$^+$) 747.5406 (77.2%), calcd. 747.5398.

Compound 1: To a round-bottom flask were added 26 (0.684 g, 0.971 mmol) in dry THF (30 mL) and LiAlH$_4$ (113.7 mg, 3.0 mmol) under N$_2$. The mixture was stirred at room temperature for 12 hours, and then Na$_2$SO$_4$.10 H$_2$O powder (10 g) was added slowly. After the grey color disappeared, the mixture was filtered through Celite and washed with dry THF. The product (0.581 g, 95% yield) was obtained as a colorless glass. IR (neat) 3372, 2937, 1558, 1455, 1362, 1102 cm$^{-1}$; $^1$H NMR (CDCl$_3$, 300 MHz) δ 7.34-7.20 (m, 5 H), 3.68-3.48 (m, 5 H), 3.47 (s, 2 H), 3.29 (bs, 1 H), 3.22-3.00 (m, 3 H), 2.96-2.80 (m, 6 H), 2.32 (t, J=6.8, 5.4 Hz, 2 H), 2.17 (s, 3 H), 2.20-2.00 (m, 3 H), 1.96-0.96 (series of multiplets, 27 H), 0.93 (d, J=6.8 Hz, 3 H), 0.90, (s, 3 H), 0.67 (s, 3 H); $^{13}$C NMR (CDCl$_3$, 75 MHz) δ 139.50, 129.22, 128.31, 126.96, 80.76, 79.85, 76.10, 70.90, 70.33, 70.24, 62.48, 58.27, 46.55, 46.45, 42.72, 42.58, 42.33, 41.99, 39.77, 35.78, 35.37, 35.01, 33.73, 29.07, 27.95, 27.71, 24.06, 23.46, 22.99, 18.14, 12.55; HRFAB-MS (thioglycerol matrix) m/e: ([M+H]$^+$) 627.5211 (100%), calcd. 627.5213.

HCl salt of compound 1: Compound 1 was dissolved in a minimum amount of CH$_2$Cl$_2$ and excess HCl in ether was added. Solvent and excess HCl were removed in vacuo and a noncrystalline white powder was obtained. $^1$H NMR (methanol-d4/15% (CDCl$_3$, 300 MHz) δ 7.61-7.57 (m, 2 H), 7.50-7.48 (m, 3 H), 4.84 (bs, 10 H), 4.45 (bs, 1 H), 4.30 (bs, 1 H), 3.96-3.82 (m, 2 H), 3.78-3.69 (m, 2 H), 3.66 (bs, 1 H), 3.59-3.32 (series of multiplets, 4 H), 3.28-3.02 (m, 8 H), 2.81 (s, 3 H), 2.36-2.15 (m, 4 H), 2.02-1.68 (m, 8 H), 1.64-0.90 (series of multiplets, 12 H), 1.01 (d, J=6.35 Hz, 3 H), 0.96 (s, 3 H), 0.73 (s, 3 H); $^{13}$C NMR (methanol-d4/15% (CDCl$_3$, 75 MHz) δ 132.31, 131.20, 130.92, 130.40, 83.13, 81.09, 78.48, 65.54, 64.98, 64.11, 60.87, 57.66, 47.51, 46.91, 43.52, 43.00, 41.38, 41.19, 41.16, 40.75, 40.30, 36.37, 36.08, 36.00, 35.96, 33.77, 29.68, 29.34, 28.65, 28.37, 24.42, 24.25, 23.33, 21.51, 18.80, 13.04.

Compound 2: To a round-bottom flask were added 27 (0.82 g, 1.10 mmol) in dry THF (150 mL) and LiAlH$_4$ (125 mg, 3.30 mmol) under N$_2$. The mixture was stirred at room temperature for 12 hours and Na$_2$SO$_4$.10H$_2$O powder (10 g) was added slowly. After the grey color disappeared, the mixture was filtered through a cotton plug and washed with dry THF. THF was removed in vacuo and the residue dissolved in CH$_2$Cl$_2$ (50 mL). After filtration, the desired product was obtained as a colorless glass (0.73 g, 99% yield). IR (neat) 3362, 2936, 2862, 2786, 1576, 1466, 1363, 1103 cm$^{-1}$; $^1$H NMR (CDCl$_3$, 300 MHz) δ 7.32-7.23 (m, 5 H), 3.67-3.63 (m, 1 H), 3.60-3.57 (m, 1H), 3.53 (t, J=6.4 Hz, 2 H), 3.47 (s, 2 H), 3.46 (bs, 1 H), 3.24-3.17(m, 2 H), 3.12-2.99 (m, 2 H), 2.83-2.74 (series of multiplets, 6 H), 2.30 (t, J=7.3 Hz, 2 H), 2.15 (s, 3 H), 2.20-2.00 (m, 3 H), 1.95-1.51 (series of multiplets, 20 H), 1.51-1.08, (series of multiplets, 10 H), 1.06-0.80 (m, 3 H), 0.87 (d, J=8.1 Hz, 3 H), 0.86 (s, 3 H), 0.61 (s, 3 H); $^{13}$C NMR (CDCl$_3$, 75 MHz).

139.35, 129.16, 128.22, 126.88, 80.44, 79.29, 75.96, 66.70, 66.52, 66.12, 62.45, 58.26, 46.76, 46.27, 42.69, 42.41, 42.02, 40.68, 40.10, 40.02, 39.82, 35.84, 35.47, 35.30, 35.06, 34.15, 34.09, 34.03, 33.80, 28.96, 27.93, 27.75, 27.71, 24.32, 23.53, 23.03, 22.75, 18.17, 12.58; HRFAB-MS (thioglycerol+Na$^+$ matrix) m/e: ([M+Na]$^+$) 691.5504 (38.5%), calcd. 691.5502.

HCl salt of compound 2: Compound 2 was dissolved in a minimum amount of CH$_2$Cl$_2$ and excess HCl in ether was added. Removal of the solvent and excess HCl gave a noncrystalline white powder. $^1$H NMR (methanol-d$_4$/15% (CDCl$_3$, 300 MHz) δ 7.60-7.59 (m, 2 H), 7.50-7.47 (m, 3 H), 4.82 (bs, 10 H), 4.43 (bs, 1 H), 4.32 (bs, 1 H), 3.85-3.79 (m, 1 H), 3.75-3.68 (m, 1 H), 3.64 (t, J=5.74 Hz, 2 H), 3.57 (bs, 1 H), 3.36-3.28 (m, 2 H), 3.25-3.00 (series of multiplets, 10 H), 2.82 (s, 3 H), 2.14-1.68 (series of multiplets, 19 H), 1.65-1.15 (series of multiplets, 11 H), 0.98 (d, J=6.6 Hz, 3 H), 0.95 (s, 3 H), 0.72 (s, 3 H); $^{13}$C NMR (methanol-d4/15% (CDCl$_3$, 75 MHz) δ 132.21, 131.10, 130.58, 130.28, 81.96, 80.72, 77.60, 66.84, 66.58, 66.12, 61.03, 57.60, 44.16, 42.77, 40.62, 39.57, 39.43, 36.28, 36.03, 35.96, 35.78, 33.65, 29.48, 29.27, 29.11, 29.01, 28.61, 28.56, 28.35, 24.56, 23.30, 21.17, 18.64, 12.90.

Compound 4: A suspension of 1 (79.1 mg, 0.126 mmol) and aminoiminomethanesulfonic acid (50.15 mg, 0.404 mmol) in methanol and chloroform was stirred at room temperature for 24 hours, and the suspension became clear. An ether solution of HCl (1 M, 1 mL) was added followed by the removal of solvent with N$_2$ flow. The residue was dissolved in H$_2$O (5 mL) followed by the addition of 20% aqueous NaOH (0.5 mL). The resulting cloudy mixture was extracted with CH$_2$Cl$_2$ (4×5 mL). The combined extracts were dried over anhydrous Na$_2$SO$_4$. Removal of solvent gave the desired product (90 mg, 95%) as white powder. m.p. 111-112° C. IR (neat) 3316, 2937, 1667, 1650, 1556, 1454, 1348, 1102 cm$^{-1}$; $^1$H NMR (5% methanol-d4/CDCl$_3$, 300 MHz) δ 7.26-7.22 (m, 5 H), 4.37 (bs, 3 H), 3.71-3.51(series of multiplets, 5 H), 3.44 (s, 2 H), 3.39-3.10 (series of multiplets, 10 H), 2.27 (t, J=6.83 Hz, 2 H), 2.13 (s, 3 H), 2.02-0.94 (series of multiplets, 33 H), 0.85 (d, J=5.62 Hz, 3 H), 0.84 (s, 3 H), 0.61 (s, 3 H); $^{13}$C NMR (5% methanol-d4/CDCl$_3$, 75 MHz) δ 158.54, 158.48, 158.43, 138.27, 129.47, 128.32, 127.19, 81.89, 80.30, 77.34, 69.02, 68.46, 67.21, 62.36, 58.00, 47.36, 46.18, 43.26, 43.00, 42.73, 42.18, 41.48, 39.32, 35.55, 34.97, 34.89, 34.67, 33.63, 28.93, 28.28, 27.53, 27.16, 23.96, 23.28, 23.16, 22.77, 18.36, 12.58; HRFAB-MS (thioglycerol+Na$^+$ matrix) m/e: ([M+H]$^+$) 753.5858 (100%), calcd. 753.5867.

HCl salt of compound 4: Compound 4 was dissolved in minimum amount of CH$_2$Cl$_2$ and MeOH followed by addition of excess HCl in ether. The solvent was removed by N$_2$ flow, and the residue was subjected to high vacuum overnight. The desired product was obtained as noncrystalline white powder. $^1$H NMR (methanol-d4/20% (CDCl$_3$, 300 MHz) δ 7.58 (bs, 2 H), 7.50-7.48 (m, 3 H), 4.76 (bs, 13 H), 4.45 (d, J=12.9 Hz, 1 H), 4.27 (dd, 1 H, J=12.9, 5.4 Hz), 3.82-3.00 (series of multiplets, 17 H), 2.81-2.80 (m, 3 H), 2.20-1.02 (series of multiplets, 27 H), 0.98 (d, J=6.59 Hz, 3 H), 0.95 (s, 3 H), 0.72 (s, 3 H); $^{13}$C NMR (methanol-d4/20% CDCl$_3$, 75 MHz) δ 158.88, 158.72, 132.00, 131.96, 130.98, 130.15, 82.51, 81.07, 78.05, 68.50, 68.02, 67.94, 67.10, 60.87, 60.53, 57.38, 47.16, 46.91, 43.91, 43.11, 43.01, 42.91, 42.55, 40.28, 39.88, 39.95, 35.90, 35.73, 35.64, 33.53, 29.18, 28.35, 27.99, 24.02, 23.30, 21.35, 18.52, 18.44, 13.06.

Compound 5: A suspension of 2 (113 mg, 0.169 mmol) and aminoiminomethanesulfonic acid (67.1 mg, 0.541 mmol) in methanol and chloroform was stirred at room temperature for 24 hours. HCl in ether (1 M, 1 mL) was added followed by the removal of solvent with N$_2$ flow. The residue was subject to high vacuum overnight and dissolved in H$_2$O (5 mL) followed by the addition of 20% NaOH solution (1.0 mL). The resulting mixture was extracted with CH$_2$Cl$_2$ (5×5 mL). The combined extracts were dried over anhydrous Na$_2$SO$_4$. Removal of solvent gave desired the product (90 mg, 95% yield) as a white solid. m.p. 102-104° C. IR (neat) 3332, 3155, 2939, 2863, 1667, 1651, 1558, 1456, 1350, 1100 cm$^{-1}$; $^1$H NMR (5% methanol-d4/CDCl$_3$, 300 MHz) δ 7.35-7.24 (m, 5 H), 3.75-3.64 (m, 1 H), 3.57 (bs, 5 H), 3.50 (s, 2 H), 3.53-3.46 (m, 1 H), 3.40-3.10 (series of multiplets, 14 H), 2.34 (t, J=7.31 Hz, 2 H), 2.19 (s, 3 H), 2.13-0.96 (series of multiplets, 36 H), 0.91 (bs, 6 H), 0.66 (s, 3 H); $^{13}$C NMR (5% methanol-d4/CDCl$_3$, 75 MHz) δ 157.49, 157.31, 157.23, 138.20, 129.52, 128.34, 127.23, 81.17, 79.19, 76.42, 65.63, 65.03, 64.70, 62.36, 58.02, 47.23, 46.24, 42.89, 42.18, 41.45, 39.45, 39.40, 39.30, 38.71, 35.61, 35.55, 35.02, 34.82, 33.69, 29.87, 29.59, 29.42, 28.84, 27.96, 27.56, 23.95, 23.40, 22.82, 22.64, 18.28, 12.54; HRFAB-MS (thioglycerol+Na$^+$ matrix) m/e: ([M+H]$^+$) 795.6356 (84.3%), calcd. 795.6337.

HCl salt of compound 5: Compound 5 was dissolved in minimum amount of CH$_2$Cl$_2$ and MeOH followed by the addition of excess HCl in ether. The solvent and excess HCl were removed by N$_2$ flow and the residue was subject to high vacuum overnight. The desired product was obtained as noncrystalline white powder. $^1$H NMR (methanol-d4/10% CDCl$_3$, 300 MHz) δ 7.62-7.54 (m, 2 H), 7.48-7.44 (m, 3 H), 4.84 (bs, 16 H), 4.46 (d, J=12.7 Hz, 1 H), 4.26 (dd, J=12.7, 3.42 Hz, 1 H), 3.78-3.56 (series of multiplets, 5 H), 3.38-3.05 (series of multiplets, 13 H), 2.80 (d, 3 H), 2.19-2.04 (m, 3 H), 2.02-1.04 (series of multiplets, 30 H), 0.98 (d, J=6.35 Hz, 3 H), 0.95 (s, 3 H), 0.72 (s, 3 H); $^{13}$C NMR (methanol-d4/10% CDCl$_3$, 75 MHz) δ 158.75, 158.67, 132.32, 131.24, 130.83, 130.43, 82.49, 81.02, 77.60, 66.47, 65.93, 61.19, 60.85, 57.69, 47.79, 47.60, 44.29, 43.07, 40.86, 40.42, 40.19, 40.09, 39.76, 36.68, 36.50, 36.15, 35.94, 33.91, 30.75, 30.46, 29.74, 29.33, 28.71, 24.41, 24.03, 23.38, 22.21, 22.16, 18.59, 18.52, 13.09.

Compound CSA-26 was synthesized according to Scheme 1 and Example 1 using 7-deoxycholic acid in place of cholic acid and methyl cholate.

Example 2

This example includes a description of one or more exemplary synthetic procedures for obtaining Compounds 3, 28 and 29.

Compound 28: A suspension of 19 (0.641 g, 0.614 mmol) and KCN (0.40 g, 6.14 mmol) in anhydrous DMSO (5 mL) was stirred under $N_2$ at 80° C. overnight followed by the addition of $H_2O$ (50 mL). The aqueous mixture was extracted with EtOAc (4×20 mL). The combined extracts were washed with brine once, dried over anhydrous $Na_2SO_4$ and concentrated in vacuo. The residue was dissolved in $CH_2Cl_2$ (3 mL) and MeOH (3 mL) and catalytic amount of p-toluenesulfonic acid (5.84 mg, 0.03 mmol) was added. The solution was stirred at room temperature for 3 hours before the introduction of saturated $NaHCO_3$ solution (10 mL). After the addition of brine (60 mL), the mixture was extracted with EtOAc (4×30 mL). The combined extracts were washed with brine once and dried over anhydrous $Na_2SO_4$ and concentrated. The residue afforded the desired product (0.342 g, 92% yield) as pale yellowish oil after column chromatography (silica gel, EtOAc/hexanes 2:1). IR (neat) 3479, 2936, 2864, 2249, 1456, 1445, 1366, 1348, 1108 $cm^{-1}$; $^1H$ NMR ($CDCl_3$, 300 MHz) δ 3.76-3.53 (m, 7 H), 3.32-3.06 (series of multiplets, 4 H), 2.57-2.46 (m, 6 H), 2.13-1.00 (series of multiplets, 31 H), 0.93 (d, J=6.35 Hz, 3 H), 0.90 (s, 3 H), 0.67 (s, 3 H); $^{13}C$ NMR ($CDCl_3$, 75 MHz) δ 119.91, 119.89, 80.75, 79.65, 76.29, 65.83, 65.37, 65.19, 63.63, 46.57, 46.44, 42.77, 41.79, 39.71, 35.63, 35.26, 35.02, 32.00, 29.46, 29.03, 27.96, 27.74, 26.64, 26.42, 26.12, 23.56, 22.98, 22.95, 18.24, 14.65, 14.54, 14.30, 12.60; HRFAB-MS (thioglycerol+$Na^+$ matrix) m/e: ([M+$Na]^+$) 618.4247 (67.8%), calcd. 618.4247.

Compound 29: To a solution of 28 (0.34 g, 0.57 mmol) in dry $CH_2Cl_2$ (15 mL) under $N_2$ at 0° C. was added $NEt_3$ (119.5 μL, 0.857 mmol) followed by the addition of mesyl chloride (53.1 .mu.L, 0.686 mmol). The mixture was allowed to stir at 0° C. for 30 minutes before the addition of $H_2O$ (6 mL). After the introduction of brine (60 mL), the aqueous mixture was extracted with EtOAc (4×20 mL). The combined extracts were washed with brine once, dried over anhydrous $Na_2SO_4$ and concentrated. To the residue was added N-benzylmethyl amine (0.5 mL) and the mixture was stirred under $N_2$ at 80° C. overnight. Excess N-benzylmethylamine was removed in vacuo and the residue was subject to column chromatography (silica gel, EtOAc/hexanes 2:1 followed by EtOAc) to afford product (0.35 g, 88% yield) as a pale yellow oil. IR (neat) 2940, 2863, 2785, 2249, 1469, 1453, 1366, 1348, 1108 $cm^{-1}$; $^1H$ NMR ($CDCl_3$, 300 MHz) δ 7.34-7.21 (m, 5 H), 3.76-3.69 (m, 1 H), 3.64-3.50 (m, 4 H), 3.48 (s, 2 H), 3.31-3.05 (series of multiplets, 4 H), 2.52-2.46 (m, 6 H), 2.33 (t, J=7.32 H, 2 Hz), 2.18 (s, 3 H), 2.13-0.95 (series of multiplets, 30 H), 0.91 (d, J=6.80 H, 3 Hz), 0.90 (s, 3 H), 0.66 (s, 3 H); $^{13}C$ NMR ($CDCl_3$, 75 MHz) δ 139.37, 129.17, 128.26, 126.93, 119.96, 119.91, 80.73, 79.59, 76.26, 65.79, 65.35, 65.13, 62.47, 58.25, 46.74, 46.40, 42.72, 42.38, 41.76, 39.68, 35.78, 35.22, 34.98, 33.79, 28.99, 27.92, 27.71, 26.63, 26.38, 26.09, 24.21, 23.54, 22.96, 22.90, 18.28, 14.62, 14.51, 14.26, 12.58; HRFAB-MS (thioglycerol+$Na^+$ matrix) m/e: ([M+$H]^+$) 699.5226 (100%), calcd. 699.5213.

Compound 3: A solution of 29 (0.074 g, 0.106 mmol) in anhydrous THF (10 mL) was added dropwise to a mixture of $AlCl_3$ (0.1414 g, 1.06 mmol) and $LiAlH_4$ (0.041 g, 1.06 mmol) in dry THF (10 mL). The suspension was stirred for 24 hours followed by the addition of 20% NaOH aqueous solution (2 mL) at ice-bath temperature. Anhydrous $Na_2SO_4$ was added to the aqueous slurry. The solution was filtered and the precipitate washed twice with THF. After removal of solvent, the residue was subject to column chromatography (silica gel, MeOH/$CH_2Cl_2$ 1:1 followed by MeOH/$CH_2Cl_2$/$NH_3.H_2O$ 4:4:1) to afford the desired product (0.038 g, 50% yield) as a clear oil. IR (neat) 3362, 2935, 2863, 2782, 1651, 1574, 1568, 1557, 1471, 1455, 1103 $cm^{-1}$; $^1H$ NMR ($CDCl_3$, 300 MHz) δ 7.32-7.22 (m, 5 H), 3.60-3.02 (series of broad multiplets, 18 H), 2.90-2.70 (m, 5 H), 2.33 (t, J=7.20 Hz, 2 H), 2.24-2.04 (m, 3 H), 2.18 (s, 3 H), 1.96-0.96 (series of multiplets, 30 H), 0.90 (d, J=7.57 Hz, 3 H), 0.89 (s, 3 H), 0.64 (s, 3 H); $^{13}C$ NMR ($CDCl_3$, 75 MHz) δ 139.44, 129.24, 128.31, 126.97, 80.63, 79.65, 75.97, 68.44, 68.00, 67.96, 62.54, 58.40, 46.77, 46.30, 42.73, 42.43, 42.07, 41.92, 41.74, 41.72, 39.81, 35.82, 35.48, 35.07, 33.84, 31.04, 30.30, 30.10, 29.03, 28.11, 27.82, 27.81, 27.74, 27.67, 27.64, 24.31, 23.50, 23.04, 22.93, 18.22, 12.63; HRFAB-MS (thioglycerol+$Na^+$ matrix) m/e: ([M+$H]^+$) 711.6139 (100%), calcd. 711.6152;([M+$Na]^+$) 733.5974 (46.1%), calcd. 733.5972.

Example 3

This example includes a description of one or more exemplary synthetic procedures for obtaining Compounds 6, 7 and 30-33.

Compound 30: Cholic acid (3.0 g, 7.3 mmol) was dissolved in $CH_2Cl_2$ (50 mL) and methanol (5 mL). Dicyclohexylcarbodiimide (DCC) (1.8 g, 8.8 mmol) was added followed by N-hydroxysuccinimide (about 100 mg) and benzylmethylamine (1.1 g, 8.8 mmol). The mixture was stirred for 2 hours, then filtered. The filtrate was concentrated and chromatographed ($SiO_2$, 3% MeOH in $CH_2Cl_2$) to give 3.0 g of a white solid (81% yield). m.p. 184-186° C.; IR (neat) 3325, 2984, 1678 $cm^{-1}$; $^1H$ NMR ($CDCl_3$, 200 MHz) δ 7.21 (m, 5 H), 4.51 (m, 2 H), 3.87 (m, 1 H), 3.74 (m, 2 H), 3.36 (m, 2 H), 2.84 (s, 3 H), 2.48-0.92 (series of multiplets, 28 H), 0.80 (s, 3 H), 0.58 (d, J=6.5 Hz, 3 H); $^{13}C$ NMR ($CDCl_3$, 50 MHz) δ 174.30, 173.94, 137.36, 136.63, 128.81, 128.46, 127.85, 127.50, 127.18, 126.28, 72.96, 71.76, 68.35, 53.39, 50.65, 48.77, 46.91, 46.33, 41.44, 39.36, 39.18, 35.76, 35.27, 34.76, 33.87, 31.54, 34.19, 31.07, 30.45, 28.11, 27.63, 26.14, 25.59, 24.92, 23.26, 17.51, 12.41; FAB-MS (thioglycerol+$Na^+$ matrix) m/e: ([M+$H]^+$) 512 (100%), calcd. 512.

Compound 31: Compound 30 (2.4 g, 4.7 mmol) was added to a suspension of $LiAlH_4$ (0.18 g, 4.7 mmol) in THF (50 mL). The mixture was refluxed for 24 hours, then cooled to 0° C. An aqueous solution of $Na_2SO_4$ was carefully added until the grey color of the mixture dissipated. The salts were filtered out, and the filtrate was concentrated in vacuo to yield 2.1 g of a white solid (88%). The product proved to be of sufficient purity for further reactions. m.p. 70-73° C.; IR (neat) 3380, 2983, 1502 $cm^{-1}$; $^1H$ NMR ($CDCl_3$, 300 MHz) δ 7.23 (m, 5 H), 3.98 (bs, 2 H), 3.81 (m, 3 H), 3.43 (m, 3 H), 2.74 (m, 2 H), 2.33 (m, 3 H), 2.25 (s, 3 H), 2.10-0.90 (series of multiplets, 24 H), 0.98 (s, 3 H), 0.78 (s, 3 H); $^{13}C$ NMR ($CDCl_3$, 75 MHz) δ 135.72, 129.63, 128.21, 128.13, 125.28, 72.91, 71.63, 62.05, 60.80, 56.79, 47.00, 46.23, 41.44, 40.81, 39.41, 35.42, 35.24, 34.63, 34.02, 33.22, 31.73, 30.17, 29.33, 29.16, 28.02, 27.49, 26.17, 25.55, 23.10, 22.48, 22.33, 17.54, 12.65; FAB-MS (thioglycerol matrix) m/e: ([M+$H]^+$) 498 (100%), calcd. 498.

Compound 32: Compound 31 (0.36 g, 0.72 mmol) was dissolved in $CH_2Cl_2$ (15 mL) and Bocglycine (0.51 g, 2.89 mmol), DCC (0.67 g, 3.24 mmol) and dimethylaminopyridine (DMAP) (about 100 mg) were added. The mixture was stirred under $N_2$ for 4 hours then filtered. After concentration and chromatography ($SiO_2$, 5% MeOH in $CH_2Cl_2$), the product was obtained as a 0.47 g of a clear glass (68%). $^1$H NMR ($CDCl_3$, 300 MHz) δ 7.30 (m, 5 H), 5.19 (bs, 1 H), 5.09 (bs, 3 H), 5.01 (bs, 1 H), 4.75 (m, 1 H), 4.06-3.89 (m, 6 H), 2.33 (m, 2 H), 2.19 (s, 3 H) 2.05-1.01 (series of multiplets, 26 H), 1.47 (s, 9 H), 1.45 (s, 18 H), 0.92 (s, 3 H), 0.80 (d, J=6.4 Hz, 3 H), 0.72 (s, 3 H). $^3$C NMR ($CDCl_3$, 75 MHz) δ 170.01, 169.86, 169.69, 155.72, 155.55, 139.90, 129.05, 128.17, 126.88, 79.86, 76.53, 75.09, 72.09, 62, 35, 57.88, 47.78, 45.23, 43.12, 42.79, 42.16, 40.81, 37.94, 35.51, 34.69, 34.57, 34.36, 33.30, 31.31, 29.66, 28.80, 28.34, 27.22, 26.76, 25.61, 24.02, 22.83, 22.47, 17.93, 12.19; FAB-MS (thioglycerol matrix) m/e: ([M+H]$^+$) 970 (100%), calcd. 970.

Compound 33: Compound 31 (0.39 g, 0.79 mmol) was dissolved in $CH_2Cl_2$ (15 mL) and Boc-β-alanine (0.60 g, 3.17 mmol), DCC (0.73 g, 3.56 mmol) and dimethylaminopyridine (DMAP) (about 100 mg) were added. The mixture was stirred under $N_2$ for 6 hours then filtered. After concentration and chromatography ($SiO_2$, 5% MeOH in $CH_2Cl_2$), the product was obtained as a 0.58 g of a clear glass (72%). IR (neat) 3400, 2980, 1705, 1510 cm$^{-1}$; $^1$H NMR ($CDCl_3$, 300 MHz) δ 7.27 (m, 5 H), 5.12 (bs, 4 H), 4.93 (bs, 1 H), 4.71 (m, 1 H), 3.40 (m, 12 H), 2.59-2.48 (m, 6 H), 2.28 (m, 2 H), 2.17 (s, 3 H), 2.05-1.01 (series of multiplets, 26 H), 1.40 (s, 27 H), 0.90 (s, 3 H), 0.77 (d, J=6.1 Hz, 3 H), 0.70 (s, 3 H). $^{13}$C NMR ($CDCl_3$, 75 MHz) δ 171.85, 171.50, 171.44, 155.73, 138.62, 129.02, 128.09, 126.87, 79.18, 75.53, 74.00, 70.91, 62.20, 57.67, 47.84, 44.99, 43.28, 41.98, 40.73, 37.67, 36.12, 34.94, 34.65, 34.47, 34.20, 33.29, 31.23, 29.57, 28.74, 28.31, 28.02, 27.86, 27.12, 26.73, 25.46, 24.86, 23.95, 22.77, 22.39, 17.91, 12.14; HRFAB-MS (thioglycerol+Na$^+$ matrix) m/e: ([M+H]$^+$) 1011.6619 (100%), calcd. 1011.6634.

Compound 6: Compound 32 (0.15 g, 0.15 mmol) was stirred with excess 4 N HCl in dioxane for 40 minutes. The dioxane and HCl were removed in vacuo leaving 0.12 g of a clear glass (about 100%). $^1$H NMR ($CD_3OD$, 300 MHz) δ 7.62 (bs, 2 H), 7.48 (bs, 3 H), 5.30 (bs, 1 H), 5.11 (bs, 1 H), 4.72 (bs (1 H), 4.46 (m, 1 H), 4.32 (m, 1H) 4.05-3.91 (m, 4 H), 3.10 (m, 2 H), 2.81 (s, 3 H), 2.15-1.13 (series of multiplets, 25 H), 1.00 (s, 3 H), 0.91 (bs, 3 H), 0.82 (s, 3 H). $^{13}$C NMR ($CD_3OD$, 125 MHz) δ 166.86, 166.50, 131.09, 130.18, 129.17, 128.55, 76.60, 75,43, 72.61, 72.04, 70.40, 66.22, 60.07, 58.00, 57.90, 54.89, 54.76, 46.44, 44.64, 43.39, 42.22, 38.56, 36.78, 34.14, 33.92, 33.84, 31.82, 30.54, 29.67, 28.79, 27.96, 26.79, 26.00, 24.99, 23.14, 22.05, 21.82, 19.91, 17.27, 11.60; HRFAB-MS (thioglycerol+Na$^+$ matrix) m/e: ([M-4 Cl-3 H]$^+$) 669.4576 (100%), calcd. 669.4591.

Compound 7: Compound 33 (0.20 g, 0.20 mmol) was stirred with excess 4 N HCl in dioxane for 40 minutes. The dioxane and HCl were removed in vacuo leaving 0.12 g of a clear glass (about 100%). $^1$H NMR ($CD_3OD$, 500 MHz) δ 7.58 (bs, 2 H), 7.49 (bs, 3 H), 5.21 (bs, 1 H), 5.02 (bs, 1 H), 4.64 (m, 1 H), 4.44 (m, 1 H), 4.28 (m, 1 H), 3.30-2.84 (m, 14 H), 2.80 (s, 3 H), 2.11-1.09 (series of multiplets, 25 H), 0.99 (s, 3 H), 0.89 (d, J=4.1 Hz, 3 H), 0.80 (s, 3 H); $^{13}$C NMR ($CD_3OD$, 125 MHz) δ 171.92, 171.56, 171.49, 132.44, 131.32, 131.02, 130.51, 78.13, 76.61, 61.45, 57.94, 46.67, 44.80, 42.36, 40.85, 39.33, 37.03, 36.89, 36.12, 36.09, 35.79, 35.63, 33.81, 33.10, 32.92, 32.43, 30.28, 28.43, 28.04, 26.65, 24.02, 22.86, 21.98, 18.70, 12.68; HRFAB-MS (thioglycerol+Na$^+$ matrix) m/e: ([M-4 Cl-3 H]$^+$) 711.5069 (43%), calcd. 711.5061.

Example 4

This example includes a description of one or more exemplary synthetic procedures for obtaining Compounds 8, CSA-7, CSA-8 and 34-40.

Compound 34: Diisopropyl azodicarboxylate (DIAD) (1.20 mL, 6.08 mmol) was added to triphenylphosphine (1.60 g, 6.08 mmol) in THF (100 mL) at 0° C. and was stirred for half an hour during which time the yellow solution became a paste. Compound 14 (2.58 g, 4.06 mmol) and p-nitrobenzoic acid (0.81 g, 4.87 mmol) were dissolved in THF (50 mL) and added to the paste. The resulted mixture was stirred at ambient temperature overnight. Water (100 mL) was added and the mixture was made slightly basic by adding $NaHCO_3$ solution followed by extraction with EtOAc (3×50 mL). The combined extracts were washed with brine once and dried over anhydrous $Na_2SO_4$. The desired product (2.72 g, 85% yield) was obtained as white powder after $SiO_2$ chromatography ($Et_2O$/hexanes 1:2). m.p. 207-209° C.; IR (KBr) 3434, 3056, 2940, 2868, 1722, 1608, 1529, 1489, 1448, 1345 cm$^{-1}$; $^1$H NMR ($CDCl_3$, 300 MHz) δ 8.30-8.26 (m, 2 H), 8.21-8.16 (m, 2 H), 7.46-7.42 (m, 6 H), 7.31-7.18 (m, 9 H)5.33 (bs, 1 H), 4.02 (bs, 1 H), 3.90 (bs, 1 H), 3.09-2.97 (m, 2 H), 2.68 (td, J=14.95, 2.56 Hz, 1 H), 2.29-2.19 (m, 1 H), 2.07-1.06 (series of multiplets, 24 H), 1.01 (s, 3 H), 0.98 (d, J=6.6 Hz, 3 H), 0.70 (s, 3 H); $^{13}$C NMR ($CDCl_3$, 75 MHz) δ 164.21, 150.56, 144.70, 136.79, 130.77, 128.88, 127.86, 126.98, 123.70, 86.47, 73.24, 73.00, 68.70, 64.22, 47.79, 46.79, 42.15, 39.76, 37.47, 35.52, 35.34, 34.23, 33.79, 32.46, 31.12, 28.74, 27.71, 26.85, 26.30, 25.16, 23.41, 17.98, 12.77; HRFAB-MS (thioglycerol+Na$^+$ matrix) m/e: ([M+Na]$^+$) 808.4203 (53.8%), calcd. 808.4189. Nitrobenzoate (2.75 g, 3.5 mmol) was dissolved in $CH_2Cl_2$ (40 mL) and MeOH (20 mL) and 20% aqueous NaOH (5 mL) were added. The mixture was heated up to 60° C. for 24 hours. Water (100 mL) was introduced and extracted with EtOAc. The combined extracts were washed with brine and dried over anhydrous $Na_2SO_4$. The desired product (1.89 g, 85% yield) was obtained as white solid after $SiO_2$ chromatography (3% MeOH in $CH_2Cl_2$ as eluent). m.p. 105-106° C.; IR (KBr) 3429, 3057, 2936, 1596, 1489, 1447, 1376, 1265, 1034, 704 cm$^{-1}$; $^1$H NMR ($CDCl_3$, 300 MHz) δ 7.46-7.42 (m, 6 H), 7.32-7.19 (m, 9 H), 4.06 (bs, 1 H), 3.99 (bs, 1 H), 3.86 (bd, J=2.44 Hz, 1 H), 3.09-2.97 (m, 2 H), 2.47 (td, J=14.03, 2.44 Hz, 1 H), 2.20-2.11 (m, 1 H), 2.04-1.04 (series of multiplets, 25 H), 0.97 (d, J=6.59 Hz, 3 H), 0.94 (s, 3 H), 0.68 (s, 3 H); $^{13}$C NMR ($CDCl_3$, 75 MHz) δ 144.70, 128.88, 127.86, 126.97, 86.45, 73.31, 68.84, 67.10, 64.23, 47.71, 46.74, 42.10, 39.70, 36.73, 36.73, 36.15, 35.53, 35.45, 34.45, 32.46, 29.93, 28.67, 27.86, 27.71, 26.87, 26.04, 23.43, 23.16, 17.94, 12.75; HRFAB-MS (thioglycerol+Na$^+$ matrix) m/e: ([M+Na]$^+$) 659.4064 (100%), calcd. 659.4076.

Compound 35: To a round-bottom flask were added 34 (2.0 g, 3.14 mmol), NaH (60% in mineral oil, 3.8 g, 31.4 mmol) and THF (150 mL). The suspension was refluxed for 2 hours followed by the addition of allyl bromide (2.72 mL, 31.4 mL). After refluxing for 28 hours, another 10 eq. of NaH and allyl bromide were added. After 72 hours, another 10 eq. of NaH and allyl bromide were added. After 115 hours, TLC showed almost no starting material or intermediates. Water (100 mL) was added to the suspension carefully, followed by extraction with EtOAc (5×50 mL). The combined extracts were washed with brine and dried over anhydrous $Na_2SO_4$. The desired product (1.81 g, 79% yield) was obtained as a yellowish glass after $SiO_2$ chromatography (5% EtOAc/hexanes). IR (neat) 3060, 3020, 2938, 2865, 1645, 1596, 1490, 1448, 1376, 1076, 705 cm$^{-1}$; $^1$H NMR ($CDCl_3$, 300 MHz) δ 7.46-7.42 (m, 6 H), 7.31-7.18 (m, 9 H), 6.06-5.85 (m, 3 H), 5.35-5.20 (m, 3 H), 5.15-5.06 (m, 3 H), 4.10-4.00 (m, 2 H), 3.93-3.90 (m, 2 H), 3.85-3.79 (ddt, J=13.01, 4.88, 1.59 Hz, 1 H), 3.73-3.66 (ddt, J=13.01, 5.38, 1.46 Hz, 1 H), 3.58 (bs, 1 H), 3.54 (bs, 1 H), 3.32 (d, J=2.93 Hz, 1 H), 3.07-2.96 (m, 2 H), 2.36 (td, J=13.67, 2.68 Hz, 1 H), 2.24-2.10 (m, 2 H), 2.03-1.94 (m, 1 H), 1.87-0.86 (series of multiplets, 20 H), 0.91 (s, 3 H), 0.90 (d, J=6.83 Hz, 3 H), 0.64 (s, 3 H); $^{13}$C NMR (CDCl$_3$, 75 MHz) δ 144.77, 136.29, 136.21, 136.13, 128.90, 127.86, 126.94, 116.13, 115.51, 115.42, 86.44, 81.11, 75.65, 73.92, 69.40, 68.81, 64.43, 46.68, 46.54, 42.93, 39.93, 36.98, 35.66, 35.14, 35.14, 32.83, 32.54, 30.48, 28.51, 27.72, 27.64, 26.82, 24.79, 23.65, 23.43, 23.40, 18.07, 12.80; HRFAB-MS (thioglycerol+Na$^+$ matrix) m/e: ([M+H]$^+$) 757.5185 (12.9%), calcd. 757.5196.

Compound 36: Ozone was bubbled through a solution of 35 (0.551 g, 0.729 mmol) in CH$_2$Cl$_2$ (40 mL) and MeOH (20 mL) at −78° C. until the solution turned a deep blue. Excess ozone was blown off with oxygen. Methylsulfide (1 mL) was added followed by the addition of NaBH$_4$ (0.22 g, 5.80 mmol) in 5% NaOH solution and methanol. The resulted mixture was stirred overnight at room temperature and washed with brine. The brine was then extracted with EtOAc (3×20 mL). The combined extracts were dried over Na$_2$SO$_4$. The desired product (0.36 g, 65% yield) was obtained as a colorless glass after SiO$_2$ chromatography (5% MeOH/CH$_2$Cl$_2$). IR (neat) 3396, 3056, 2927, 1596, 1492, 1462, 1448, 1379, 1347, 1264, 1071 cm$^{-1}$; $^1$H NMR (CDCl$_3$, 300 MHz) δ 7.46-7.42 (m, 6 H), 7.32-7.18 (m, 9 H), 3.77-3.57 (series of multiplets, 10 H), 3.48-3.44 (m, 2 H), 3.36-3.30 (m, 2 H), 3.26-3.20 (m, 1 H), 3.04-2.99 (m, 2 H), 2.37-0.95 (series of multiplets, 27 H), 0.92 (s, 3 H), 0.91 (d, J=6.59 Hz, 3 H), 0.67 (s, 3 H); $^{13}$C NMR (CDCl$_3$, 75 MHz) δ 144.69, 128.87, 127.84, 126.94, 86.44, 81.05, 76.86, 74.65, 69.91, 69.22, 68.77, 64.24, 62.44, 62.42, 62.26, 46.92, 46.54, 42.87, 39.73, 36.86, 35.52, 35.13, 32.82, 32.54, 30.36, 28.71, 27.61, 27.44, 26.79, 24.82, 23.51, 23.38, 23.31, 18.28, 12.74; HRFAB-MS (thioglycerol+Na$^+$ matrix) m/e: ([M+Na]$^+$) 791.4844 (96.4%), calcd. 791.4863.

Compound 37: NEt$_3$ (0.23 mL, 1.66 mmol) was added to a solution of 36 (0.364 g, 0.47 mmol) in dry CH$_2$Cl$_2$ (30 mL) at 0° C. under N$_2$ followed by the introduction of mesyl chloride (0.12 mL, 1.56 mmol). The mixture was stirred for 10 minutes and H$_2$O (10 mL) added to quench the reaction, followed by extraction with EtOAc (3×30 mL). The combined extracts were washed with brine and dried over anhydrous Na$_2$SO$_4$. SiO$_2$ chromatography (EtOAc/hexanes 1:1) gave the desired product (0.411 g, 86% yield) as white glass. IR (neat) 3058, 3029, 2939, 2868, 1491, 1461, 1448, 1349, 1175, 1109, 1019 cm$^{-1}$; $^1$H NMR (CDCl$_3$, 300 MHz) δ 7.46-7.42 (m, 6 H), 7.31-7.19 (m, 9 H), 4.35-4.26 (m, 6 H), 3.84-3.74 (m, 2 H), 3.64-3.56 (m, 4 H), 3.49-3.34 (m, 3 H), 3.06 (s, 3 H), 3.04 (s, 3 H), 3.02 (s, 3 H), 3.09-2.95 (m, 2 H), 2.28 (bt, J=14.89 Hz, 1 H), 2.09-0.86 (series of multiplets, 21 H), 0.92 (s, 3 H), 0.90 (d, J=6.78 Hz, 3 H), 0.66 (s, 3 H); $^{13}$C NMR (CDCl$_3$, 75 MHz) δ 144.66, 128.86, 127.86, 126.97, 86.46, 81.28, 77.18, 75.00, 70.14, 69.89, 69.13, 66.49, 65.85, 65.72, 64.22, 47.06, 46.35, 42.77, 39.58, 37.81, 37.64, 37.55, 36.75, 35.48, 35.02, 32.59, 32.52, 30.27, 28.43, 27.56, 27.52, 26.92, 24.62, 23.34, 23.25, 23.10, 18.24, 12.64; HRFAB-MS (thioglycerol+Na$^+$ matrix) m/e: ([M+Na]$^+$) 1025.4207 (100%), calcd. 1025.4189.

Compound 38: The suspension of 37 (0.227 g, 0.227 mmol) and NaN$_3$ (0.147 g, 2.27 mmol) in dry DMSO (5 mL) was stirred at 80° C. overnight, diluted with H$_2$O (50 mL) and extracted with EtOAc (3×20 mL). The extracts were washed with brine once and dried over anhydrous Na$_2$SO$_4$. SiO$_2$ chromatography (EtOAc/hexanes 1:8) afforded the desired product (0.153 g, 80% yield) as a yellow oil. IR (neat) 2929, 2866, 2105, 1490, 1466, 1448, 1107, 705 cm$^{-1}$; $^1$H NMR (CDCl$_3$, 300 MHz) δ 7.46-7.42 (m, 6 H), 7.32-7.19 (m, 9 H), 3.80-3.74 (m, 1 H), 3.70-3.55 (series of multiplets, 5 H), 3.41-3.19 (series of multiplets, 9 H), 3.04-2.98 (m, 2 H), 2.41 (td, J=13.1, 2.44 Hz, 1 H), 2.29-2.14 (m, 2 H), 2.04-0.86 (series of multiplets, 20 H), 0.93 (s, 3 H), 0.91 (d, J=6.60 Hz, 3 H), 0.66 (s, 3 H); $^{13}$C NMR (CDCl$_3$, 75 MHz) δ 144.78, 128.93, 127.87, 126.96, 86.46, 81.30, 77.16, 75.21, 67.99, 67.44, 67.03, 64.41, 51.64, 51.57, 51,33, 46.71, 46.30, 42.35, 39.75, 36.72, 35.64, 35.20, 32.52, 32.42, 30.17, 28.63, 27.80, 27.22, 26.90, 24.80, 23.55, 23.30, 23.24, 18.23, 12.65; HRFAB-MS (thioglycerol+Na$^+$ matrix) m/e: ([M+Na]$^+$) 866.5049 (96.9%), calcd. 866.5057.

Compound 39: p-Toluenesulfonic acid (1.72 mg) was added into the solution of 38 (0.153 g, 0.18 mmol) in CH$_2$Cl$_2$ (5 mL) and MeOH (5 mL), and the mixture was stirred for 2.5 hours. Saturated NaHCO$_3$ solution (5 mL) was introduced followed by the introduction of brine (30 mL). The aqueous mixture was extracted with EtOAc and the combined extracts washed with brine and dried over Na$_2$SO$_4$. The desired product (0.10 g, 92% yield) was obtained as a pale yellowish oil after SiO$_2$ chromatography (EtOAc/hexanes 1:3). IR (neat) 3426, 2926, 2104, 1467, 1441, 1347, 1107 cm$^{-1}$; $^1$H NMR (CDCl$_3$, 300 MHz) δ 3.81-3.74 (m, 1 H), 3.71-3.54 (m, 7 H), 3.41-3.19 (m, 9 H), 2.41 (td, J=13.61, 2.32 Hz, 1 H), 2.30-2.14 (m, 2 H), 2.07-1.98 (m, 1H), 1.94-0.95 (series of multiplets, 21 H), 0.95 (d, J=6.35 Hz, 3 H), 0.93 (s, 3 H), 0.69 (s, 3 H); $^{13}$C NMR (CDCl$_3$, 75 MHz) δ 81.22, 77.08, 75.13, 67.94, 67.36, 66.97, 63.76, 51.59, 51.51, 51.26, 46.51, 46.24, 42.31, 39.68, 36.64, 35.58, 35.12, 32.34, 31.92, 30.11, 29.55, 28.54, 27.82, 27.16, 24.75, 23.47, 23.23, 23.18, 18.15, 12.56; HRFAB-MS (thioglycerol+Na$^+$ matrix) m/e: ([M+Na]$^+$) 624.3966 (54.9%), calcd. 624.3962.

Compound 40: To a solution of 39 (0.10 g, 0.166 mmol) in CH$_2$Cl$_2$ (8 mL) at 0° C. was added NEt$_3$ (34.8 μL, 0.25 mmol) under N$_2$ followed by the introduction of mesyl chloride (15.5 .mu.L, 0.199 mmol). The mixture was stirred 15 minutes. Addition of H$_2$O (3 mL) and brine (20 mL) was followed by extraction with EtOAc (4×10 mL). The combined extracts were washed with brine once and dried over Na$_2$SO$_4$. After removal of solvent, the residue was mixed with N-benzylmethylamine (0.5 mL) and heated to 80° C. under N$_2$ overnight. Excess N-benzyl methylamine was removed in vacuo and the residue was subjected to SiO$_2$ chromatography (EtOAc/hexanes 1:4) to give the product (0.109 g, 93% yield) as a yellow oil. IR (neat) 2936, 2784, 2103, 1467, 1442, 1346, 1302, 1106, 1027 cm$^{-1}$; $^1$H NMR (CDCl$_3$, 300 MHz) δ 7.32-7.23 (m, 5 H), 3.81-3.74 (m, 1 H), 3.71-3.55 (m, 5 H), 3.47 (s, 2 H), 3.41-3.19 (m, 9 H), 2,46-2.11 (m, 5 H), 2.18 (s, 3 H), 2.03-0.85 (series of multiplets, 20 H), 0.93 (s, 3 H), 0.93 (d, J=6.35 Hz, 3 H,), 0.67 (s, 3 H); $^{13}$C NMR (CDCl$_3$, 75 MHz) δ 139.54, 129.26, 128.32, 126.97, 81.26, 77.12, 75.17, 67.98, 67.42, 67.00, 62.50, 58.41, 51.61, 51.54, 51.29, 46.66, 46.28, 42.46, 42.32, 39.72, 36.68, 35.76, 35.16, 33.75, 32.38, 30.15, 28.59, 27.85, 27.19, 24.77, 24.15, 23.53, 23.28, 23.22, 18.28, 12.60; HRFAB-MS (thioglycerol+Na$^+$ matrix) m/e: ([M+H]$^+$) 705.4929 (100%), calcd. 705.4928.

Compound 8: A suspension of 40 (0.109 g, 0.155 mmol) and LiAlH$_4$ (23.5 mg, 0.62 mmol) in THF (20 mL) was stirred under N$_2$ overnight. Na$_2$SO$_4$.10H$_2$O was carefully added and stirred until no grey color persisted. Anhydrous Na$_2$SO$_4$ was added and the white precipitate was filtered out and rinsed with dry THF. After removal of solvent, the residue was dissolved in minimum CH$_2$Cl$_2$ and filtered. The desired product (0.091 g, 94% yield) was obtained as a colorless oil after the solvent was removed. IR (neat) 3371, 3290, 3027, 2938, 2862, 2785, 1586, 1493, 1453, 1377, 1347, 1098 cm$^{-1}$; $^1$H NMR (CDCl$_3$, 300 MHz) δ 7.31-7.21 (m, 5 H), 3.65-3.53 (m, 4 H), 3.47 (s, 2 H), 3.42-3.34 (m, 2 H), 3.30 (bs, 1 H), 3.26-3.20 (m, 1H), 3.14-3.09 (m, 1 H), 2.89-2.81 (m, 6 H), 2.39-2.27 (m, 3 H), 2.17 (s, 3 H), 2.15-0.88 (series of multiplets, 29 H), 0.93 (d, J=6.59 Hz, 3 H), 0.92 (s, 3 H), 0.67 (s, 3 H); $^{13}$C NMR (CDCl$_3$, 75 MHz) δ 139.34, 129.16, 128.24, 126.90, 80.75, 76.44, 74.29, 70.58, 69.88, 69.75, 62.47, 58.27, 46.66, 46.47, 42.75, 42.63, 42.51, 42.35, 39.77, 36.87, 35.73, 35.04, 33.77, 32.90, 30.38, 28.71, 27.70, 27.32, 24.89, 24.09, 23.53, 23.36, 23.25, 18.24, 12.62; HRFAB-MS (thioglycerol+Na$^+$ matrix) m/e: ([M+H]$^+$) 627.5199 (23.3%), calcd. 627.5213.

Compound CSA-7: To a solution of 23 (0.18 g, 0.28 mmol) in dry DMF (4 mL) were added NaH (0.224 g, 60% in mineral oil, 5.60 mmol) and 1-bromo octane (0.48 mL, 2.80 mmol). The suspension was stirred under N$_2$ at 65° C. overnight followed by the introduction of H$_2$O (60 mL) and extraction with ether (4×20 mL). The combined extracts were washed with brine and dried over Na$_2$SO$_4$. SiO$_2$ chromatography (hexanes and 5% EtOAc in hexanes) afforded the desired product (0.169 g, 80% yield) as a pale yellowish oil. IR (neat) 2927, 2865, 2099, 1478, 1462, 1451, 1350, 1264, 1105 cm$^{-1}$; $^1$H NMR (CDCl$_3$, 300 MHz) δ 3.69-3.35 (series of multiplets, 15 H), 3.26-3.02 (series of multiplets, 4 H), 2.19-2.02 (m, 3 H), 1.97-1.16 (series of multiplets, 37 H), 1.12-0.99 (m, 3 H), 0.92-0.86 (m, 9 H), 0.65 (s, 3 H); $^{13}$C NMR (CDCl$_3$, 75 MHz) δ 80.69, 79.84, 76.13, 71.57, 71.15, 65.07, 64.49, 64.39, 49.08, 48.99, 48.80, 46.68, 46.45, 42.72, 42.05, 39.88, 35.74, 35.49, 35.36, 35.14, 32.42, 32.03, 30.01, 29.85, 29.81, 29.76, 29.67, 29.48, 29.14, 27.92, 27.80, 27.70, 26.58, 26.42, 23.59, 23.09, 22.92, 22.86, 18.11, 14.31, 12.65; HRFAB-MS (thioglycerol+Na$^+$ matrix) m/e: ([M+Na]$^+$) 778.5685 (22.1%), calcd. 778.5683. The triazide (0.169 g, 0.224 mmol) and LiAlH$_4$ (0.025 g, 0.67 mmol) were suspended in anhydrous THF (10 mL) and stirred under N$_2$ at room temperature overnight followed by careful introduction of Na$_2$SO$_4$ hydrate. After the grey color disappeared, anhydrous Na$_2$SO$_4$ was added and stirred. The white precipitate was removed by filtration and washed with THF. After removal of solvent, the residue was dissolved in 1 M hydrochloric acid and the aqueous solution was extracted with ether (5 mL) once. The aqueous solution was then made basic by adding 20% aqueous NaOH solution followed by extraction with Et$_2$O (4×5 mL). The combined extracts were washed, dried and concentrated. The residue was then subject to SiO$_2$ chromatography (MeOH/CH$_2$Cl$_2$ (1:1) followed by MeOH/CH$_2$Cl$_2$/NH$_3$.H$_2$O (4:4:1)) to afford the desired product (0.091 g, 60% yield) as a colorless oil. IR (neat) 3361, 2927, 2855, 1576, 1465, 1351, 1105 cm$^{-1}$; $^1$H NMR (CD$_3$OD, 300 MHz) δ 4.86 (bs, 6 H), 3.77-3.72 (m, 3 H), 3.70-3.61 (m,1 H), 3.57-3.53 (m, 3 H), 3.43-3.38 (m, 4 H), 3.34-3.27 (m, 2 H), 3.18-3.10 (m, 2 H), 2.84-2.71 (m, 6 H), 2.22-2.07 (m, 3 H), 2.00-1.02 (series of multiplets, 39 H), 0.97-0.88 (m, 9 H), 0.71 (s, 3 H); $^{13}$C NMR (CD$_3$OD, 75 MHz) δ 82.20, 81.00, 77.62, 72.52, 72.06, 68.00, 67.92, 67.39, 48.20, 47.53, 44.26, 43.40, 41.42, 41.15, 40.84, 40.35, 36.88, 36.73, 36.42, 36.11, 34.24, 34.05, 33.94, 33.67, 33.17, 30.95, 30.72, 30.62, 29.81, 29.35, 28.87, 28.79, 27.51, 24.57, 23.90, 23.83, 23.44, 18.76, 14.62, 13.07; HRFAB-MS (thioglycerol matrix) m/e: ([M+H]$^+$) 678.6133 (100%), calcd. 678.6149.

Compound CSA-8: A suspension of 23 (0.126 g, 0.196 mmol) and LiAlH$_4$ (0.037 g, 0.98 mmol) in THF (40 mL) was stirred at room temperature under N$_2$ overnight followed by careful addition of Na$_2$SO$_4$.10H$_2$O. After the grey color in the suspension disappeared, anhydrous Na$_2$SO$_4$ was added and stirred until organic layer became clear. The white precipitate was removed by filtration and washed with twice THF. The THF was removed in vacuo, and the residue was subject to SiO$_2$ chromatography (MeOH/CH$_2$Cl$_2$/NH$_3$/H$_2$O (4:4:1)) to afford the desired product (0.066 g, 60% yield) as a colorless oil. IR (neat) 3365, 2933, 2865, 1651, 1471, 1455, 1339, 1103 cm$^{-1}$; $^1$H NMR (CDCl$_3$/30% CD$_3$OD, 300 MHz) δ 4.43 (bs, 7 H), 3.74-3.68 (m, 1 H), 3.66-3.60 (m, 1 H), 3.57-3.50 (m, 5 H), 3.34-3.25 (M, 2 H), 3.17-3.06 (M, 2 H), 2.84-2.74 (M, 6 H), 2.19-2.01 (M, 3 H), 1.97-0.96 (series of multiplets, 27 H), 0.94 (d, J=7.2 Hz, 3 H), 0.92 (s, 3 H), 0.69 (s, 3 H); $^{13}$C NMR (CDCl$_3$, 75 MHz) δ 80.44, 79.27, 75.77, 66.59, 66.53, 65.86, 62.51, 46.21, 45.84, 42.55, 41.53, 40.09, 39.43, 39.31, 39.02, 35.16, 34.93, 34.86, 34.57, 32.93, 32.71, 31.57, 28.66, 28.33, 27.64, 27.22, 23.04, 22.40, 22.29, 17.60, 11.98; HRFAB-MS (thioglycerol+Na$^+$ matrix) m/e: ([M+H]$^+$) 566.4889 (8.9%), calcd. 566.4897.

Example 5

This example includes a description of one or more exemplary synthetic procedures for obtaining Compounds CSA-11 and 43-47.

Compound 43: Precursor compound 41 was prepared following the method reported by D. H. R. Barton, J. Wozniak, S. Z. Zard, Tetrahedron, 1989, vol. 45, 3741-3754. A mixture of 41 (1.00 g, 2.10 mmol), ethylene glycol (3.52 mL, 63 mmol) and p-TsOH (20 mg, 0.105 mmol) was refluxed in benzene under N$_2$ for 16 hours. Water formed during the reaction was removed by a Dean-Stark moisture trap. The cooled mixture was washed with NaHCO$_3$ solution (50 mL) and extracted with Et$_2$O (50 mL, 2×30 mL). The combined extracts were washed with brine and dried over anhydrous Na$_2$SO$_4$. Removal of the solvent gave the product (1.09 g, 100%) as a white glass. IR (neat) 2939, 2876, 1735, 1447, 1377, 1247, 1074, 1057, 1039 cm$^{-1}$; $^1$H NMR (CDCl$_3$, 300 MHz) δ 5.10 (t, J=2.70 Hz, 1 H), 4.92 (d, J=2.69 Hz, 1 H), 4.63-4.52 (m, 1 H), 3.98-3.80 (m, 4 H), 2.323 (t, J=9.51 Hz, 1 H), 2.13 (s, 3 H), 2.08 (s, 3 H), 2.05 (s, 3 H), 2.00-1.40 (series of multiplets, 15 H), 1.34-0.98 (m, 3 H), 1.20 (s, 3 H), 0.92 (s, 3 H), 0.82 (s, 3 H); $^{13}$C NMR (CDCl$_3$, 75 MHz) δ 170.69, 170.63, 170.47, 111.38, 75.07, 74.23, 70.85, 64.95, 63.43, 49.85, 44.73, 43.39, 41.11, 37.37, 34.84, 34.80, 34.52, 31.42, 29.18, 27.02, 25.41, 24.16, 22.72, 22.57, 22.44, 21.73, 21.63, 13.40; HRFAB-MS (thioglycerol+Na$^+$ matrix) m/e: ([M+H]$^+$) 521.3106 (38.6%), calcd. 521.3114. The triacetate (1.09 g, 2.10 mmol) was dissolved in MeOH (50 mL). NaOH (0.84 g, 21 mmol) was added to the solution. The suspension was then refluxed under N$_2$ for 24 hours. MeOH was then removed in vacuo and the residue was dissolved in Et$_2$O (100 mL) and washed with H$_2$0, brine, and then dried over anhydrous Na$_2$SO$_4$. The desired product (0.80 g, 96% yield) was obtained as white solid after removal of solvent. m.p. 199-200° C. IR (neat) 3396, 2932, 1462, 1446, 1371, 1265, 1078, 1055 cm$^{-1}$; $^1$H NMR (10% CD$_3$OD in CDCl$_3$, 300 MHz) δ 4.08-3.83 (series of multiplets, 9 H), 3.44-3.34 (m, 1 H), 2.41 (t, J=9.28 Hz, 1 H), 2.22-2.10 (m, 2 H), 1.96-1.50 (series of multiplets, 12 H), 1.45-0.96 (series of multiplets, 4 H), 1.32 (s, 3 H), 0.89 (s, 3 H), 0.78 (s, 3 H); $^{13}$C NMR (10% CD$_3$OD in CDCl$_3$, 75 MHz) δ 112.11, 72.35, 71.57, 68.09, 64.54, 63.24, 49.36, 45.90, 41.48, 41.45, 39.18, 38.79, 35.29, 34.71, 34.45, 29.90, 27.26, 26.60, 23.65, 22.54, 22.44, 22.35, 13.46; HRFAB-MS (thioglycerol+Na$^+$ matrix) m/e: ([M+Na]$^+$) 417.2622 (87.3%), calcd. 417.2617.

Compound 44: To a round-bottom flask were added 43 (0.80 g, 2.03 mmol) and dry THF (100 mL) followed by the addition of NaH (60% in mineral oil, 0.81 g, 20.3 mmol). The suspension was refluxed under N$_2$ for 30 minutes before the addition of allyl bromide (1.75 mL, 20.3 mmol). After 48 hours of reflux, another 10 eq. of NaH and allyl bromide were added. After another 48 hours, TLC showed no intermediates left. Cold water (50 mL) was added to the cooled suspension. The resulted mixture was extracted with $Et_2O$ (60 mL, 2×30 mL). The combined extracts were washed with brine and dried over anhydrous $Na_2SO_4$. $SiO_2$ column chromatography (6% EtOAc in hexanes) gave the desired product (0.94 g, 90% yield) as a pale yellow oil. IR (neat) 3076, 2933, 2866, 1645, 1446, 1423, 1408, 1368, 1289, 1252, 1226, 1206, 1130, 1080, 1057 $cm^{-1}$; $^1H$ NMR ($CDCl_3$, 300 MHz) δ 6.02-5.84 (m, 3 H), 5.31-5.04 (m, 6 H), 4.12-4.05 (m, 2 H), 4.01-3.81 (m, 7 H), 3.70 (dd, J=12.94, 5.62 Hz, 1 H), 3.55 (t, J=2.56 Hz, 1 H), 3.33 (d, J=2.93 Hz, 1 H), 3.18-3.08 (m, 1 H), 2.65 (t, J=10.01 Hz, 1 H), 2.32-2.14 (m, 3 H), 1.84-1.45 (series of multiplets, 10 H), 1.41-1.22 (m, 3 H), 1.27 (s, 3 H), 1.14-0.92 (m, 2 H), 0.89 (s, 3 H), 0.75 (s, 3 H); $^{13}C$ NMR ($CDCl_3$, 75 MHz) δ 136.38, 136.07, 136.00, 116.31, 115.54, 115.38, 112.34, 80.07, 79.22, 75.05, 69.83, 69.34, 68.82, 65.14, 63.24, 48.80, 45.96, 42.47, 42.15, 39.40, 35.55, 35.16, 35.15, 29.04, 28.22, 27.52, 24.21, 23.38, 23.11, 22.95, 22.58, 13.79; HRFAB-MS (thioglycerol+$Na^+$ matrix) m/e: ([M+Na]$^+$) 537.3549 (100%), calcd. 537.3556.

Compound 45: To the solution of 44 (0.94 g, 1.83 mmol) in dry THF (50 mL) was added 9-BBN (0.5 M solution in THF, 14.7 mL, 7.34 mmol) and the mixture was stirred under $N_2$ at room temperature for 12 hours before the addition of 20% NaOH solution (4 mL) and 30% $H_2O_2$ solution (4 mL). The resulted mixture was then refluxed for an hour followed by the addition of brine (100 mL) and extracted with EtOAc (4×30 mL). The combined extracts were dried over anhydrous $Na_2SO_4$. After the removal of solvent, the residue was purified by $SiO_2$ column chromatography (EtOAc followed by 10% MeOH in $CH_2Cl_2$) to give the product (0.559 g, 54% yield) as a colorless oil. IR (neat) 3410, 2933, 2872, 1471, 1446, 1367, 1252, 1086 $cm^{-1}$; $^1H$ NMR ($CDCl_3$, 300 MHz) δ 4.02-3.52 (series of multiplets, 17 H), 3.41-3.35 (m, 1 H), 3.29 (d, J=2.44 Hz, 1 H), 3.22-3.15 (m, 3 H), 2.58 (t, J=10.01 Hz, 1 H), 2.27-1.95 (m, 3 H), 1.83-1.48 (series of multiples, 16 H), 1.40-0.93 (series of multiplets, 5 H), 1.27 (s, 3 H), 0.90 (s, 3 H), 0.75 (s, 3 H); $^{13}C$ NMR ($CDCl_3$, 75 MHz) δ 112.41, 80.09, 79.09, 76.31, 66.70, 66.02, 65.93, 64.80, 63.26, 61.53, 61.25, 60.86, 48.59, 45.80, 42.51, 41.72, 39.10, 35.36, 35.02, 34.98, 32.87, 32.52, 32.40, 28.88, 27.94, 27.21, 24.33, 23.02, 22.84 (2 C's), 22.44, 13.69; HRFAB-MS (thioglycerol+$Na^+$ matrix) m/e: ([M+Na]$^+$) 591.3881 (100%), calcd. 591.3873.

Compound 46: To a solution of 45 (0.559 g, 0.98 mmol) in acetone (40 mL) and water (4 mL) was added PPTS (0.124 g, 0.49 mmol) and the solution was refluxed under $N_2$ for 16 hours. The solvent was removed under reduced pressure. Water (40 mL) was then added to the residue and the mixture was extracted with EtOAc (40 mL, 2×20 mL). The combined extracts were washed with brine, dried and evaporated to dryness. $SiO_2$ column chromatography (8% MeOH in $CH_2Cl_2$) of the residue afforded the desired product (0.509 g, 98% yield) as clear oil. IR (neat) 3382, 2941, 2876, 1699, 1449, 1366, 1099 $cm^{-1}$; $^1H$ NMR ($CDCl_3$, 300 MHz) δ 3.83-3.72 (m, 8 H), 3.66 (t, J=5.62 Hz, 2 H), 3.54 (bs, 2 H), 3.43-3.28 (m, 4 H), 3.24-3.12 (m, 2 H), 2.26-2.00 (m, 4 H), 2.08 (s, 3 H), 1.98-1.50 (series of multiplets, 15 H), 1.42-0.96 (series of multiplets, 6 H), 0.90 (s, 3 H), 0.62 (s, 3 H); $^{13}C$ NMR ($CDCl_3$, 75 MHz) δ 210.49, 78.87 (2 C's), 76.30, 66.86, 66.18, 65.69, 61.74, 61.43, 60.71, 55.31, 48.05, 43.02, 41.58, 39.53, 35.28, 35.09, 34.96, 32.77, 32.70, 32.31, 31.12, 28.72, 27.88, 27.14, 23.47, 22.75, 22.47, 22.34, 13.86; HRFAB-MS (thioglycerol+$Na^+$ matrix) m/c: ([M+Na]$^+$) 547.3624 (100%), calcd. 547.3611.

Compound 47: To a solution of 46 (0.18 g, 0.344 mmol) in dry $CH_2Cl_2$ (10 mL) at 0° C. was added $Et_3N$ (0.168 mL, 1.20 mmol) followed by the addition of mesyl chloride (0.088 mL, 1.13 mmol). After 10 minutes, $H_2O$ (3 mL) and brine (30 mL) were added. The mixture was extracted with EtOAc (30 mL, 2×10 mL) and the extracts were washed with brine and dried over anhydrous $Na_2SO_4$. After removal of solvent, the residue was dissolved in DMSO (5 mL) and $NaN_3$ (0.233 g, 3.44 mmol). The suspension was heated up to 50° C. under $N_2$ for 12 hours. $H_2O$ (50 mL) was added to the cool suspension and the mixture was extracted with EtOAc (30 mL, 2×10 mL) and the extracts were washed with brine and dried over anhydrous $Na_2SO_4$. $SiO_2$ column chromatography (EtOAc/hexanes 1:5) afforded the product (0.191 g, 88% yield for two steps) as a pale yellow oil. IR (neat) 2933, 2872, 2096, 1702, 1451, 1363, 1263, 1102 $cm^{-1}$; $^1H$ NMR ($CDCl_3$, 300 MHz) δ 3.72-3.64 (m, 2 H), 3.55-3.24 (series of multiplets, 1I1 H), 3.18-3.02 (m, 2 H), 2.22-2.02 (m, 4 H), 2.08 (s, 3 H), 1.95-1.46 (series of multiplets, 15 H), 1.28-0.96 (series of multiplets, 6 H), 0.89 (s, 3 H), 0.62 (s, 3 H); $^{13}C$ NMR ($CDCl_3$, 75 MHz) δ 210.36, 79.69, 79.22, 75.98, 65.08, 64.80, 64.53, 55.31, 48.93, 48.86, 48.76, 48.06, 43.03, 41.91, 39.66, 35.44, 35.31, 35.12, 31.04, 29.77, 29.69, 29.67, 28.99, 28.10, 27.65, 23.60, 22.99, 22.95, 22.50, 14.00; HRFAB-MS (thioglycerol+$Na^+$ matrix) m/e: ([M+Na]$^+$) 622.3820 (100%), calcd. 622.3805.

Compound CSA-11: Compound 47 (0.191 g, 0.319 mmol) was dissolved in dry THF (20 mL) followed by the addition of $LiAlH_4$ (60.4 mg, 1.59 mmol). The grey suspension was stirred under $N_2$ at room temperature for 12 hours. $Na_2SO_4.10H_2O$ powder was carefully added. After the grey color in the suspension disappeared, anhydrous $Na_2SO_4$ was added and the precipitate was filtered out. After the removal of solvent, the residue was purified by column chromatography (silica gel, MeOH/$CH_2Cl_2$/28% $NH_3.H_2O$ 3:3:1). After most of the solvent was rotavapped off from the fractions collected, 5% HCl solution (2 mL) was added to dissolve the milky residue. The resulted clear solution was then extracted with $Et_2O$ (2×10 mL). 20% NaOH solution was then added until the solution became strongly basic. $CH_2Cl_2$ (20 mL, 2×10 mL) was used to extract the basic solution. The combined extracts were dried over anhydrous $Na_2SO_4$ and removal of solvent gave the desired product (0.115 g, 69% yield) as a colorless oil. From $^1H$ NMR it appears that this compound was a mixture of two stereoisomers at $C_{20}$ with a ratio of approximately 9:1. The stereoisomers were not separated, but used as recovered. Spectra for the most abundant isomer: IR (neat) 3353, 2926, 2858, 1574, 1470, 1366, 1102 $cm^{-1}$; $^1H$ NMR (20% $CDCl_3$ in $CD_3OD$, 300 MHz) δ 4.69 (bs, 7 H), 3.76-3.69 (m, 1 H), 3.63-3.53 (m, 5 H), 3.50-3.40 (m, 1 H), 3.29 (bs, 1 H), 3.18-3.07 (m, 2 H), 2.94-2.83 (m, 1 H), 2.81-2.66 (m, 5 H), 2.23-2.06 (m, 4 H), 1.87-1.50 (series of multiplets, 15 H), 1.39-0.96 (series of multiplets, 6 H), 1.11 (d, J=6.10 Hz, 3 H), 0.93 (s, 3 H), 0.75 (s, 3 H); $^{13}C$ NMR (20% $CDCl_3$ in $CD_3OD$, 75 MHz) δ 81.46, 80.67, 77.32, 70.68, 67.90, 67.66, 67.18, 50.32, 47.17, 43.30, 43.06, 40.74, 40.64, 40.38, 40.26, 36.31, 36.28, 35.93, 34.30, 34.02, 33.29, 29.63, 29.31, 28.43, 26.10, 24.67, 24.09, 23.96, 23.50, 13.30 for the major isomer; HRFAB-MS (thioglycerol+$Na^+$ matrix) m/e: ([M+H]$^+$) 524.4431 (64.2%), calcd. 524.4427.

Example 6

This example includes a description of one or more exemplary synthetic procedures for obtaining Compounds CSA-10 and 48-49

Compound 48: To a solution of 23 (0.15 g, 0.233 mmol) in dry $CH_2Cl_2$ (15 mL) at 0° C. was added $Et_3N$ (48.8 μL, 0.35 mmol) followed by the addition of $CH_3SO_2Cl$ (21.7 μL, 0.28 mmol). The mixture was stirred for 15 minutes before $H_2O$ (3 mL) was added. Saturated NaCl solution (20 mL) was then added, and the mixture was extracted with EtOAc (40 mL, 2×20 mL). The combined extracts were washed with brine and dried over anhydrous $Na_2SO_4$. The solvent was rotovapped off and to the residue were added NaBr (0.12 g, 1.17 mmol) and DMF (10 mL). The suspension was heated up to 80° C. under $N_2$ for 2 hours. DMF was removed under vacuum and the residue was chromatographed on silica (EtOAc/hexanes 1:10) to give the desired product (0.191 g, 97% yield) as a pale yellow oil. $^1$H NMR ($CDCl_3$, 300 MHz) δ 3.69-3.35 (series of multiplets, 13 H), 3.28-3.02 (series of multiplets, 4 H), 2,18-2.04 (m, 3 H), 2.00-1.60 (series of multiplets, 16 H), 1.58-0.96 (series of multiplets, 11 H), 0.92 (d, J=6.34 Hz, 3 H), 0.89 (s, 3 H), 0.66 (s, 3 H); $^{13}$C NMR ($CDCl_3$, 75 MHz) δ 80.62, 79.81, 76.08, 65.07, 64.50, 64.34, 49.03, 48.98, 48.79, 46.49, 46.46, 42.73, 42.02, 39.85, 35.47, 35.34, 35.12, 34.79, 34.72, 29.82, 29.80, 29.74, 29.11, 27.91, 27.78, 27.69, 23.55, 23.07, 22.88, 18.10, 12.62; HRFAB-MS (thioglycerol+$Na^+$ matrix) m/e: ([M−H]$^+$) 706.3609 (63.1%), calcd. 706.3591; 704.3616 (52.8%), calcd. 704.3611.

Compound 49: Compound 48 (0.191 g, 0.269 mmol) and 23 (0.295 g, 0.459 mmol) was dissolved in DMF (3 mL, distilled over BaO at 6 mm Hg before use) followed by the addition of NaH (0.054 g, 60% in mineral oil). The suspension was stirred under $N_2$ at room temperature for 24 hours. $H_2O$ (100 mL) was added to quench excess NaH and the mixture was then extracted with $Et_2O$ (40 mL, 3×20 mL) and the combined extracts were washed with brine and dried over anhydrous $Na_2SO_4$. The desired product (0.177 g, 52% yield based on compound 23) was obtained as a pale yellow oil after $SiO_2$ chromatography (EtOAc/hexanes 1:6, then 1:2). IR (neat) 2940, 2862, 2095, 1472, 1456, 1362, 1263, 1113 cm$^{-1}$; $^1$H NMR($CDCl_3$, 300 MHz) δ 3.68-3.35 (series of multiplets, 26 H), 3.28-3.02 (series of multiplets, 8 H), 2.20-2.04 (m, 6 H), 1.96-1.60 (series of multiplets, 30 H), 1.52-0.98 (series of multiplets, 12 H), 0.91 (d, J=6.59 Hz, 6 H), 0.89 (s, 6 H), 0.65 (s, 6 H); $^{13}$C NMR($CDCl_3$, 75 MHz) δ 80.68, 79.83, 76.13, 71.71, 65.06, 64.48, 64.39, 49.08, 48.98, 48.80, 46.64, 46.44, 42.71, 42.04, 39.88, 35.73, 35.49, 35.36, 35.14, 32.41, 29.84, 29.81, 29.76, 29.14, 27.92, 27.78, 27.69, 26.58, 23.59, 23.08, 22.92, 18.12, 12.64.

Compound CSA-10: Compound 49 (0.219 g, 0.173 mmol) was dissolved in dry THF (10 mL) followed by the addition of LiAlH$_4$ (65 mg, 1.73 mmol). The grey suspension was stirred under $N_2$ at room temperature for 12 hours. $Na_2SO_4.10H_2O$ powder was carefully added. After the grey color in the suspension disappeared, anhydrous $Na_2SO_4$ was added and the precipitate was filtered out. After the removal of solvent, the residue was purified by column chromatography (silica gel, MeOH/$CH_2Cl_2$/28% $NH_3.H_2O$ 2.5:2.5:1). After most of the solvent was rotavapped off from the fractions collected, 5% HCl solution (2 mL) was added to dissolve the milky residue. The resulted clear solution was then extracted with $Et_2O$ (2×10 mL). 20% NaOH solution was then added until the solution became strongly basic. $CH_2Cl_2$ (20 mL, 2×10 mL) was used to extract the basic solution. The combined extracts were dried over anhydrous $Na_2SO_4$ and removal of solvent gave the desired product (0.147 g, 76% yield) as a white glass. IR (neat) 3364, 3287, 2934, 2861, 1596, 1464, 1363, 1105 cm$^{-1}$; $^1$H NMR (20% $CDCl_3$ in $CD_3OD$, 500 MHz) δ 4.74 (bs, 12 H), 3.75-3.70 (m, 2 H), 3.65-3.61 (m, 2 H), 3.57-3.52 (m, 6 H), 3.40 (t, J=3.60 Hz, 4 H), 3.30 (bs, 4 H), 3.16-3.10 (m, 4 H), 2.84-2.73 (m, 12 H), 2.18-2.07 (m, 6 H), 1.97-1.61 (series of multiplets, 30 H), 1.58-0.98 (series of multiplets, 24 H), 0.95 (d, J=6.84 Hz, 6 H), 0.94 (s, 6 H), 0.70 (s, 6 H); $^{13}$C NMR (20% $CDCl_3$ in $CD_3OD$, 125 MHz) δ 81.70, 80.52, 77.09, 72.34, 67.75 (2 C's), 67.07, 47.80, 47.13, 43.76, 42.87, 41.20, 40.65, 40.58, 40.14, 36.43, 36.25, 36.08, 35.77, 34.15, 33.87 (2 C's), 33.18, 29.55, 28.92, 28.47, 28.42, 27.25, 24.27, 23.54, 23.41, 18.70, 13.07; HRFAB-MS (thioglycerol+$Na^+$ matrix) m/e: ([M+H]$^+$) 1113.9625 (68.8%), calcd. 1113.9610.

Example 7

This example includes a description of one or more exemplary synthetic procedures for obtaining Compounds 111-113 and 116a-d.

Compounds 116a-d: Representative procedure: preparation of 116b. NaH (0.06 g, 60% in mineral oil, 1.49 mmol) and propyl bromide (0.136 mL, 1.49 mmol) were added to a DMF solution of compound 23 (described in Li et al., J. Am. Chem. Soc. 1998, 120, 2961) (0.096 g, 0.149 mmol). The suspension was stirred under $N_2$ for 24 hr. $H_2O$ (20 mL) was added, and the mixture was extracted with hexanes (3×10 mL). The combined extracts were dried over $Na_2SO_4$ and concentrated in vacuo. Silica gel chromatography (10% EtOAc in hexanes) afforded the desired product (92 mg, 90% yield) as a pale yellow oil. $^1$H NMR ($CDCl_3$, 500 MHz) δ 3.68-3.64 (m, 1 H), 3.61-3.57 (m, 1 H), 3.52 (t, J=6.1 Hz, 2 H), 3.49 (bs, 1 H), 3.46-3.35 (m, 10 H), 3.25 (d, J=2.4 Hz, 1 H), 3.23-3.19 (m, 1 H), 3.16-3.11 (m, 1 H), 3.09-3.03 (m, 1 H), 2.17-2.03 (m, 3 H), 1.95-1.55 (m, 17 H), 1.51-1.40 (m, 4 H), 1.38-1.17 (m, 5 H), 1.11-0.96 (m, 3 H), 0.93-0.89 (m, 9 H), 0.65 (s, 3 H); $^{13}$C NMR ($CDCl_3$, 75 MHz) δ 80.64, 79.79, 76.08, 72.67, 71.59, 65.01, 64.44, 64.33, 49.04, 48.94, 48.75, 46.61, 46.40, 42.68, 42.00, 39.83, 35.72, 35.45, 35.30, 35.10, 32.38, 29.81, 29.77, 29.72, 29.09, 27.88, 27.76, 27.65, 26.52, 23.55, 23.12, 23.04, 22.87, 18.06, 12.60, 10.79; HRFAB-MS (thioglycerol+$Na^+$ matrix) m/e: ([M+Na]$^+$) 708.4910 (23.5%), calcd. 708.4920.

Compounds 111, CSA-17, and 113: Representative procedure: preparation of CSA-17.

Compound 116b (0.092 g, 0.134 mmol) was dissolved in THF (10 mL) followed by the addition of LiAlH$_4$ (0.031 g, 0.81 mmol). The suspension was stirred under $N_2$ for 12 hr. $Na_2SO_4.10H_2O$ (about 1 g) was then carefully added. After the gray color in the suspension dissipated, anhydrous $Na_2SO_4$ was added, and the precipitate was removed by filtration. Concentration and silica gel chromatography ($CH_2Cl_2$/MeOH/28% $NH_3.H_2O$ 12: 6:1, then 10:5:1) yielded a glass which was dissolved in 1 M HCl (2 mL). The resulting clear solution was washed with $Et_2O$ (2×10 ml.). 20% NaOH solution was added to the aqueous phase until the solution became strongly basic. $CH_2Cl_2$ (3×10 mL) was used to extract the basic solution. The combined extracts were dried over anhydrous $Na_2SO_4$ and concentrated in vacuo to give the desired product (0.045 g, 55% yield) as a white glass. $^1$H NMR (about 20% $CDCl_3$ in $CD_3OD$, 500 MHz) δ 4.73 (bs, 6 H), 3.74-3.70 (m, 1 H), 3.65-3.61 (m, 1 H), 3.55 (t, J=6.3 Hz, 2 H), 3.42-3.38 (m, 4 H), 3.33-3.30 (m, 2 H), 3.16-3.10 (m, 2 H), 2.83-2.73 (m, 6 H), 2.18-2.06 (m, 3 H), 1.96-1.20 (series of multiplets, 26 H), 1.12-0.98 (m, 3 H), 0.95-0.92 (m, 9 H), 0.70 (s, 3 H); $^{13}$C NMR (about 20% $CDCl_3$ in $CD_3OD$, 75 MHz) δ 81.67, 80.49, 77.04, 73.44, 72.28, 67.77, 67.71, 67.06, 47.74, 47.08, 43.75, 42.82, 41.21, 40.60, 40.56, 40.12, 36.47, 36.19, 36.04, 35.74, 34.09, 33.82, 33.78, 33.16, 29.49, 28.87, 28.43, 27.18, 24.22, 23.66, 23.49, 23.40, 18.64, 13.04, 11.03; HRFAB-MS (thioglycerol+$Na^+$ matrix) m/e: ([M+H]$^+$) 608.5348 (100%), calcd. 608.5330. 111: $^1$H NMR (about 20% $CDCl_3$ in $CD_3OD$, 500 MHz) δ 4.79 (bs, 6H), 3.74-3.71 (m, 1 H), 3.66-3.62 (m, 1 H), 3.55 (t, J=6.1 Hz, 2 II), 3.52 (bs, 1 II), 3.38-3.28 (series of multiplets, 4 H), 3.33 (s, 3 H), 3.16-3.10 (m, 2H), 2.83-2.72 (m, 6 H), 2.19-2.07 (m, 3 H), 1.97-1.62 (series of multiplets, 15 H), 1.58-1.20 (series of multiplets, 9 H), 1.13-0.98 (m, 3 H), 0.95 (d, J=6.3 Hz, 3 H), 0.93 (s, 3 H), 0.70 (s, 3 H); $^{13}$C NMR (about 20% CDCl$_3$ in CD$_3$OD, 75 MHz) δ 81.82, 80.65, 77.20, 74.43, 67.85, 67.18, 58.90, 47.80, 47.22, 43,91, 43.01, 41.31, 40.78, 40.69, 40.22, 36.63, 36.35, 36.18, 35.86, 34.27, 33.97, 33.26, 29.60, 29.03, 28.58, 28.53, 27.14, 24.33, 23.61, 23.45, 18.68, 13.06; HRFAB-MS (thioglycerol+Na$^+$ matrix) m/e: ([M+Na]$^+$) 602.4855 (100%), calcd. 602.4873. 113: $^1$H NMR (about 50% CDCl$_3$ in CD$_3$OD, 500 MHz) δ 4.08 (bs, 6 H), 3.71-3.67 (m, 1 H), 3.62-3.58 (m, 1 H), 3.53 (t, J=6.3 Hz, 2 H), 3.49 (bs, 1 H), 3.43-3.38 (m, 4 H), 3.31-3.27 (m, 2 H), 3.14-3.07 (m, 2 H), 2.83-2.73 (m, 6 H), 2.16-2.03 (m, 3 H), 1.93-1.17 (series of multiplets, 30 H), 1.10-0.96 (m, 3 H), 0.93-0.89 (m, 9 H), 0.67 (s, 3 H); $^{13}$C NMR (about 50% CDCl$_3$ in CD$_3$OD, 75 MHz) δ 80.51, 79.35, 75.85, 71.29, 70.83, 66.73, 66.62, 65.96, 46.68, 45.98, 42.59, 41.63, 40.20, 39.53, 39.43, 39.21, 35.34, 35.04, 35.00, 34.71, 33.11, 32.90, 32.82, 32.00, 29.15, 28.49, 28.15, 27.75, 27.35, 26.22, 23.18, 22.60, 22.45, 22.34, 17.77, 13.75, 12.22; HRFAB-MS (thioglycerol+Na$^+$ matrix) m/e: ([M+H]$^+$) 636.5679 (100%), calcd. 636.5669.

Example 8

This example includes a description of one or more exemplary synthetic procedures for obtaining Compounds 106 and 124.

Compound 124: Compound 47 (0.256 g, 0.489 mmol) was dissolved in CH$_2$Cl$_2$ (10 mL), and cooled to 0° C. followed by the addition of Na$_2$HPO$_4$ (0.69 g, 4.89 mmol) and urea-hydrogen peroxide complex (UHP) (0.069 g, 0.733 mmol). Trifluoroacetic anhydride (TFAA) (0.138 mL, 0.977 mmol) was then added dropwise. The suspension was stirred for 12 hr, and additional UHP (23 mg, 0.25 mmol) and TFAA (0.069 mL, 0.49 mmol) were added. After another 12 hr, H$_2$O (30 mL) was added, and the resulting mixture was extracted with EtOAc (3×20 mL). The combined extracts were washed with brine (50 mL), dried over anhydrous Na$_2$SO$_4$, and concentrated in vacuo. SiO$_2$ chromatography (EtOAc/hexanes 1:5) afforded the desired product (0.145 g, 55% yield) as a colorless oil. $^1$H NMR (CDCl$_3$, 300 MHz) δ 5.21 (dd, J=9.3 and 7.3 Hz, 1 H), 3.70-3.57 (m, 2 H), 3.55 (t, J=6.0 Hz, 2 H), 3.43-3.37 (m, 6 H), 3.32-3.25 (m, 3 H), 3.17-3.02 (m, 2 H), 2.28-2.05 (m, 4 H), 2.03 (s, 3 H), 1.86-1.19 (series of multiplets, 19 H), 0.97 (dd, J=14.5 and 3.3 Hz, 1 H), 0.90 (s, 3 H), 0.78 (s, 3 H); $^3$C NMR (CDCl$_3$, 75 MHz) δ 171.08, 79.71, 78.03, 75.72, 75.53, 65.41, 65.04, 64.53, 48.79, 48.70, 46.49, 41.92, 39.44, 37.81, 35.45, 35.22, 35.10, 29.73, 29.63, 28.89, 28.33, 27.50, 27.34, 23.39, 22.97, 22.92, 21.28, 12.72; HRFAB-MS (thioglycerol+Na$^+$ matrix) m/e: ([M−H]$^+$) 614.3798 (24.5%), calcd. 614.3778.

Compound 106: Compound 124 (0.145 g, 0.236 mmol) was dissolved in CH$_2$Cl$_2$ (2 mL) and MeOH (1 mL). 20% NaOH solution (0.2 mL) was added. The mixture was stirred for 12 hr, and anhydrous Na$_2$SO$_4$ was used to remove water. After concentration in vacuo, the residue was purified by silica gel chromatography (EtOAc/hexanes 1:3) to afford the desired product (0.124 g, 92% yield) as a colorless oil. $^1$H NMR (CDCl$_3$, 300 MHz) δ 4.29 (bs, 1 H), 3.69-3.60 (m, 2 H), 3.52 (t, J=6.0 Hz, 2 H), 3.45-3.32 (m, 8 H), 3.26 (d, J=2.7 Hz, 1 H), 3.17-3.02 (m, 2 H), 2.19-1.94 (m, 4 H), 1.90-1.62 (series of multiplets, 13 H), 1.57-1.20 (series of multiplets, 7 H), 0.97 (dd, J=14.3 and 3.1 Hz, 1 H), 0.90 (s, 3 H), 0.73 (s, 3 H); $^{13}$C NMR (CDCl$_3$, 75 MHz) δ 79.69, 78.03, 75.47, 73.38, 65.46, 65.00, 64.47, 48.87, 48.68, 46.83, 41.93, 39.71, 37.87, 35.43, 35.20, 35.09, 29.96, 29.69, 29.59, 29.53, 28.89, 28.44, 27.48, 23.72, 22.91, 22.71, 11.77. The alcohol (0.124 g, 0.216 mmol) was dissolved in dry THF (20 mL) followed by the addition of LiAlH$_4$ (33 mg, 0.866 mmol). The gray suspension was stirred under N$_2$ for 12 hr. Na$_2$SO$_4$.10 H$_2$O (about 2 g) was carefully added. After the gray color in the suspension dissipated, anhydrous Na$_2$SO$_4$ was added and the precipitate was removed by filtration. After the removal of solvent, the residue was purified by column chromatography (SiO$_2$, MeOH/CH$_2$Cl$_2$/28% NH$_3$.H$_2$O 2.5: 2.5:1). After concentration of the relevant fractions, 1 M HCl(2 mL) was added to dissolve the milky residue. The resulting clear solution was washed with Et$_2$O (2×10 mL). To the aqueous phase, 20% NaOH solution was added until the solution became strongly basic. CH$_2$Cl$_2$ (20 mL, 2×10 mL) was used to extract the basic solution. The combined extracts were dried over anhydrous Na$_2$SO$_4$ and removal of solvent gave the desired product (0.050 g, 47% yield) as a colorless oil. $^1$H NMR (20% CDCl$_3$ in CD$_3$OD, 300 MHz) δ 4.77 (s, 7 H), 4.25 (t, J=8.5 Hz, 1 H), 3.75-3.68 (m, 1 H), 3.66-3.58 (m, 1 H), 3.55 (t, J=6.1 Hz, 2 H), 3.48-3.41 (m, 1 H), 3.34 (bs, 1 H), 3.30 (d, J=3.6 Hz, 1 H), 3.17-3.08 (m, 2 H), 2.86-2.70 (m, 6 H), 2.20-1.91 (m, 4 H), 1.88-1.16 (series of multiplets, 19 H), 1.00 (dd, J=14.2 and 3.0 Hz, 1 H), 0.93 (s, 3 H), 0.73 (s, 3 H); $^{13}$C NMR (20% CDCl$_3$ in CD$_3$OD, 75 MHz) δ 80.62, 79.12, 76.74, 73.77, 68.50, 67.79, 67.17, 47.69, 43.04, 40.76, 40.64, 40.62, 40.22, 39.01, 36.32, 36.25, 35.94, 34.27, 33.97, 33.72, 30.13, 29.53, 28.43, 24.48, 23.58, 23.40, 12.38; HRFAB-MS (thioglycerol+Na$^+$ matrix) m/e ([M+H]$^+$) 496.4108 (100%), calcd. 496.4114.

Example 9

This example includes a description of one or more exemplary synthetic procedures for obtaining Compounds 109 and 126-129.

Compound 126: Compound 125 (2.30 g, 3.52 mmol) was dissolved in MeOH (50 mL) and CH$_2$Cl$_2$ (100 mL). A small amount of Et$_3$N was added, and the solution was cooled to −78° C. Ozone was bubbled through the solution until a blue color persisted. Me$_2$S (4 mL) was introduced followed by the addition of NaBH$_4$ (0.266 g, 0.703 mmol) in MeOH (10 mL). The resulting solution was allowed to warm and stir overnight. The solution was concentrated in vacuo, and brine (60 mL) was added. The mixture was extracted with EtOAc (40 ml, 2×30 mL), and the combined extracts were washed with brine and dried over anhydrous Na$_2$SO$_4$. Silica gel chromatography (EtOAc) afforded the product (1.24 g, 76% yield) as a white solid. m.p. 219-220 C.; $^1$H NMR (CDCl$_3$, 300 MHz) δ 5.10 (t, J=2.8 Hz, 1 H), 4.90 (d, J=2.7 Hz, 1 H), 3.73-3.59 (m, 2 H), 3.56-3.44 (m, 1 H), 2.13 (s, 3 H), 2.09 (s, 3 H), 2.07-0.95 (series of multiplets, 23 H), 0.91 (s, 3 H), 0.83 (d, J=6.3 Hz, 3 H), 0.74 (s, 3 H); $^{13}$C NMR (CDCl$_3$, 75 MHz) δ 170.84, 170.82, 75.63, 71.77, 71.03, 60.73, 48.10, 45.26, 43.54, 41.16, 38.78, 37.89, 35.00, 34.43, 32.26, 31.50, 30.60, 29.07, 27.50, 25.70, 22.96, 22.71, 21.81, 21.63, 18.18, 12.35; HRFAB-MS (thioglycerol+Na$^+$ matrix) m/e: ([M+H]$^+$) 465.3197 (20%), calcd. 465.3216.

Compound 127: Compound 126 (1.24 g, 2.67 mmol) was dissolved in MeOH (30 mL), and NaOH (0.54 g, 13.4 mmol) was added. The suspension was refluxed under N$_2$ for 24 hr. The MeOH was removed in vacuo followed by the addition of H$_2$O (50 mL). The precipitate was filtered, washed with H$_2$O and then dried in vacuo to give a white solid (1.02 g). This solid was dissolved in DMF (40 mL) followed by the sequential addition of NEt$_3$ (1.12 mL, 8.02 mmol), DMAP (16.3 mg, 0.13 mmol) and trityl chloride (1.49 g, 5.34 mmol). The suspension was stirred under N$_2$ for 12 hr and then heated up to 50° C. for 24 hr. H$_2$O (100 mL) was added to the cooled suspension, and the mixture was extracted with EtOAc (3×50 mL). The combined extracts were washed with brine (100 mL), dried over anhydrous $Na_2SO_4$, and concentrated in vacuo. Silica gel chromatography (EtOAc) afforded the product (1.20 g, 72% yield) as a pale yellow glass. To this glass was added dry THF (80 mL) and NaH (60% in mineral oil, 0.77 g, 19.3 mmol). The suspension was refluxed under $N_2$ for half an hour before the introduction of allylbromide (1.67 mL, 19.3 mmol). After 48 hr at reflux, another 10 eq. of NaH and allylbromide were introduced. After another 48 hr, the reaction mixture was cooled and $H_2O$ (100 mL) was slowly added. The resulting mixture was extracted with hexanes (3×50 mL), and the combined extracts were washed with brine (100 mL) and dried over anhydrous $Na_2SO_4$. Silica gel chromatography (5% EtOAc in hexanes) afforded the product (1.27 g, 64% yield for all three steps) as a clear glass. $^1H$ NMR ($CDCl_3$, 300 MHz) δ 7.46-7.43 (m, 6 H), 7.29-7.16 (m, 9 H), 5.98-5.81 (m, 3 H), 5.29-5.18 (m, 3 H), 5.14-5.03 (m, 3 H), 4.11-3.97 (m, 4 H), 3.75-3.67 (m, 2 H), 3.49 (bs, 1 H), 3.32-3.13 (d, J=2.4 Hz, 1 H), 3.20-3.13 (m, 2 H), 3.00 (m, 1 H), 2.33-2.12 (m, 3 H), 2.03-0.92 (series of multiplets, 19 H), 0.88 (s, 3 H), 0.78 (d, J=6.6 Hz, 3 H), 0.65 (s, 3 H); $^{13}C$ NMR ($CDCl_3$, 75 MHz) δ 144.71, 136.08, 136.04, 135.94, 128.80, 127.76, 126.86, 116.30, 115.57, 86.53, 80.77, 79.20, 74.96, 69.42, 69.34, 68.81, 62.00, 46.87, 46.48, 42.67, 42.11, 39.90, 36.15, 35.50, 35.14, 35.10, 33.23, 28.99, 28.09, 27.75, 27.56, 23.36, 23.32, 23.12, 18.24, 12.66; HRFAB-MS (thioglycerol+$Na^+$ matrix) m/e: ([M+Na]$^+$) 765.4875 (100%), calcd. 765.4859.

Compound 128: To a THF (40 mL) solution of 127 (1.27 g, 1.71 mmol) was added 9-BBN (0.5 M solution in THF, 17.1 mL). The mixture was stirred for 12 hr before the addition of NaOH (20% solution, 10 mL) and $H_2O$ (30% solution, 10 mL). The resulted mixture was refluxed for 1 hr followed by the addition of brine (100 mL) and extraction with EtOAc (4×30 mL). The combined extracts were dried over anhydrous $Na_2SO_4$ and concentrated in vacuo. Silica gel chromatography (5% MeOH in $CH_2Cl_2$) afforded the product (1.26 g, 93% yield) as a clear glass. $^1H$ NMR (5% $CD_3OD$ in $CDCl_3$, 300 MHz) δ 7.46-7.43 (m, 6 H), 7.32-7.20 (m, 9 H), 3.94 (s, 3 H), 3.78-3.56 (m, 10 H), 3.48 (bs, 1 H), 3.32-3.26 (m, 2 H), 3.24-3.12 (m, 3 H), 3.00 (dd, J=8.2 and 6.1 Hz, 1 H), 2.23-1.96 (m, 3 H), 1.90-0.95 (series of multiplets, 25 H), 0.90 (s, 3 H), 0.77 (d, J=6.6 Hz, 3 H), 0.66 (s, 3 H); $^{13}C$ NMR (5% $CD_3OD$ in $CDCl_3$, 75 MHz) δ 144.52, 128.64, 127.64, 126.76, 86.43, 80.55, 79.31, 77.65, 77.23, 76.80, 76.06, 66.17, 66.01, 65.41, 61.93, 61.20, 60.73, 60.39, 47.29, 46.08, 42.65, 41.62, 39.49, 36.02, 35.10, 34.89, 34.77, 32.89, 32.71, 32.41, 32.26, 28.68, 27.70, 27.51, 27.19, 23.26, 22.66, 22.50, 18.23, 12.34; HRFAB-MS (thioglycerol+$Na^+$ matrix) m/e: ([M+Na]$^+$) 819.5169 (100%), calcd. 819.5099.

Compound 129: To a $CH_2Cl_2$ (50 mL) solution of compound 128 (1.26 g, 1.58 mmol) at 0° C. was added $Et_3N$ (0.92 mL, 6.60 mmol) followed by mesyl chloride (0.47 mL, 6.05 mmol). After 15 minutes, $H_2O$ (10 mL) was followed by brine (80 mL). The mixture was extracted with EtOAc (60 mL, 2×30 mL) and the combined extracts were dried over anhydrous $Na_2SO_4$. After removal of solvent in vacuo, the residue was dissolved in DMSO (10 mL) and $NaN_3$ (1.192 g, 18.3 mmol) was added. The suspension was heated to 60° C. under $N_2$ overnight. $H_2O$ (100 mL) was added, and the mixture was extracted with EtOAc (3×40 mL). The combined extracts were washed with brine and dried over anhydrous $Na_2SO_4$. Removal of the solvent in vacuo afforded a pale yellow oil. The oil was dissolved in MeOH (10 mL) and $CH_2Cl_2$ (20 mL) and TsOH (17.4 mg, 0.092 mmol) was added. After 12 hr, saturated aqueous $NaHCO_3$ (20 mL) and brine (50 mL) were added and the mixture was extracted with EtOAc (3×40 mL). The combined extracts were washed with brine (50 mL) and dried over anhydrous $Na_2SO_4$. Silica gel chromatography (EtOAc/hexanes 1:3) afforded the desired product (0.934, 94%) as a pale yellow oil. $^1H$ NMR ($CDCl_3$, 500 MHz) δ 3.75-3.70 (m, 1 H), 3.68-3.63 (m, 2 H), 3.62-3.57 (m, 1 H), 3.53 (t, J=6.1 Hz, 2 H), 3.50 (bs, 1 H), 3.46-3.38 (m, 6 H), 3.26 (d, J=2.4 Hz, 1 H), 3.24-3.20 (m, 1 H), 3.16-3.12 (m, 1 H), 3.10-3.04 (m, 1 H), 2.17-2.04 (m, 3 H), 1.96-1.63 (m, 14 H), 1.53-1.45 (m, 3 H), 1.35-1.20 (m, 7 H), 1.08-1.00 (m, 1 H), 0.97-0.88 (m, 1 H), 0.94 (d, J=6.8 Hz, 3 H), 0.89 (s, 3 H), 0.67 (s, 3 H); $^{13}C$ NMR ($CDCl_3$, 75 MHz) δ 80.64, 79.81, 76.06, 65.05, 64.49, 64.34, 61.03, 49.02, 48.98, 48.78, 46.93, 46.53, 42.76, 42.01, 39.83, 39.14, 35.46, 35.33, 35.12, 32.97, 29.79, 29.73, 29.10, 27.90, 27.68, 23.56, 23.06, 22.88, 18.24, 12.60; HRFAB-MS (thioglycerol+$Na^+$ matrix) m/e: ([M+Na]$^+$) 652.4285 (100%), calcd. 652.4295.

Compound 109: Compound 129 (0.245 g, 0.391 mmol) was dissolved in THF (30 mL) followed by the addition of $LiAlH_4$ (59 mg, 1.56 mmol). The gray suspension was stirred under $N_2$ 12 hr. $Na_2SO_4 \cdot 10H_2O$ powder (about 1 g) was carefully added. After the gray color in the suspension dissipated, anhydrous $Na_2SO_4$ was added and the precipitate was removed by filtration. After the removal of solvent, the residue was purified by silica gel chromatography ($CH_2Cl_2$/MeOH/28% $NH_3 \cdot H_2O$ 10: 5:1 then 10:5:1.5). The solvent was removed from relevant fractions, and 1 M HCl (4 mL) was added to dissolve the residue. The resulting clear solution was extracted with $Et_2O$ (3×10 mL). 20% NaOH solution was added until the solution became strongly basic. $CH_2Cl_2$ (4×10 mL) was used to extract the basic solution. The combined extracts were dried over anhydrous $Na_2SO_4$, and removal of solvent in vacuo gave the desired product (0.15 g, 71% yield) as a colorless oil. $^1H$ NMR (about 20% $CD_3OD$ in $CDCl_3$, 500 MHz) δ 4.73 (bs, 7 H), 3.74-3.70 (m, 1 H), 3.65-3.60 (m, 2 H), 3.56-3.52 (m, 4 H), 3.31-3.28 (m, 2 H), 3.16-3.09 (m, 2 H), 2.82-2.71 (m, 6 H), 2.19-2.06 (m, 3 H), 1.97-1.66 (series of multiplets, 15 H), 1.58-1.48 (m, 3 H), 1.38-0.98 (m, 7 H), 0.96 (d, J=6.8 Hz, 3 H), 0.93 (s, 3 H), 0.71 (s, 3 H), $^{13}C$ NMR (about 20% $CD_3OD$ in $CDCl_3$, 75 MHz) δ 81.80, 80.60, 77.17, 67.88, 67.86, 67.18, 60.73, 48.11, 47.28, 43.93, 42.99, 41.34, 40.76, 40.72, 40.24, 39.70, 36.33, 36.18, 35.86, 34.29, 33.99, 33.96, 33.83, 29.60, 29.00, 28.57, 28.54, 24.33, 23.59, 23.48, 18.86, 13.04; HRFAB-MS (thioglycerol+$Na^+$ matrix) m/e: ([M+H]$^+$) 552.4756 (100%), calcd. 552.4772.

Example 10

This example includes a description of one or more exemplary synthetic procedures for obtaining Compounds 108 and 130.

Compound 130: o-$NO_2C_6H_4SeCN$ (0.094 g, 0.21 mmol) and $Bu_3P$ (0.095 mL, 0.38 mmol) were stirred in dry THF (5 mL) at 0° C. for ½ hr followed by the addition of compound 129 (0.10 g, 0.159 mmol) in THF (2 mL). The suspension was stirred for 1 hr followed by the addition of $H_2O_2$ (30% aqueous solution, 2 mL). The mixture was stirred for 12 hr followed by extraction with hexanes (4×10 mL). The combined extracts were dried over anhydrous $Na_2SO_4$. The desired product (0.035 g, 36% yield) was obtained as pale yellowish oil after silical gel chromatography (10% EtOAc/hexanes). $^1H$ NMR ($CDCl_3$, 500 MHz) δ 5.73-5.66 (ddd, J=17.1, 10.2, 8.3 Hz, 1 H), 4.90 (dd, J=17.1, 2.0 Hz, 1 H), 4.82 (dd, J=10.2 Hz, 1.96 Hz, 1 H), 3.68-3.64 (m, 1 H), 3.62-3.58 (m, 1 H), 3.54-3.26 (m, 9 H), 3.25-3.22 (m, 2 H), 3.15-3.11 (m, 1 H), 3.10-3.04 (m, 1 H), 2.17-1.62 (series of multiplets, 18 H), 1.51-1.43 (m, 2 H), 1.35-1.18 (m, 4 H), 1.06-0.91 (m, 2 H), 1.02 (d, J=6.3 Hz, 3 H), 0.90 (s, 3 H), 0.68 (s, 3 H); $^{13}C$ NMR (CDCl$_3$, 75 MHz) δ 145.50, 111.72, 80.60, 79.82, 76.09, 65.06, 64.50, 64.45, 49.05, 48.97, 48.79, 46.43, 46.13, 42.76, 42.03, 41.30, 39.84, 35.49, 35.34, 35.15, 29.82, 29.80, 29.75, 29.11, 28.00, 27.84, 27.68, 23.56, 23.08, 22.95, 19.79, 12.87; HRFAB-MS (thioglycerol+Na$^+$ matrix) m/e: ([M+Na]$^+$) 634.4167 (90.6%), calcd. 634.4169.

Compound 108: Compound 130 (0.105 g, 0.172 mmol) was dissolved in CH$_2$Cl$_2$ (5 mL) and MeOH (5 mL) at −78° C. O$_3$ was bubbled into the solution for ca. 20 min. Me$_2$S (1 mL) was added followed, and the solvent was removed in vacuo. The residue was dissolved in THF (15 mL), and LiAlH$_4$ (0.033 g, 0.86 mmol) was added. The suspension was stirred for 12 hr. Na$_2$SO$_4$.10H$_2$O (about 2 g) was carefully added. After the gray color of the suspension dissipated, anhydrous Na$_2$SO$_4$ was added and the precipitate was removed by filtration. Concentration and silica gel chromatography (CH$_2$Cl$_2$/MeOH/28% NH$_3$.H$_2$O 10: 5:1.5 then 9:6:1.8) yielded a white glass. To this material was added 1 M HCl (4 mL). The resulting clear solution was washed with Et$_2$O (3×10 mL). 20% NaOH solution was added to the aqueous phase until the solution became strongly basic. CH$_2$Cl$_2$ (4×10 mL) was used to extract the basic solution. The combined extracts were dried over anhydrous Na$_2$SO$_4$ and removal of solvent gave the desired product (0.063 g, 68% yield) as a colorless oil. $^1$H NMR (about 10% CD$_3$OD in CDCl$_3$, 500 MHz) δ 4.76 (bs, 7 H), 3.75-3.71 (m, 1 H), 3.66-3.62 (m, 1 H), 3.58-3.52 (m, 4 H), 3.33-3.29 (m, 2 H), 3.22 (dd, J=10.5 and 7.6 Hz, 1 H), 3.15-3.09 (m, 2 H), 2.81 (t, J=6.8 Hz, 2 H), 2.76-2.71 (m, 4 H), 2.19-2.08 (m, 3 H), 2.00-1.66 (series of multiplets, 14 H), 1.58-1.45 (m, 3 H), 1.40-1.08 (m, 5 H), 1.03 (d, J=6.8 Hz, 3 H), 1.02-0.96 (m, 1 H), 0.93 (s, 3 H), 0.72 (s, 3 H); $^{13}$C NMR (about 10% CD$_3$OD in CDCl$_3$, 75 MHz) δ 81.74, 80.64, 77.23, 67.95, 67.87, 67.18, 47.32, 44.59, 43.72, 43.01, 41.26, 40.80, 40.71, 40.23, 40.02, 36.36, 36.20, 35.87, 34.27, 33.99, 33.90, 29.60, 29.05, 28.58, 28.08, 24.49, 23.62, 23.46, 16.84, 13.12; HRFAB-MS (thioglycerol+Na$^+$ matrix) m/e: ([M+H]$^+$) 538.4578 (4.7%), calcd. 538.4584.

Example 11

This example includes a description of one or more exemplary synthetic procedures for obtaining Compounds CSA-21, 133-134 and CSA-15.

Compound CSA-21: Compound 115 (0.118 g, 0.183 mmol) was dissolved in dry CH$_2$Cl$_2$ (10 mL), and SO$_3$ pyridine complex (0.035 g, 0.22 mmol) was added. The suspension was stirred for 12 hr. The solvent was removed in vacuo to give white powder. To the white powder was added 1 M HCl (10 mL) and the resulting mixture was extracted with CH$_2$Cl$_2$ (4×10 mL). The combined extracts were dried over anhydrous Na$_2$SO$_4$. The desired product (0.11 g, 84%) was obtained as a pale yellow oil after silica gel chromatography (10% MeOH in CH$_2$Cl$_2$). $^1$H NMR (about 10% CD$_3$OD in CDCl$_3$, 500 MHz) δ 4.03 (t, J=6.8 Hz, 2 H), 3.69-3.65 (m, 1 H), 3.62-3.58 (m, 1 H), 3.55 (t, J=6.1 Hz, 2 H), 3.51 (bs, 1 H), 3.46-3.38 (m, 6 H), 3.27 (d, J=2.4 Hz, 1 H), 3.26-3.21 (m, 1 H), 3.18-3.07 (m, 2 H), 2.18-2.03 (m, 3 H), 1.95-1.47 (series of multiplets, 19 H), 1.40-0.96 (series of multiplets, 9 H), 0.92 (d, J=6.8 Hz, 3 H), 0.91 (s, 3 H), 0.66 (s, 3 H); $^{13}$C NMR (about 10% CD$_3$OD in CDCl$_3$, 75 MHz) δ 80.43, 79.68, 75.87, 69.30, 64.82, 64.32, 64.14, 48.78, 48.73, 48.50, 46.44, 46.21, 42.49, 41.76, 39.61, 35.36, 35.17, 35.06, 34.85, 31.73, 29.53, 29.46, 29.44, 28.84, 27.68, 27.48, 27.38, 25.91, 23.30, 22.75, 22.66, 17.70, 12.32; HRFAB-MS (thioglycerol+Na$^+$ matrix) m/e: ([M−H+2Na]$^+$) 768.3831 (100%), calcd. 768.3843. The azides were reduced by treating the triazide (0.11 g, 0.15 mmol) with Ph$_3$P (0.20 g, 0.77 mmol) in THF (10 mL) and H$_2$O (1 mL). The mixture was stirred for 3 days. The solvent was removed in vacuo, and the residue was purified by silica gel chromatography (CH$_2$Cl$_2$/MeOH/28% NH$_3$.H$_2$O 12:6:1 then 10: 5:1.5) to afford the desired product (0.077 g, 78% yield) as a glass. HCl in Et$_2$O (1 M, 0.5 mL) was added to the glass to give the corresponding HCl salt. $^1$H NMR (about 10% CDCl3 in CD$_3$OD, 500 MHz) δ 4.81 (s, 10 H), 4.07-3.97 (m, 2 H), 3.82 (bs, 1 H), 3.71 (bs, 1 H), 3.65 (t, J=5.2 Hz, 2 H), 3.57 (bs, 1 H), 3.37-3.30 (m, 2 H), 3.22-3.02 (m, 8 H), 2.12-1.71 (series of multiplets, 17 H), 1.65-1.01 (series of multiplets, 13 H), 0.97 (d, J=6.8 Hz, 3 H), 0.94 (s, 3 H), 0.73 (s, 3 H); $^{13}$C NMR (about 10% CDCl$_3$ in CD$_3$OD, 75 MHz) δ 81.89, 80.58, 77.50, 70.04, 66.71, 66.56, 66.02, 47.11, 46.76, 44.20, 42.66, 40.50, 39.60, 39.40, 36.24, 36.11, 35.89, 35.67, 32.28, 29.38, 29.23, 29.10, 28.94, 28.49, 26.06, 24.21, 23.46, 23.30, 18.50, 12.86; HRFAB-MS (thioglycerol+Na$^+$ matrix) m/e: ([M+Na]$^+$) 668.4271 (100%), calcd. 668.4258.

Compound CSA-13: The mesylate derived from 23 (0.19 g, 0.264 mmol) was stirred with excess octyl amine (2 mL) at 80° C. for 12 hr. After removal of octylamine in vacuo, the residue was chromatographed (silica gel, EtOAc/hexanes 1:4 with 2% Et$_3$ N) to afford the desired product (0.19 g, 95% yield) as a pale yellow oil. $^1$H NMR (CDCl$_3$, 300 MHz) δ 3.69-3.37 (series of multiplets, 11 H), 3.26-3.00 (m, 4 H), 2.61-2.53 (m, 4H), 2.20-2.02 (m, 3 H), 1.98-0.99 (series of multiplets, 40 H), 0.92-0.85 (m, 9 H), 0.65 (s, 3H); $^{13}$C NMR (CDCl$_3$, 75 MHz) δ 80.60, 79.74, 76.05, 64.97, 64.40, 64.28, 50.79, 50.25, 49.00, 48.90, 48.71, 46.47, 46.34, 42.65, 41.96, 39.80, 35.77, 35.41, 35.27, 35.05, 33.73, 31.96, 30.25, 29.76, 29.74, 29.67, 29.39, 29.05, 27.84, 27.61, 27.55, 26.70, 23.50, 23.00, 22.82, 22.79, 18.06, 14.23, 12.54; HRFAB-MS (thioglycerol+Na$^+$ matrix) m/e: ([M+H]$^+$) 755.6012 (100%), calcd. 755.6024. The triazide (0.18 g, 0.239 mmol) was dissolved in THF (10 mL) and EtOH (10 mL). Lindlar catalyst (44 mg) was added, and the suspension was shaken under H$_2$ (50 psi) for 12 hr. After removal of the solvent in vacuo, the residue was purified by silica gel chromatography (CH$_2$Cl$_2$/MeOH/28% NH$_3$.H$_2$O 10:5:1, then 10:5:1.5). To the product, 1 M HCl (2 mL) and the resulting clear solution was extracted with Et$_2$O (2×10 mL). 20% NaOH solution was added until the solution became strongly basic. CH$_2$Cl$_2$ (20 mL, 2×10 mL) was used to extract the basic solution. The combined extracts were dried over anhydrous Na$_2$SO$_4$, and removal of solvent in vacuo gave the desired product (0.114 g, 68% yield) as a clear oil. $^1$H NMR (about 20% CDCl$_3$ in CD$_3$OD, 500 MHz) δ 4.79 (bs, 7 H), 3.74-3.70 (m, 1 H), 3.61 (m, 1 H), 3.56-3.51 (m, 3 H), 3.31-3.29 (m, 2 H), 3.16-3.09 (m, 2 H), 2.88-2.72 (m, 6 H), 2.59-2.51 (m, 4 H), 2.18-2.07 (m, 3 H), 1.97-1.66 (series of multiplets, 14 H), 1.62-0.97 (series of multiplets, 25 H), 0.95 (d, J=6.3 Hz, 3 H), 0.93 (s, 3 H), 0.89 (t, J=6.8 Hz, 3 H), 0.70 (s, 3 H); $^{13}$C NMR (about 20% CDCl$_3$ in CD$_3$OD, 75 MHz) δ 81.82, 80.63, 77.23, 67.85, 67.19, 51.20, 50.69, 47.82, 47.24, 43.92, 43.01, 41.30, 40.80, 40.68, 40.22, 36.74, 36.38, 36.20, 35.87, 34.66, 34.15, 33.87, 32.90, 30.54, 30.39, 30.30, 29.64, 29.03, 28.59, 28.41, 26.96, 24.37, 23.65, 23.48, 18.75, 14.63, 13.09; HRFAB-MS (thioglycerol+Na$^+$ matrix) m/e: ([M+H]$^+$) 677.6309 (46.6%), calcd. 677.6309.

Compound CSA-46: Compound CSA-46 was prepared using the methods of CSA-13, substituting 7-deoxycholic steroid backbone precursor in place of cholic acid.

Compound 134: Compound CSA-13 (0.08 g, 0.12 mmol) was dissolved in CHCl$_3$ (5 mL) and MeOH (5 mL), aminoiminosulfonic acid (0.045 g, 0.36 mmol) was added, and the suspension was stirred for 12 hr. The solvent was removed in vacuo, and the residue was dissolved in 1 M HCl (6 mL) and H$_2$O (10 mL). The solution was washed with Et$_2$O (3×5 mL), and 20% NaOH solution was then added dropwise until the solution became strongly basic. The basic mixture was extracted with CH$_2$CT$_2$ (4×5 mL). The combined extracts were dried over anhydrous Na$_2$SO$_4$ and concentrated in vacuo to give the desired product (0.087 g, 91% yield) as a white glass. $^1$H NMR (about 20% CDCl$_3$ in CD$_3$OD, 500 MHz) δ 4.96 (bs, 13 H), 3.74-3.68 (m, 1 H), 3.65-3.50 (m, 4 H), 3.38-3.18 (series of multiplets, 10 H), 2.60-2.50 (m, 4 H), 2.15-1.99 (m, 3 H), 1.88-1.72 (m, 14 H), 1.60-0.99 (series of multiplets, 25 H), 0.94 (bs, 6 H), 0.89 (t, J=6.6 Hz, 3 H), 0.71 (s, 3 H); $^{13}$C NMR (about 20% CDCl$_3$ in CD$_3$OD, 75 MHz) δ 159.00, 158.87, 158.72, 81.68, 79.93, 76.95, 66.59, 65.93, 65.45, 50.82, 50.40, 47.64, 46.94, 43.67, 42.27, 40.18, 39.25, 36.19, 35.66, 35.40, 34.21, 32.45, 30.51, 30.26, 30.18, 30.10, 29.86, 29.35, 28.71, 28.15, 28.00, 26.87, 23.94, 23.44, 23.23, 23.12, 18.61, 14.42, 12.98; HRFAB-MS (thioglycerol+Na$^+$ matrix) m/e: ([M+H]$^+$) 803.6958 (18.4%), calcd. 803.6953.

Compound CSA-15: The mesylate derived from 23 (0.092 g, 0.128 mmol) was dissolved in DMSO (2 mL) followed by the addition of NaN$_3$ (0.0167 g, 0.256 mmol). The suspension was heated to 70° C. for 12 hr. H$_2$O (20 mL) was added to the cooled suspension, and the mixture was extracted with EtOAc/hexanes (1:1) (20 mL, 3×10 mL). The combined extracts were washed with brine (30 mL), dried over anhydrous Na$_2$SO$_4$, and concentrated in vacuo to give the product (0.081 g, 95% yield) as a pale yellow oil. $^1$H NMR (CDCl$_3$, 300 MHz) δ 3.69-3.36 (m, 11 H), 3.25-3.02 (m, 6 H), 2.20-2.02 (m, 3 H), 1.97-1.60 (m, 15 H), 1.55-0.98 (m, 13 H), 0.92 (d, J=6.3 Hz. 3 H), 0.89 (s, 3 H), 0.66 (s, 3 H); $^{13}$C NMR (CDCl$_3$, 75 MHz) δ 80.59, 79.77, 76.03, 65.01, 64.46, 64.30, 52.12, 48.99, 48.95, 48.76, 46.44, 46.42, 42.70, 41.99, 39.82, 35.56, 35.44, 35.31, 35.09, 33.09, 29.79, 29.77, 29.71, 29.08, 27.88, 27.78, 27.66, 25.65, 23.53, 23.03, 22.85, 18.00, 12.58; HRFAB-MS (thioglycerol+Na$^+$ matrix) m/e: ([M+Na]$^+$) 691.4512 (100%), calcd. 691.4496. The tetraazide (0.081 g, 0.12 mmol) was dissolved in THF (5 mL) and EtOH (10 mL). Lindlar catalyst (30 mg) was added, and the suspension was shaken under H$_2$ (50 psi) for 12 hr. After removal of the solvent in vacuo, the residue was purified by silica gel chromatography (CH$_2$Cl$_2$/MeOH/28% NH$_3$.H$_2$O 5:3:1, then 2:2:1). To the product, 1M HCl (2 mL) was added, and the resulting solution was washed with Et$_2$O (2×10 mL). 20% NaOH solution was added to the aqueous phase until the solution became strongly basic. CH$_2$Cl$_2$ (10 mL, 2×5 mL) was used to extract the basic solution. The combined extracts were dried over anhydrous Na$_2$SO$_4$, and concentration in vacuo gave the desired product (0.044 g, 64% yield) as a colorless oil. $^1$H NMR (about 20% CDCl$_3$ in CD$_3$OD, 500 MHz) δ 4.79 (bs, 8 H), 3.74-3.70 (m, 1 H), 3.66-3.62 (m, 1 H), 3.56-3.52 (m, 3 H), 3.31-3.27 (m, 2 H), 3.16-3.10 (m, 2 H), 2.82-2.70 (m, 6 H), 2.64-2.54 (m, 2 H), 2.19-2.07 (m, 3 H), 1.99-1.66 (series of multiplets, 14 H), 1.58-0.96 (series of multiplets, 13 H), 0.96 (d, J=6.6 Hz, 3 H), 0.93 (s, 3 H), 0.70 (s, 3 H); $^{13}$C NMR (about 20% CDCl$_3$ in CD$_3$OD, 75 MHz) δ 81.96, 90.76, 77.33, 67.92, 67.26, 47.84, 47.33, 44.04, 43.24, 43.15, 41.40, 40.91, 40.78, 40.29, 36.82, 36.48, 36.28, 35.96, 34.39, 34.11, 30.59, 29.69, 29.13, 28.68, 28.64, 24.43, 23.69, 23.48, 18.77, 13.06; HRFAB-MS (thioglycerol+Na$^+$ matrix) m/e: ([M+H]$^+$) 565.5041 (100%), calcd. 565.5057.

Example 12

This example includes a description of one or more exemplary synthetic procedures for obtaining Compounds 203a-b, 207a-c, 209a-c, 210a-b and CSA-31.

Compounds 203a-b, 207a-c, 208a-c, 209a-c, and 210a-b: BOC-glycine was reacted with DCC, DMAP and cholic acid derivative 201 (Scheme 11) to give triester 202a in good yield. A similar reaction incorporating BOC-β-alanine was also successful, giving 202b. Deprotection of 202a and 202b with HCl in dioxane, followed by purification (SiO$_2$ chromatography with a CH$_2$Cl$_2$ MeOH/NH$_4$OH eluent), gave triesters 203a and 203b in good yield.

Triamides of glycine and β-alanine (207a and 207b, respectively) were formed using the same reaction conditions (Scheme 12). Triamides with a-branched amino acids could also be formed. For example, under the conditions described, a triamide with bis-BOC-lysine side chains was formed (compound 207c). The C24 esters of 207a-c were hydrolyzed with LiOH in THF and methanol to give alcohols 208a-c. Deprotection using HCl in dioxane (208a-c) gave triamides 209a-c in good yield. In addition, alcohols 208a and 208b were mesylated and reacted with benzylmethyl amine. Deprotection of the resulting compounds with HCl in dioxane gave triamides 210a and 210b (Scheme 12). Compound CSA-31 was prepared by analogy to compounds 210a and 210b.

Example 13

This example includes a description of one or more exemplary synthetic procedures for obtaining Compounds 302, 312-321, 324-326, 328-331 and 341-343.

Compound 302: Compound 308 (5β-cholanic acid 3,7,12-trione methyl ester) was prepared from methyl cholate and pyridinium dichromate in near quantitative yield from methyl cholate. Compound 308 can also be prepared as described in Pearson et al., J. Chem. Soc. Perkins Trans. 1 1985, 267; Mitra et al., J. Org. Chem. 1968, 33, 175; and Takeda et al., J. Biochem. (Tokyo) 1959, 46, 1313. Compound 308 was treated with hydroxyl amine hydrochloride and sodium acetate in refluxing ethanol for 12 hr (as described in Hsieh et al., Bioorg. Med. Chem. 1995, 3, 823), giving 309 in 97% yield.

A 250 ml three neck flask was charged with glyme (100 ml); to this was added 309 (1.00 g, 2.16 mmol) and sodium borohydride (2.11 g, 55.7 mmol). TiCl$_4$ (4.0 mL, 36.4 mmol) was added to the mixture slowly under nitrogen at 0° C. The resulting green mixture was stirred at room temperature for 24 hours and then refluxed for another 12 h. The flask was cooled in an ice bath, and ammonium hydroxide (100 mL) was added. The resulting mixture was stirred for 6 hours at room temperature. Conc. HCl (60 mL) was added slowly, and the acidic mixture was stirred for 8 hours. The resulting suspension was made alkaline by adding solid KOH. The suspension was filtered and the solids were washed with MeOH. The combined filtrate and washings were combined and concentrated in vacuo. The resulting solid was suspended in 6% aqueous KOH (100 mL) and extracted with CH$_2$Cl$_2$ (4×75 mL). The combined extracts were dried over Na$_2$SO$_4$ and solvent was removed in vacuo to give 1.14 g of a white solid. The mixture was chromatographed on silica gel (CH$_2$Cl$_2$/MeOH/NH$_4$OH 12:6:1) giving 302 (0.282 g, 33% yield), 3 (0.066 g, 8% yield), 4 (0.118 g, 14% yield).

Compound 302: m.p. 200-202° C.; $^1$H NMR (about 10% CDCl$_3$ in CD$_3$OD, 300 MHz) δ 4.81 (bs, 7 H), 3.57-3.49 (m, 2 H), 3.14 (t, J=3.2 Hz, 1 H), 2.97 (bs, 1 H), 2.55-2.50 (m, 1 H), 2.15-2.10 (m, 1 H), 1.95-1.83 (m, 3 H), 1.74-0.99 (series of multiplets, 20 H), 1.01 (d, J=6.4 Hz, 3 H), 0.95 (s, 3 H), 0.79 (s, 3 H); $^{13}$C NMR (10% CDCl$_3$ in CD$_3$OD, 75 MHz) δ 63.28, 55.01, 52.39, 49.20, 48.69, 47.00, 43.24, 42.77, 41.03, 40.27, 36.82, 36.35, 35.75, 35.12, 32.77, 31.36, 30.10, 28.54, 27.88, 26.96, 24.35, 23.38, 18.18, 14.23, HRFAB-MS (thioglycerol+Na$^+$ matrix) m/e; ([M+H]$^+$) 392.3627 (100%); calcd. 392.3641.

Octanyl cholate (328): Cholic acid (3.14 g, 7.43 mmol) and 10-camphorsulfonic acid (0.52 g, 2.23 mmol) were dissolved in octanol (3.5 mL, 23.44 mmol). The solution was warmed to 40-50° C. in oil bath under vacuum (about 13 mm/Hg). After 14 h, the remaining octanol was evaporated under high vacuum. The crude product was purified via chromatography (silica gel, 5% MeOH in CH$_2$Cl$_2$) to afford the desired product (2.81 g, 73% yield) as a white powder. $^1$H NMR (CDCl$_3$, 500 MHz) δ 4.06 (t, J=6.7 Hz, 2 H), 3.98 (s, 1 H), 3.86 (s, 1 H), 3.48-3.44 (m, 1 H), 2.41-2.34 (m, 1 H), 2.28-2.18 (m, 3 H), 1.98-1.28 (series of multiplets, 35 H), 0.99 (d, J=3.3 Hz, 3 H), 0.90 (s, 3 H), 0.89 (t, J=7 Hz, 3 H), 0.69 (s, 3 H); $^{13}$C NMR (CDCl$_3$, 75 MHz) δ 154.38, 73.18, 72.14, 68.63, 56.07, 50.02, 49.32, 47.07, 46.74, 41.96, 41.67, 39.84, 39.76, 35.66, 35.45, 34.95, 34.86, 34.15, 32.97, 32.91, 31.65, 31.11, 30.68, 28.39, 27.78, 26.66, 26.52, 25.82, 25.70, 25.54, 25.15, 24.95, 23.45, 22.69, 17.77, 12.71; HRFAB-MS (thioglycerol+Na$^+$ matrix) m/e: ([M+Na]$^+$) 543.4015 (100%), calcd. 543.4026.

Representative synthesis of compounds 329-331: Octanyl cholate (328) (0.266 g, 0.511 mmol), N-t-Boc-glycine (0.403 g, 2.298 mmol), DCC (0.474 g, 2.298 mmol) and DMAP (0.0624 g, 0.051 mmol) were mixed in CH$_2$Cl$_2$ (15 mL) for 3 h. The resulting white precipitate was removed by filtration. The filtrate was concentrated, and the product was purified by chromatography (silica gel, EtOAc/Hexane 1:2) to afford the desired product (0.481 g, 95% yield) as a white powder. Compound 329 $^1$H NMR (CDCl$_3$, 300 MHz) δ 5.18 (br, 3 H), 5.01 (s, 1 H), 4.61 (m, 1 H), 4.04 (t, J=6.5 Hz, 2 H), 3.97-3.88 (series of multiplets, 6 H), 2.39-2.15 (series of multiplets, 2 H), 2.06-1.02 (series of multiplets, 35 H), 1.46 (s, 18 H), 1.45 (s, 9 H), 0.93 (s, 3 H), 0.88 (t, J=6.7 Hz, 3 H), 0.81 (d, J=6 Hz, 3 H), 0.74 (s, 3 H); $^{13}$C NMR (CDCl$_3$, 75 MHz) δ 174.26, 170.19, 169.9, 169.78, 155.87, 155.67, 79.95, 76.47, 75.167, 72.11, 64.55, 47.40, 45.28, 43.17, 42.86, 40.82, 37.94, 34.71, 34.63, 34.43, 31.86, 31.340, 31.20, 30.76, 29.29, 29.25, 28.80, 28.72, 28.42, 28.06, 27.96, 27.19, 26.81, 26.29, 26.012, 25.66, 22.87, 22.71, 22.57, 17.55, 14.18, 12.27; HRFAB-MS (thioglycerol+Na$^+$ matrix) m/e: ([M+Na]$^+$) 1014.6261 (100%), calcd. 1014.6242. Compound 330: $^1$H NMR (CDCl$_3$, 500 MHz) δ 5.10 (s, 1 H), 4.92 (d, J=2.44 Hz, 1 H), 4.55 (m, 1 H), 4.00 (t, J=6.8 Hz, 2 H), 3.39-3.33 (series of multiplets, 6 H), 2.595-2.467 (series of multiplets, 6 H), 2.31-2.12 (series of multiplets, 2 H), 2.01-1.00 (series of multiplets, 37 H), 1.39 (s, 27 H), 0.88 (s, 3 H), 0.84 (t, J=6.8 Hz, 3 H), 0.76 (d, J=6.3 Hz, 3 H), 0.69 (s, 3 H); $^{13}$C NMR (CDCl$_3$, 75 MHz) δ 174.16, 172.10, 171.78, 171.67, 155.95, 79.45, 75.67, 74.21, 71.10, 64.63, 47.79, 45.27, 43.52, 40.97, 37.92, 36.35, 35.14, 35.05, 34.90, 34.71, 34.46, 31.91, 31.45, 30.95, 29.35, 29.31, 28.96, 28.78, 28.56, 28.55, 27.22, 26.98, 26.269, 25.71, 23.00, 22.77, 22.64, 17.75, 14.24, 12.39; HRFAB-MS (thioglycerol+Na$^+$ matrix) m/e: ([M+Na]$^+$) 1056.6702 (100%), calcd. 1056.6712. Compound 331 $^{13}$C NMR (CDCl$_3$, 125 MHz) δ 174.00, 172.75, 172.41, 172.30, 156.03, 79.00, 75.28, 73.79, 70.77, 64.39, 47.43, 45.04, 43.21, 40.76, 40.00, 39.93, 37.78, 34.74, 34.62, 34.23, 32.19, 32.01, 31.70, 31.24, 30.77, 29.13, 29.10, 28.67, 38.58, 28.38, 25.86, 25.37, 22.56, 23.28, 17.51, 14.05, 12.13; HRFAB-MS (thioglycerol+Na$^+$ matrix) m/e: ([M+Na]$^+$) 1098.7181 (100%), calcd. 1098.7181.

Representative synthesis of compounds 341-343: To compound 329 (0.463 g, 0.467 mmol) was added HCl in dioxane (0.3 mL, 4.0 M). After stirring the mixture for 30 min, the excess HCl and solvent were removed in vacuo. The product was isolated, after chromatography (silica gel, CH$_2$Cl$_2$/MeOH/NH$_3$.H$_2$O 10:1.2:0.1) as a (0.271 g, 84%) pale oil. The trihydrochloride salt of 341 was prepared by addition of HCl in dioxane and evaporation of excess HCl and dioxane in vacuo giving a white powder. Compound 341: $^1$H NMR (CDCl$_3$ with about 10% CD$_3$OD, 500 MHz) δ 5.16 (s, 1 H), 4.99 (t, J=3.6 Hz, 1 H), 4.61 (m, 1 H), 4.04 (t, J=6.8 Hz, 2 H), 3.51-3.36 (m, 6 H), 2.34-2.15 (m, 2 H), 2.00-1.05 (series of multiplets, 40 H), 0.93 (s, 3 H), 0.88 (t, J=7.1 Hz, 3 H), 0.80 (d, J=3.2 Hz, 3 H), 0.74 (s, 3 H); $^{13}$C NMR (CDCl$_3$ and about 10% CD$_3$OD, 75 MHz) δ 174.32, 173.92, 173.81, 76.08, 74.67, 71.61, 64.73, 47.64, 45.39, 44.41, 43.49, 40.97, 37.99, 34.99, 34.77, 34.71, 34.52, 31.96, 31.54, 31.35, 30.96, 29.39, 29.36, 29.02, 28.82, 27.32, 27.11, 26.11, 25.83, 23.01, 22.82, 22.69, 17.79, 14.28, 12.41; HRFAB-MS (thioglycerol+Na$^+$ matrix) m/e: ([M+Na]$^+$) 714.4651 (100%), calcd. 714.4669.

Compound 342: $^1$H NMR (CDCl$_3$ and about 10% CD$_3$OD, 300 MHz) δ 5.142 (s, 1 H), 4.96 (d, J=2.7 Hz, 1 H), 4.60, (m, 1 H), 4.04 (t, J=6.6 Hz, 2 H), 3.07-2.95 (series of multiplets, 6 H), 2.56-2.43 (series of multiplets, 6 H), 2.38-2.13 (series of multiplets, 2 H), 2.07-1.02 (series of multiplets, 36 H), 0.92 (s, 3 H), 0.88 (t, J=6.6 Hz, 3 H), 0.82 (d, J=6.6 Hz, 3 H), 0.73 (s, 3 H); $^{13}$C NMR (CDCl$_3$ and CD$_3$OD, 75 MHz) δ 174.29, 172.2 171.98, 171.92, 75.52, 74.09, 70.98, 64.67, 47.78, 45.26, 43.52, 40.98, 38.73, 38.62, 38.35, 38.07, 38.03, 37.99, 35.01, 34.81, 34.77, 34.49, 31.92, 31.50, 31.40, 30.99, 29.36, 29.33, 28.93, 28.80, 27.43, 26.96, 26.08, 25.56, 23.07, 22.79, 22.62, 17.73, 14.25, 12.34; HRFAB-MS (thioglycerol+Na$^+$ matrix) m/e: ([M+Na]$^+$) 714.4651 (100%), calcd. 714.4669. Compound 343: $^1$H NMR (CDCl$_3$ and CD$_3$OD, 500 MHz) δ 5.12 (s, 1 H) 4.93 (s, 1 H), 4.59 (m, 1 H), 4.04 (t, J=7 Hz, 2 H), 2.79-2.69 (series of multiplets, 6 H), 2.4621-2.2999 (series of multiplets, 6 H), 2.2033-1.0854 (series of multiplets, 42 H), 0.94 (s, 2 H), 0.91 (s, 1 H), 0.88 (t, J=7 Hz, 3 H), 0.82 (d, J=6.4 Hz, 3 H), 0.75 (s, 3 H); $^{13}$C NMR (CDCl$_3$ and CD$_3$OD, 75 MHz) δ 174.70, 171.97, 171.86, 171.75, 76.10, 74.55, 71.56, 64.85, 47.96, 45.31, 43.37, 40.87, 38.09, 34.86, 34.80, 34.73, 34.46, 32.84, 32.62, 32.27, 31.87, 31.75, 31.42, 31.08, 29.31, 29.28, 29.26, 28.78, 28.73, 27.38, 26.91, 26.05, 25.37, 23.24, 23.15, 22.95, 22.74, 22.71, 22.43, 17.78, 14.11, 12.28; HRFAB-MS (thioglycerol+Na$^+$ matrix) m/e: ([M+Na]$^+$) 798.5624 (100%), calcd. 798.5609.

Benzyl cholate (312): Cholic acid (4.33 g, 10.62 mmol) and 10-caphorsulfonic acid (0.493 g, 2.21 mmol) were dissolved in benzyl alcohol (1.97 mL, 19.3 mmol). The suspension was heated to 50° C. in oil bath and stirred under vacuum (about 13 mm/Hg) for 16 h. Excess benzyl alcohol was removed in vacuo, and the crude product was chromatographed (silica gel, 5% MeOH in CH$_2$Cl$_2$) to give the desire product as a white powder (4.23 g, 81% yield). $^1$H NMR (CDCl$_3$, 500 MHz) δ 7.34-7.33 (m, 5 H), 5.10 (d, J=1.5 Hz, 2 H), 3.92 (s, 1 H), 3.81 (s, 1 H), 3.42 (s, 1 H), 3.40 (br, m, 3 H), 2.44-2.38 (m, 1 H), 2.31-2.25 (m, 1 H), 2.219 (t, J=12 Hz, 2 H), 0.96 (d, J=5.5 Hz, 3 H), 0.86 (s, 3 H), 0.63 (s, 3 H); $^{13}$C NMR (CDCl$_3$, 125 MHz) δ 174.25, 136.30, 128.66, 128.63, 128.32, 128.28, 128.24, 73.18, 71.98, 68.54, 66.18, 47.14, 46.56, 41.69, 39.65, 35.51, 35.37, 34.91, 34.84, 31.49, 31.08, 30.50, 28.31, 27.62, 26.47, 23.35, 22.65, 22.60, 17.42, 12.63, 12.57; HRFAB-MS (thioglycerol+Na$^+$ matrix) m/e: ([M+Na]$^+$) 521.3235 (100%), calcd. 521.3242.

Representative synthesis of compounds 313-315: Benzyl cholate (312) (0.248 g, 0.499 mmol), N-t-Boc-glycine (0.404 g, 2.30 mmol), DCC (0.338 g, 1.49 mmol) and DMAP (0.051 g, 0.399 mmol) were added to $CH_2Cl_2$ (15 mL), and the suspension was stirred for 16 h. The resulting white precipitate was removed by filtration, and the filtrate was concentrated. The product was obtained after chromatography (silica gel, EtOAc/Hexane 0.6:1) as a white powder (0.329 g, 68%). Compound 313: $^1H$ NMR ($CDCl_3$, 300 MHz) δ 7.34-7.33 (m, 5 H), 5.16 (s, 1 H), 5.08 (dd, J=22.5 Hz, 12.3 Hz, 4 H), 5.00 (s, 1 H), 4.60 (m, 1 H), 4.04-3.81 (series of multiplets, 6 H), 2.43-1.01 (series of multiplets, 25 H), 1.46 (s, 9 H), 1.44 (s, 18 H), 0.92 (s, 3 H), 0.797 (d, J=5.7 Hz, 3 H), 0.69 (s, 1 H); $^{13}C$ NMR ($CDCl_3$, 75 MHz) δ 173.99, 170.25, 170.05, 169.85, 155.73, 136.19, 128.69, 128.45, 128.35, 80.06, 77.65, 77.23, 76.80, 76.53, 75.24, 72.19, 66.29, 47.46, 45.35, 43.24, 42.91, 40.89, 38.00, 34.79, 34.66, 34.49, 31.43, 31.25, 30.77, 28.88, 28.40, 27.23, 26.89, 25.74, 22.94, 22.65, 17.61, 12.32; FAB-MS (thioglycerol+$Na^+$ matrix) m/e: ($[M+Na]^+$) 992.5468 (100%), calcd. 992.5460.

Representative synthesis of compounds 316-318: Compound 313 (0.505 g, 0.520 mmol) and Pd (5 wt. % on active carbon, 0.111 g, 0.0521 mmol) were added to MeOH (5 mL). The suspension was stirred under $H_2$ (50 psi) for 20 hours. The solids were removed by filtration and the filtrate was concentrated. Purification of the product via chromatography (silica gel, 5% MeOH in $CH_2Cl_2$) gave a white powder (0.450 g, 98% yield). Compound 316: $^1H$ NMR ($CDCl_3$, 500 MHz) δ 5.20 (s, 1 H), 5.12 (br., 2 H), 4.92 (s, 1 H), 4.55 (m, 1 H), 3.98-3.83 (series of multiplets, 6 H), 2.30-2.13 (series of multiplets, 2 H), 1.96-0.98 (series of multiplets, 30 H), 1.40 (s, 9 H), 1.39 (s, 18 H), 0.87 (s, 3 H), 0.76 (d, J=6.3 Hz, 3 H), 0.68 (s, 3 H); $^{13}C$ NMR ($CDCl_3$ 75 MHz) δ 174.11, 165.60, 165.41, 165.22, 151.28, 151.14, 75.48, 75.26, 71.81, 70.57, 67.50, 45.95, 42.58, 40.65, 38.52, 38.16, 36.17, 33.28, 30.01, 29.78, 26.71, 26.42, 25.95, 24.16, 23.78, 23.40, 23.31, 22.55, 22.16, 21.03, 18.23, 17.93, 12.91, 7.61; FAB-MS (thioglycerol+$Na^+$ matrix) m/e: ($[M+Na]^+$) 902.4997 (21%), calcd. 902.4990.

Representative synthesis of compounds 319-321: Compound 316 (0.375 g, 0.427 mmol), DCC (0.105 g, 0.512 mmol) and DMAP (0.062 g, 0.512 mmol) and N,N-dimethylethanolamine (0.09 ml, 0.896 mmol) were added to $CH_2Cl_2$ (15 mL). The mixture for 16 h, and solvent and excess N,N-dimethyethanolamine were removed in vacuo. The product was purified via chromatography (silica gel EtOAc/hexane/$Et_3N$, 12:10:0.6) giving a white powder (0.330 g, 82% yield). $^1H$ NMR ($CDCl_3$ and about 10% $CD_3OD$, 500 MHz) δ 5.18 (s, 1 H), 5.00 (s, 1 H), 4.19 (t, J=5.0 Hz, 2 H), 3.92 (s, 3 H), 3.81 (s, 3 H), 2.62 (t, J=10 Hz, 2 H), 2.30 (s, 6 H), 1.47 (s, 9 H), 1.47 (s, 1 H), 1.45 (s, 1 H), 2.12-1.05 (series of multiplets, 27 H), 0.96 (s, 3 H), 0.84 (d, J=10.5 Hz, 3 H), 0.78 (s, 3 H); $^{13}C$ NMR ($CDCl_3$ and about 10% $CD_3OD$, 125 MHz) δ 174.19, 170.05, 169.87, 156.21, 79.36, 79.27, 76.06, 76.90, 71.80, 61.19, 57.04, 46.88, 44.87, 44.67, 44.53, 42.78, 42.15, 42.01, 40.43, 37.47, 34.32, 34.11, 33.92, 33.35, 33.25, 30.74, 30.56, 30.16, 28.40, 27.67, 27.62, 26.73, 26.19, 25.18, 25.10, 24.72, 24.49, 22.29, 21.81, 16.76, 11.56; FAB-MS (thioglycerol+$Na^+$ matrix) m/e: ($[M+Na]^+$) 973.5723 (100%), calcd. 973.5725. The white solid from the previous reaction (0.680 g, 0.714 mmol) and MeI (1 M in $CH_2Cl_2$, 1.5 mL) were stirred together for 2 h. The solvent and excess MeI were removed in vacuo giving a white solid (0.812 g about 100%). The product was carried on without further purification.

Representative synthesis of compounds 324-326: Compound 319 (0.812 g, 0.714 mmol) was dissolved in $CH_2Cl_2$ (5 mL) and trifluoroacetic acid (0.5 mL) was added. The mixture was stirred for 16 min. The solvent and excess acid were removed in vacuo, and the resulting oil was chromatographed (silica gel, $CH_2Cl_2$/MeOH/$NH_3.H_2O$ 4:4:1) to give the desired product as a pale glass (0.437 g, 90% yield). Addition of HCl (2 M in ethyl ether, 2.5 mL) gave the trihydrochloride salt of 324 as a pale yellow powder.

Compound 324: $^1H$ NMR (50% $CDCl_3$, 50% $CD_3OD$, 300 MHz) δ 5.43 (s, 1 H), 5.24 (s, 1 H), 4.84 (m, 1 H), 4.66 (m, 2 H), 4.16-3.96 (series of multiplets, 6 H), 3.88 (m, 2 H), 3.37 (s, 9 H), 0.67 (s, 3 H), 0.59 (d, J=6.3 Hz, 3 H), 0.56 (s, 3 H); $^{13}C$ NMR (50% $CDCl_3$, 50% $CD_3OD$, 75 MHz) δ 173.47, 167.06, 167.01, 166.70, 78.01, 76.49, 73.78, 64.98, 57.67, 53.36, 47.49, 46.99, 45.61, 43.28, 40.83, 40.23, 40.10, 37.69, 34.80, 34.48, 34.28, 31.03, 30.63, 30.44, 28.94, 27.05, 26.56, 25.50, 22.53, 21.56, 16.95, 11.37; FAB-MS (thioglycerol+$Na^+$ matrix) m/e: ($[M-I]^+$) 665.4475 (85.6%), cacld 665.4489. Compounds 325 and 326 proved too unstable to chromatograph using the basic eluent used for the purification of 324. Consequently, 325 and 326 were prepared by deprotection of 320 and 321 using HCl(2 M in diethyl ether), followed by tituration with ethyl acetate. The compounds were then used without further purification. $^1H$ NMR spectroscopy indicated that compounds 325 and 326 were >95% pure. Compound 325: $^1H$ NMR (50% $CDCl_3$, 50% $CD_3OD$, 500 MHz) δ 5.21 (s, 1 H), 5.02 (d, J=4 Hz, 1 H), 4.64 (m, 1 H), 4.53 (m, 2 H), 3.74 (m, 2 H), 3.31-3.01 (series of multiplets, 6 H), 3.23 (s, 9 H), 2.96-2.73 (series of multiples, 6 H), 2.51-2.44 (m, 1 H), 2.35-2.29 (m, 1 H), 2.14-1.09 (series of multiplets, 26 H), 0.99 (s, 3 H), 0.85 (d, J=6.5 Hz, 3 H), 0.80 (s, 3 H); $^{13}C$ NMR (50% $CDCl_3$, 50% $CD_3OD$, 125 MHz) δ 172.77, 169.88, 169.56, 169.50, 75.94, 74.44, 71.57, 64.31, 56.94, 52.92, 46.78, 44.59, 42.70, 40.21, 37.16, 34.80, 34.72, 34.66, 34.05, 34.00, 33.78, 33.62, 30.95, 30.91, 30.81, 30.41, 29.96, 29.81, 28.20, 26.37, 26.06, 24.74, 24.24, 22.04, 21.13, 16.54, 10.97; FAB-MS (thioglycerol+$Na^+$ matrix) m/e: ($[M-I]^+$) 707.4958 (25.6%), cacld 707.4958. Compound 326: $^1H$ NMR (50% $CDCl_3$, 50% $CD_3OD$, 500 MHz) δ 5.12 (s, 1H), 4.94 (d, J=2.5 Hz, 1 H), 4.56 (m. 1 H), 4.51 (t, J=2.3 Hz, 2 H), 3.74 (m, 2 H), 3.23 (s, 9 H), 3.05-3.01 (m, 4 H), 2.98 (t, J=7.5 Hz, 2 H), 2.63-2.43 (series of multiplets, 6 H), 2.31-2.24 (series of multiplets, 2 H), 2.07-1.87 (series of multiplets, 12 H), 1.17-1.05 (series of multiplets, 23 H), 0.94 (s, 3 H), 0.82 (d, J=6.0 Hz, 3 H), 0.76 (s, 3 H); $^{13}C$ NMR (50% $CDCl_3$, 50% $CD_3OD$, 125 MHz) δ 171.87, 169.79, 169.59, 169.50, 76.12, 74.70, 71.65, 65.57, 65.08, 64.40, 57.68, 53.74, 52.78, 45.33, 43.54, 41.04, 39.12, 37.92, 43.85, 34.72, 34.56, 34.34, 32.30, 31.47, 31.27, 30.87, 30.58, 29.03, 27.053, 26.84, 25.51, 24.95, 24.91, 22.87, 22.82, 22.65, 21.93, 17.31, 11.81; FAB-MS (thioglycerol+$Na^+$ matrix) m/e: ($[M-I]^+$) 749.5432 (100%), cacld 749.5436.

Example 14

This example includes data indicating the stability of Compounds 352-354 under acidic, neutral and basic conditions.

Figure 9:
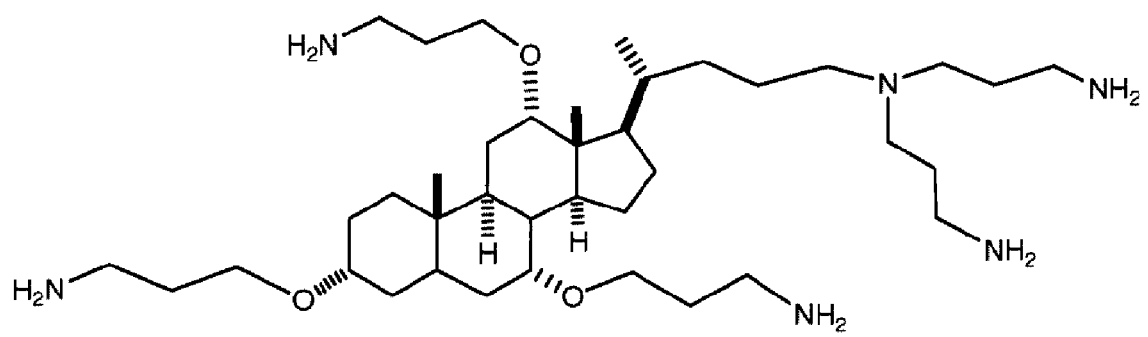

Compounds 352-354 were dissolved in 50 mM phosphate buffered water (pH 2.0, 7.0 or 12.0) at approximately 10 mM concentrations. The structures of compounds 352-354 are given in FIG. 9. Decomposition of the compounds was observed via HPLC (cyano-silica column, 0.15% TFA water-acetonitrile gradient elution). Table 15 shows the stabilities (half-lives) of compounds 352-354 in phosphate buffer at room temperature, pH 2.0, pH 7.0 and pH 12.0. These compounds were used since they contain a chromophore that facilitated monitoring of decomposition by absorption methods common in the HPLC apparatus used.

At low pH, the amines are expected to be protonated and the compounds showed relative stability. At higher pH, the amines were less strongly protonated and became involved in ester hydrolysis. The γ-aminobutyric acid-derived compound was especially susceptible to hydrolysis, presumably yielding pyrrolidone. In general, the compounds are believed to hydrolyse to give cholic acid, choline or octanol, and glycine, beta-alanine, or pyrrolidone, depending on the particular compound.

Decomposition through ester hydrolysis yielded compounds that were less polar and easily separable from the starting compounds. Initially, only one benezene-containing decomposition product was observed; at longer reaction times, two other decomposition products were observed which presumably corresponded to sequential ester hydrolysis, Example 15

This example includes a description of additional exemplary synthetic procedures for producing compounds of formula I. In one example, hydroxyl groups on cholic acid can be converted into amine groups as described in in Hsich et al. (Synthesis and DNA Binding Properties of C3-, C12-, and C24-Substituted Amino-Steroids Derived from Bile Acids, Biorganic and Medicinal Chemistry, 1995, vol. 6, 823-838).

Compounds of formula I prepared as shown in the following Scheme.

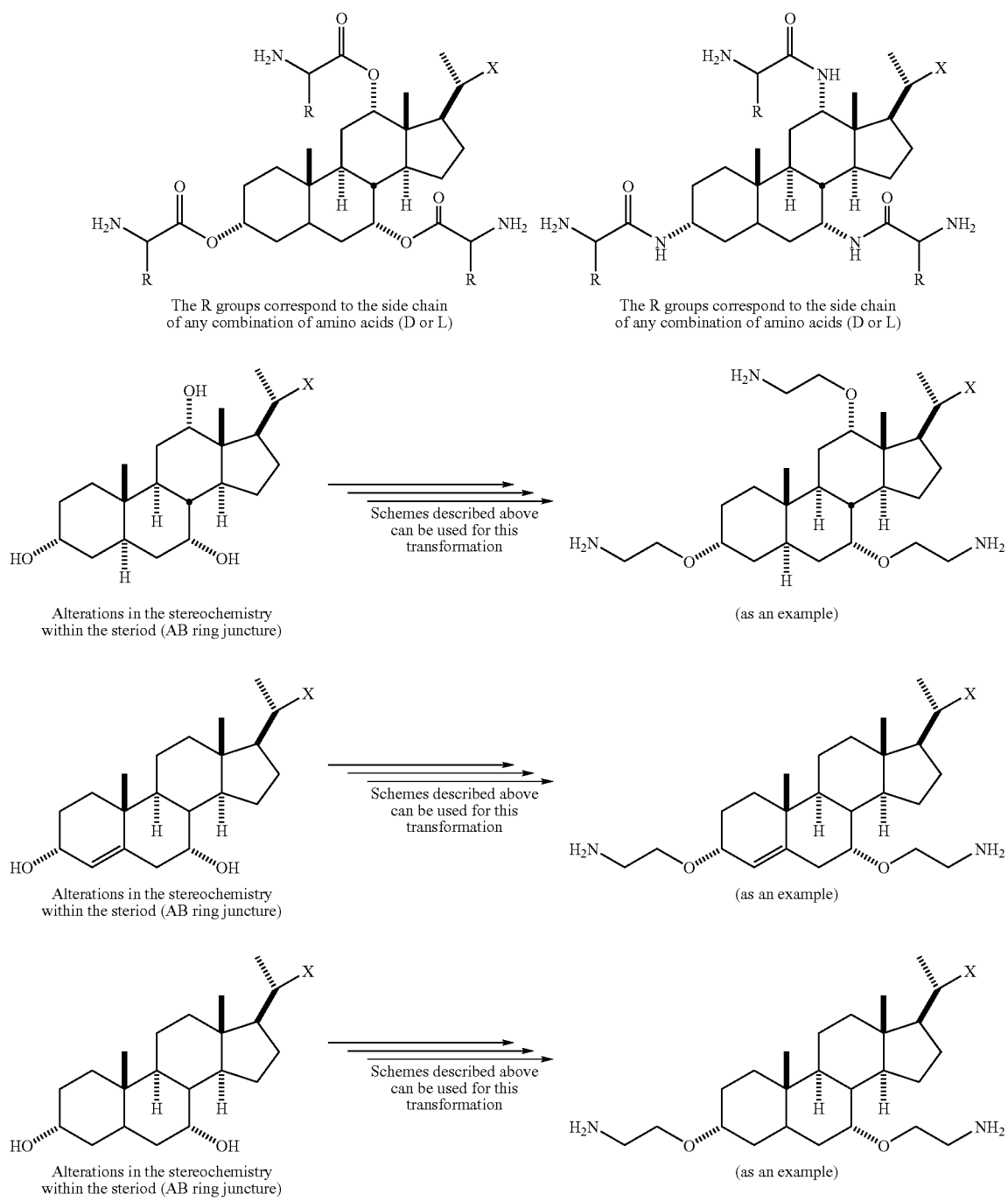

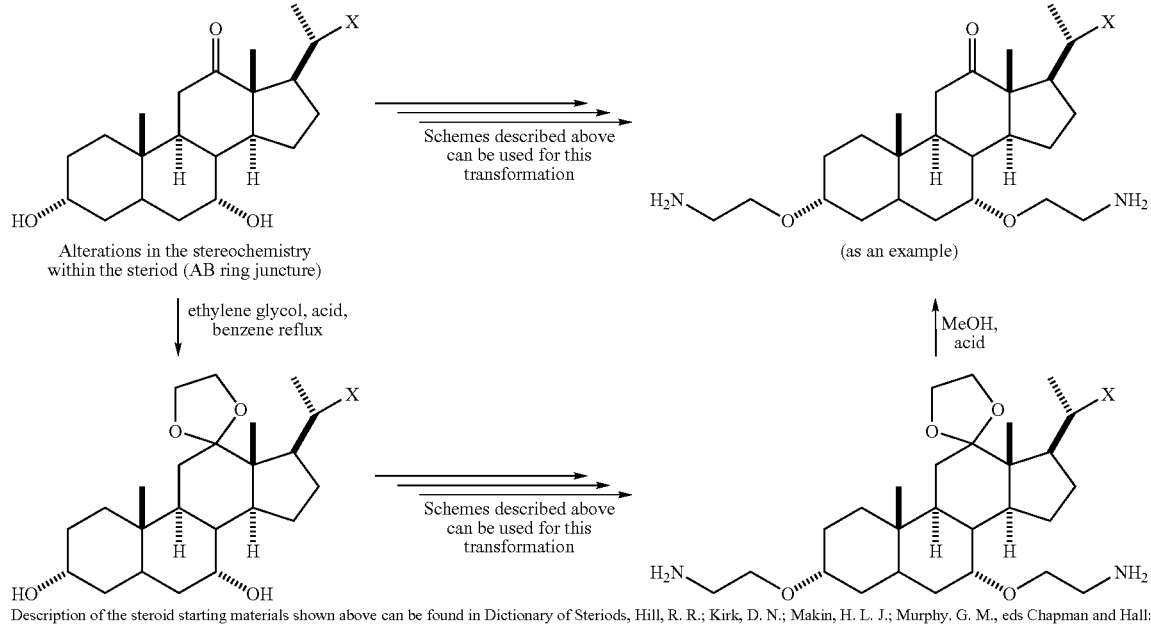

Description of the steroid starting materials shown above can be found in Dictionary of Steriods, Hill, R. R.; Kirk, D. N.; Makin, H. L. J.; Murphy. G. M., eds Chapman and Hall: New York, 1991.

Example 16

This example describes various materials and methods.

Virus source and Culture: The Wyeth strain of vaccinia virus was obtained from the Centers for Disease Control and Prevention. HeLa S3 (ATCC#CCK-2.2) human adenocarcinoma cells were grown to confluence in RPMI media supplemented with 10% fetal calf sera (FCS) for use of propagation of vaccinia virus. The cells were rinsed and overlaid with RPMI-2.5% FCS then inoculated with $5 \times 10^6$ PFU/T-175 flask and incubated at 37° C. in 5% $CO_2$ for three days. Virus was harvested after disruption of cells yielding infectious virions in the form of intracellular mature virions (Schmelz, M. et al., *Journal of Virology* 68:130 (1994)).

Viral Plaque Assay: BS-C-1 (ATCC #CCL-26) African green monkey kidney cells were seeded at $2 \times 10^5$/well in 24 well tissue culture plates in MEM-10% FCS, Pen/Strep and allowed to grow overnight before having the supernatant removed and replaced with MEM-2.5% FCS for virus incubation. The BS-C-1 cells were used for the quantitative estimates because they present uniform plaques. HeLa S3 cells are routinely used for preparations of virus stock as they give consistently high yields of virus, but due to their rounded morphology, do not present uniform plaques.

CSA compounds were diluted in 0.01× tryptic soy broth containing 10 mM sodium phosphate buffer, pH=7.4. Virus diluted in the same buffer was added to the compounds, and they were incubated for 24 hours at 37° C. Twenty microliters of the peptide/virus mixture was added to the cells in 0.5 ml MEM-2.5% FCS and allowed to infect for 24 hours for RNA analysis, or 48 hours for plaque development. For the plaque assay, the medium was removed and wells were overlaid with 0.5 ml 4% buffered formalin, allowed to fix for 10 minutes at room temperature. The formalin was removed and 0.5 ml 0.1% crystal violet in PBS was added to the wells for 5 minutes at room temperature. Wells were then aspirated and air-dried for visualization of plaques. Te most accurate results were obtained with the virus alone forming 50-80 plaques per well.

Keratinocyte Cell Culture: HaCaT cells, a human keratinocyte cell line, were cultured in Dulbecco's Modified Eagle's media (Cellgro) supplemented with 10% FCS (Gemini Bio Products) and 1% of the following: penicillin/streptomycin, L-glutamine, minimal essential medium with non-essential amino acids (GIBCO), MEM vitamins solution (GIBCO) until confluent.

To investigate the anti-viral activity of CSA compounds, cells were seeded in 24 well plates at a concentration of $2 \times 10^5$ cells/well. Cells were infected with vaccinia virus (0.05 plaque forming units/cell) for 6 hours. Following the incubation, virus was removed and the cells were washed with media to remove remaining virus. CSA compounds (0-100 μM) were added to the infected keratinocytes and allowed to incubate for an additional 18 hours. RNA was isolated for analysis of vaccinia virus gene expression.

Vaccinia Gene Expression: RNA was isolated from cultured cells using the RNeasy Mini Kit (Qiagen, Valencia, Calif.) according to manufacturer's guidelines. Real-time PCR was performed using an ABI 7000 Sequence Detection system (Applied Biosystems, Foster City, Calif.). The primer sequences that were used to assay for the vaccinia gene transcripts are: Forward, 5'-GCCAATGAGGGTTCGAGTTC-3' SEQ ID NO.:1 and Reverse, 5'-CAACATCCCGTCGT-TCATCA-3' SEQ ID NO.:2. This region of the genome encodes a subunit of a DNA-directed RNA polymerase expressed within two hours of viral entry (Amegadzie, B. Y. et al., *Journal of Biological Chemistry* 266:13712 (1991)). The TaqMan probe was purchased from Applied Biosystems: 5' labeled with 6-carboxyfluorescein (FAM) and 3'-labeled with 6-carboxy-tetramethylrhodamine (TAMRA). Amplification reactions were performed in MicroAmp optical tubes (Applied Biosystems) in a 25 μl volume containing 2× TaqMan Master Mix (Applied Biosystems), 900 nM forward primer, 900 nM reverse primer, 200 nM probe, and the template RNA.

Thermal cycling conditions were: 50° C. for 2 minutes, 95° C. for 10 minutes for one cycle. Subsequently 40 cycles of amplification were performed at 94° C. for 15 seconds and 60° C. for one minute. In order to quantitatively express the levels of vaccinia virus, a standard curve was generated using cDNA from purified vaccinia virus.

Statistical Analyses: All statistical analysis was conducted using Graph Pad Prism, version 4.01 (San Diego, Calif.). Statistical differences in number of viral plaques or viral gene expression between multiple groups was determined using a one-way analysis of variance (ANOVA) and significant differences determined by a Tukey-Kramer test (Tukey, J., *Exploratory Data Analysis*. Addison Wesley, Reading, N.Y. (1977)).

Observation of CSA Interactions with Vaccinia: A fluorophore labeled CSA (CSA-59) was dissolved in phosphate-buffered saline (PBS) at a concentration of 1.2 μg/ml. Purified vaccinia ($10^8$ PFU/ml) was suspended in PBS at $10^4$, $10^5$, and $10^6$ PFU/4. An aliquot of the CSA solution was placed in a quartz cuvette in a FluoroMax-3 fluorometer. Temperature was held constant at 25° C. The vaccinia virus was titrated into the CSA solution, and fluorescence emission was measured ($\lambda_{ex}$=340 nm, $\lambda_{ex}$=450 nm) in counts per second (CPS). Fluorescent studies with keratinocytes were performed in an identical manner.

Example 17

This example describes the ability of various CSAs to kill vaccinia virus.

Figure 11:
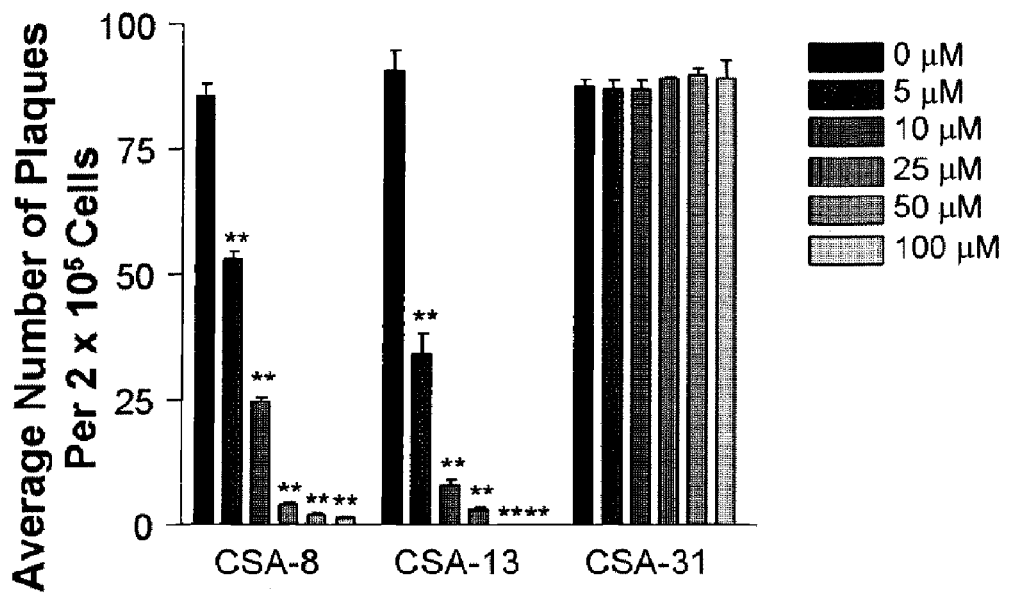

Using a standard viral plaque assay, various CSA were evaluated for the ability to kill vaccinia virus (FIG. 11 and Table 1). CSAs 91 and 92 were most effective in killing vaccinia virus with significant viral killing observed with as little as 1 or 5 micromolar concentrations. CSA-7 and CSA-10 were also effective at killing vaccinia virus with significant viral killing observed with as little as 5 micromolar concentration. CSA-8, CSA-13, CSA-17 and CSA-90 were also effective at 1 or 5 micromolar concentration. CSA-31 and CSA-54 possessed little or no detectable activity against vaccinia at the amounts studied.

Example 18

This example describes data relating to keratinocyte exposure to vaccinia.

Figure 12:
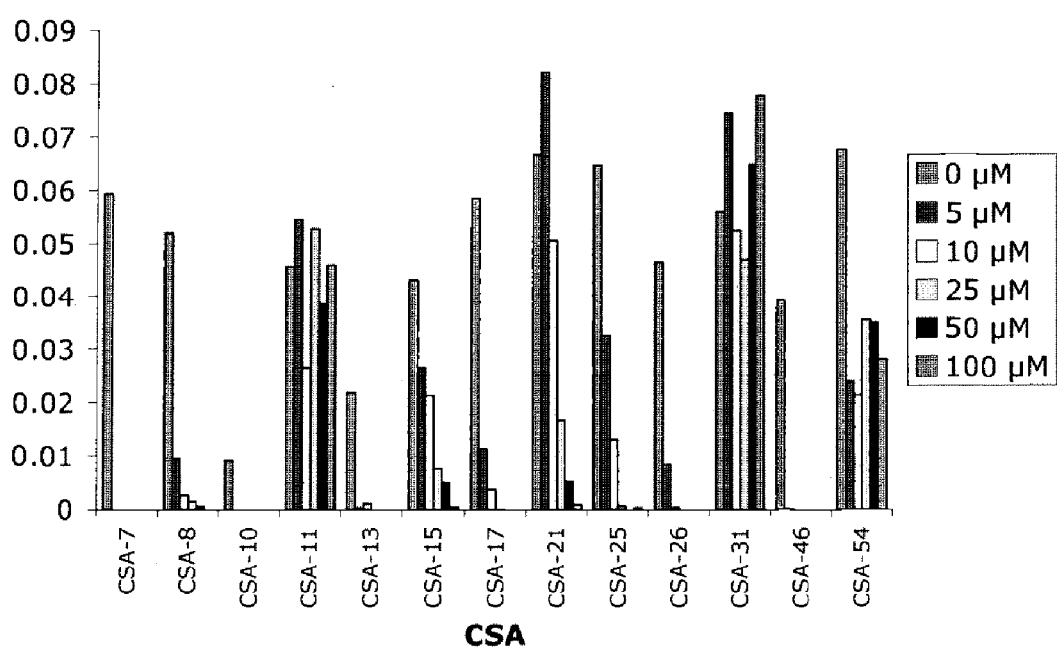

Since the virus must use the host cell for survival, human keratinocytes were infected with vaccinia for 6 hours. At that time, media was removed and replaced with fresh media with or without CSA. Cells and remaining virus were then allowed to incubate for an additional 18 hours. Cells were processed for evaluation of vaccinia gene expression by for real time PCR. In this study, keratinocytes exposed to vaccinia alone had significantly higher levels of vaccinia gene expression than those cells exposed first to vaccinia and then treated with a CSA. Results indicate that CSAs demonstrate a range of activity against vaccinia virus. The most effective compounds are CSA-7, CSA-10, CSA-13, CSA-26 and CSA-46. Considering these antiviral activities and the structures of the CSAs tested (FIG. 12), the following conclusions can be drawn:

(1) The nature of the group at C24 (see FIG. 10 for steroid numbering) influences antiviral activity:
  Charged groups at C24 decreases activity.
  Addition of a lipid chain at C24 increases activity.
(2) Loss of a charged group at C7 decreases activity.
(3) Increasing tether length between the steroid scaffolding and the amine groups at C3, C7, and $C_{12}$ decreases activity.
(4) Dimerization of a CSA results in improved activity.

Example 19

This example describes data showing that CSA-59 preferentially incorporates into the vaccinia lipid envelope over the keratinocyte membrane with a high degree of selectivity.

The fluorophore in CSA-59 (FIG. 10) is related to prodan, which is a small fluorophore that responds to the hydrophobicity of its environment via large changes in fluorescence emission wavelength and intensity. In water, fluorescence emissions of prodan and PBS-59 are centered at 550 nm, and in aprotic solvents the emission intensity increases and is centered at 450 nm. Studies of interactions of CSA-59 and bacteria have reported that incorporation of the antimicrobial into bacterial membranes correlated with increased fluores-

TABLE 1

| % Viability | %100 μM | %50 μM | %25 μM | %10 μM | %5 μM | %1 μM | Number of plaques at 0 μM |
|---|---|---|---|---|---|---|---|
| CSA-92 | 0.00 | 0.00 | 0.00 | 0.00 | 0.00 | 0.00 | 61.67 |
| CSA-91 | 0.00 | 0.00 | 0.00 | 0.00 | 0.00 | 10.31 | 74.33 |
| CSA-10 | 0.00 | 0.00 | 0.00 | 0.00 | 0.37 | | 91.00 |
| CSA-7 | 0.00 | 0.00 | 0.00 | 0.00 | 0.56 | | 87.00 |
| CSA-46 | 0.00 | 0.00 | 0.38 | 3.77 | 41.89 | | 88.33 |
| CSA-13 | 0.00 | 0.00 | 3.31 | 8.82 | 37.50 | | 90.67 |
| CSA-17 | 0.00 | 0.00 | 3.00 | 19.48 | 53.18 | | 89.00 |
| CSA-26 | 0.00 | 0.76 | 4.96 | 43.13 | 82.44 | | 87.33 |
| CSA-59 | 0.00 | 0.54 | 26.09 | 66.31 | 97.83 | | 61.33 |
| CSA-8 | 1.56 | 2.33 | 4.67 | 28.79 | 61.87 | | 85.67 |
| CSA-90 | 0.48 | 4.83 | 7.73 | 14.49 | 23.67 | 64.73 | 69.00 |
| CSA-21 | 4.31 | 14.12 | 40.39 | 71.76 | 100.00 | | 85.00 |
| CSA-86 | 13.62 | 31.92 | 40.85 | 50.70 | 56.34 | 72.30 | 71.00 |
| CSA-25 | 10.04 | 39.41 | 66.91 | 74.35 | 97.40 | | 89.67 |
| CSA-85 | 34.84 | 66.97 | 84.16 | 78.28 | 88.24 | 97.29 | 73.67 |
| CSA-84 | 27.05 | 50.72 | 50.72 | 90.82 | 100.48 | 100.97 | 69.00 |
| CSA-87 | 63.94 | 67.31 | 83.65 | 91.59 | 88.94 | 86.06 | 69.33 |
| CSA-89 | 68.81 | 76.61 | 85.78 | 83.94 | 82.57 | 88.99 | 72.67 |
| CSA-15 | 65.80 | 97.40 | 101.49 | 93.68 | 98.88 | | 89.67 |
| CSA-11 | 98.36 | 97.27 | 100.00 | 92.90 | 84.15 | | 88.45 |
| CSA-54 | 95.53 | 101.12 | 95.53 | 101.12 | 103.91 | | 86.52 |
| CSA-31 | 101.52 | 102.28 | 101.52 | 99.24 | 99.24 | | 87.67 | cent intensity at 450 nm. Association of CSA-59 with vaccinia and keratinocytes was compared based on surface area of the organisms. The surface area of vaccinia was calculated based on an approximate radius of vaccinia of 300 nm, while the surface area of keratinocytes was approximated at 11 µm.

Figure 13:
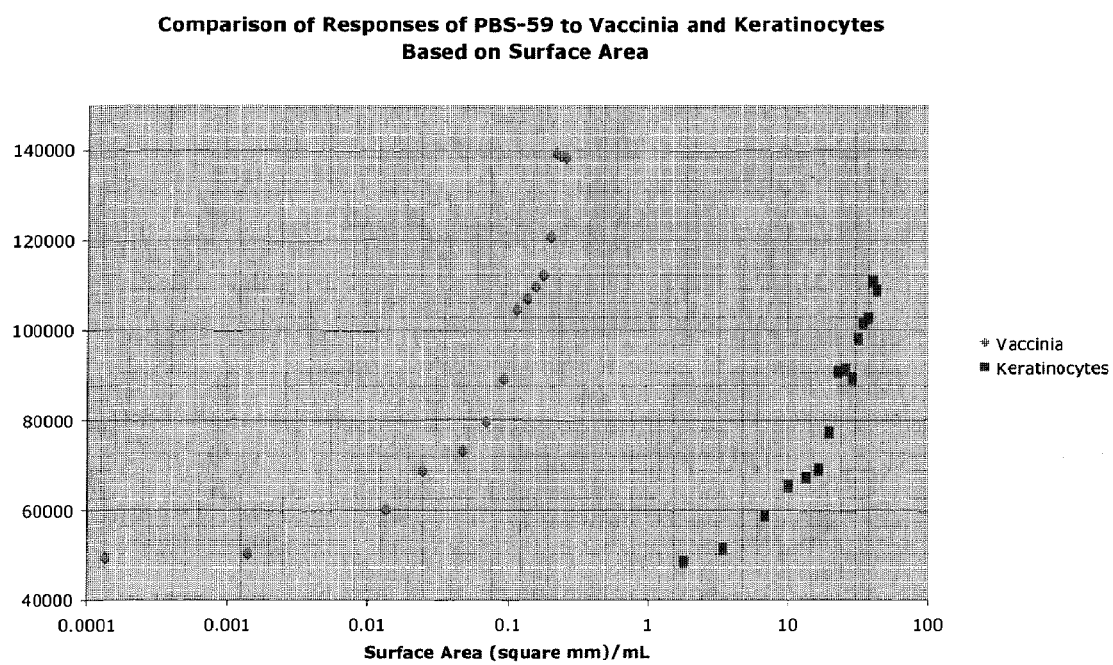

The relationships between surface area and CSA incorporation are shown in FIG. 13. These data indicate that CSA-59 preferentially incorporates into the vaccinia lipid envelope over the keratinocyte membrane with a high degree of selectivity. With much less surface area of lipid envelope present, CSA-59 incorporates into the lipid envelope of vaccinia virus as compared to CSA-59 in the presence of keratinocytes.

sum, camelpox, goatpox, swinepox, sheeppox, buffalopox, sealpox, canarypox, raccoonpox, pigeonpox and rabbitpox.

8. The method of claim 1, wherein the poxvirus comprises a live or attenuated pathogenic or non-pathogenic Vaccinia virus.

9. The method of claim 8, wherein the Vaccinia virus is selected from vaccinia Ankara (MVA), vaccinia virus Lister strain, vaccinia virus Copenhagen strain, vaccinia virus Connaught strain, vaccinia virus Brighton strain, vaccinia virus LC16m8strain, vaccinia virus LC16MO, vaccinia virus IHD-J, vaccinia virus Dairen I, vaccinia virus NYCBOH strain,

What is claimed:

1. A method for providing a subject with protection against a poxvirus infection or pathogenesis, comprising administering a composition comprising a sufficient amount of cationic steroid antimicrobial (CSA), CSA-13, to provide the subject with protection against a poxvirus infection or pathogenesis.

2. The method of claim 1, wherein the CSA is administered concurrently with or following contact of the subject with or exposure of the subject to a poxvirus.

3. The method of claim 1, wherein the CSA is administered concurrently with or following development of a symptom or pathology associated with or caused by poxvirus infection.

4. The method of claim 1, wherein the poxvirus comprises a pathogenic poxvirus.

5. The method of claim 4, wherein the pathogenic poxvirus is selected from variola major and variola minor smallpox virus.

6. The method of claim 5, wherein the variola major or variola minor smallpox virus is an extracellular enveloped virus (EEV), intracellular mature virus (IMV) or cell-associated virus (CEV) form.

7. The method of claim 4, wherein the pathogenic poxvirus is selected from monkeypox, cowpox, Molluscum Contagiovaccinia virus Wyeth strain, vaccinia virus Tian Tan, vaccinia virus LIVP, vaccinia virus L-IPV, vaccinia virus Dryvax® and ACAM1000.

10. The method of claim 1, wherein the CSA comprises a multimer.

11. The method of claim 1, wherein the CSA multimer comprises a dimer, trimer, or tetramer.

12. The method of claim 1, wherein the CSA comprises a pharmaceutically acceptable carrier or excipient.

13. The method of claim 1, wherein the CSA comprises a sterile formulation.

14. The method of claim 1, wherein the subject is provided with partial or complete protection against a poxvirus infection or pathogenesis, or a symptom caused by a poxvirus infection or pathogenesis.

15. The method of claim 1, wherein the method reduces, decreases, inhibits, ameliorates or prevents onset, severity, duration, progression, frequency or probability of one or more symptoms associated with a poxvirus infection or pathogenesis.

16. The method of claim 15, wherein the symptom is selected from: high fever, muscle aches, fatigue, headache, backache, malaise, rash, blisters, pustules, lesions, delirium, vomiting, diarrhea, excess bleeding and death.

17. A method for providing a subject with protection against a poxvirus infection or pathogenesis, comprising administering a sufficient amount of CSA-13 to provide the subject with protection against the poxvirus infection or pathogenesis.

18. The method of claim 1, wherein the CSA is administered prior to contact of the subject with or exposure of the subject to a poxvirus.

19. The method of claim 1, wherein the CSA is administered prior to development of a symptom or pathology associated with or caused by poxvirus infection.

* * * * *